(12) United States Patent
Cocito et al.

(10) Patent No.: US 6,387,372 B1
(45) Date of Patent: May 14, 2002

(54) POLYPEPTIDES FROM MYCROBACTERIUM PARATUBERCULOSIS

(75) Inventors: Carlo Cocito, Ottignies; Marc Coene, Brussels; Myriam De Kesel, Ottingies; Philippe Gilot, Brussels, all of (BE)

(73) Assignee: N.V. Innogenetics S.A. (BE)

( * ) Notice: Subject to any disclaimer, the term of this patent is extended or adjusted under 35 U.S.C. 154(b) by 0 days.

(21) Appl. No.: 08/122,458

(22) PCT Filed: Mar. 24, 1992

(86) PCT No.: PCT/EP92/00661
§ 371 Date: Nov. 19, 1993
§ 102(e) Date: Nov. 19, 1993

(87) PCT Pub. No.: WO92/16628
PCT Pub. Date: Oct. 1, 1992

(30) Foreign Application Priority Data

Mar. 25, 1991 (EP) .............................. 91400798

(51) Int. Cl.$^7$ ................. A61K 39/00; A61K 39/02; G01N 33/554; C07K 1/00
(52) U.S. Cl. ............... 424/185.1; 424/190.1; 424/192.1; 424/234.1; 424/248.1; 435/7.32; 530/300; 530/350; 530/403
(58) Field of Search .............. 530/300, 350, 530/403; 435/7.32; 424/185.1, 190.1, 192.1, 234.1, 248.1

(56) References Cited

U.S. PATENT DOCUMENTS 5,668,013 A * 9/1997 Posner et al.

FOREIGN PATENT DOCUMENTS

| WO | WO-A-8808456 | 3/1988 |
| WO | WO-A-8903892 | 5/1989 |

OTHER PUBLICATIONS

Bech–Nielsen et al. Am. J. Vet. Res. 46(11):2418–20, 1985.*
Burgess et al. J. Cell Biol. 111:2129–38, Nov. 1990.*
Lazar et al. Mol. Cellular Biology 8(3):1247–52, Mar. 1988.*
Plotkin, S.A. et al. (ed.), "Vaccines", see Chapter 29, p. 571, published by WB Saunders Company (Philadelphia), 1988.*
Harlow, E. (ed.), "Antibodies, A Laboratory Manual", see pp. 560 and 684, published by Cold Spring Harbor Laboratory, 1988.*
Abbas, B., et al., "Isolation of specific peptides from *Mycobacterium paratuberculosis* protoplasm and their use . . . ", *Am J Vet Res*, 44:(12):2229–2236 (Dec. 1983).
Bech–Nielsen, S., et al., "Characterization of *Mycobacterium paratuberculosis* antigenic proteins", *Am J Vet Res*, 46: (11):2418–2420 (Nov. 1985).
Cocito, C., et al., "Subcellular localisation and sedimentation behaviour of antigen 60 from *Mycobacterium bovis* BCG", *Med Microbiol Immunol*, 177: 15–25 (1988).
Cocito et al., *Clin. Exp. Immunol.*, 66:262–272 (1986).
Murley et al., *Int. J. Sys. Bacteriol.*, 38:143–146 (1988).
McFadden et al., *J. Clin. Microbiol.*, 25:796–801 (1987).

* cited by examiner

*Primary Examiner*—Mark Navarro
(74) *Attorney, Agent, or Firm*—Merchant & Gould P.C.

(57) ABSTRACT

The invention relates to a polypeptide containing in its polypeptidic chain: the amino acid sequence of 101 amino acids of FIG. 8, or a fragment of this sequence, this fragment being such that it is liable to be recognized by antibodies also recognizing the abovesaid sequence of 101 amino acids, but it is not recognized by antibodies respectively raised against *M. bovis, M. avium, M. phlei* and *M. tuberculosis,* and possibly against *M. leprae, M. intracellulare, M. scrofulaceum, M. fortuitum, M. gordonae* and *M. smegmatis;* it is liable to generate antibodies which also recognize the abovesaid sequence of 101 amino acids but which do not recognize *M. bovis, M. avium, M. Phlei* and *M. smegmatis;* it reacts with the majority of sera from cattle suffering from Johne's disease; or the polypeptidic sequences resulting from the modification by substitution and/or by addition and/or by deletion of one or several amino acids in so far as this modification does not alter the above-mentioned properties.

12 Claims, 27 Drawing Sheets

FIG. 1 (1)
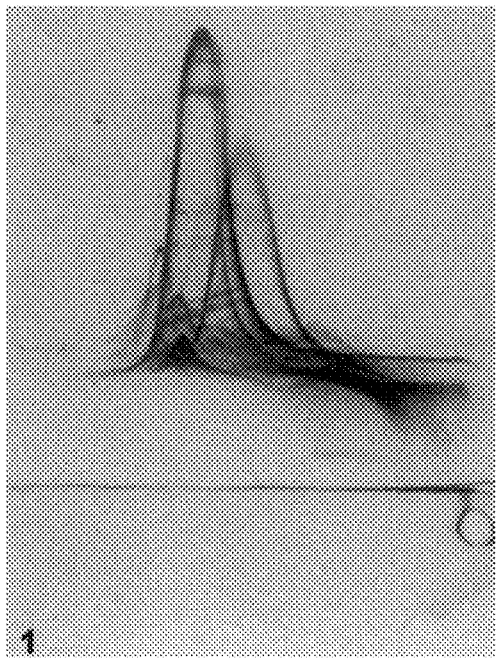
FIG. 1 (2)
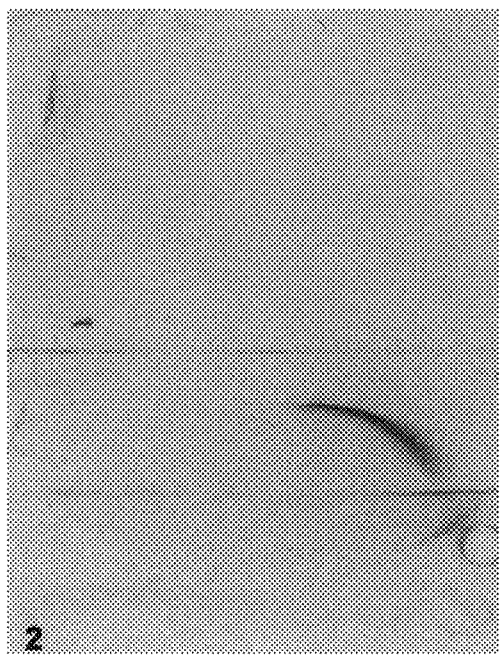

```
GAATTCCCGG GTGGTCAGCA GCATTCGCCG CAGGXCTACG GGTCGCAGTA CGGCGGGTTAC    60
CTTAAGGGCC CACCAGTCGT CGTAAGCGGC GTCCGGATGC CCAGCGTCAT GCCGCCAATG

GGCCAGGGCG GCGCTCCGAC CGGCGGTTTC GGTGCCCAGC CGTCGCCGCA GTCCGGCCCG   120
CCGGTCCCGC CGGAGGCTG  GCCGCCAAAG CCACGGGTCG GCAGCGGCGT CAGGCCGGGC

CAACAGTCCG CGCAGCAGCA GGGCCCGTCC ACACCGCCCA CCGGCTTCCC CAGCTTCAGC   180
GTTGTCAGGC GCGTCGTCGT CCCGGGCAGG TGTGGCGGGT GGCCGAAGGG GTCGAAGTCG

CCGCYGCCCA ACGTCGGCGG GGGATCGGAC TCCGGTTCGG CGACCGCCAA TTACTCCGAG   240
GGCGPCGGGT TGCAGCCGCC CCCTAGCCTG AGGCCAAGCC GCTGGCGGTT AATGAGGCTC

CAGGCCGGTG GZCCAGCAGT CCTACGGCCA GGAGCCTTCT TCACCGTCTG GGCCGACGCC   300
GTCCGGCCAC CHGGTCGTCA GGATGCCGGT CCTCGGAAGA AGTGGCAGAC CCGGCTGCGG

CGCCTAACGT GCCCTGTCGC GCCTAGTCGG GCCCAGCGCC GAACGTGCCC CAGAGTGACA   360
GCGGATTGCA CGGGACAGCG CGGATCAGCC CTTGCACGGG GTCTCACTGT GCCCACCTCC

ACAACCGGGC AGCGGGCGCT CGCCAGGCGC GTGACCTCGT CAGGGTCGCG TTCGCCCCGG   420
TGTTGGCCCG TCGCCCCGA  GCGGTCCCGG CACTGGAGCA GTCCCAGCGC AAGGGGGGCC

CGGTGGTGGC ACTGGTCATC ATCGCCCGGG TCACGCTGAT CCAGTTGTTG ATCGCCAACA   480
GCCACCACCG TGACCAGTAG TAGCGGGCCC AGTGCGACTA GGTCAACAAC TAGCGGTTGT

GCGACATGAC CGGCGCGTTG GGGAATTC                                      508
CGCTGTACTG GCCGCGCAAC CCCTTAAG
```

FIG.7B

```
GAATTCCCGG  GTGGTCAGCA  GCATTCGCCG  CAGGCTACGG  GTCGCAGTAC  GGCGGGTTACG   60
CTTAAGGGCC  CACCAGTCGT  CGTAAGCGGC  GTCCGATGCC  CAGCGTCATG  CCGCCAATGC

GCCAGGGCGG  CGCTCCGACC  GGCGGTTTCG  GTGCCCAGCC  GTCGCCGCAG  TCCGGCCCGC  120
CGGTCCCGCC  GCGAGGCTGG  CCGCCAAAGC  CACGGGTCGG  CAGCGGCGTC  AGGCCGGGCG

AACAGTCCGC  GCAGCAGCAG  GGCCCGTCCA  CACCGCCCAC  CGGCTTCCCC  AGCTTCAGCC  180
TTGTCAGGCG  CGTCGTCGTC  CCGGGCAGGT  GTGGCGGGTG  GCCGAAGGGG  TCGAAGTCGG

CGCGGCCCAA  CGTCGGCGGG  GGATCGGACT  CCGGTTCGGC  GACCGCCAAT  TACTCCGAGC  240
GCGCCGGGTT  GCAGCCGCCC  CCTAGCCTGA  GGCCAAGCCG  CTGGCGGTTA  ATGAGGCTCG

AGGCCGGTGG  CCCAGCAGTC  CTACGGCCAG  GAGCCTTCTT  CACCGTCTGG  GCCGACGCCC  300
TCCGGCCACC  GGGTCGTCAG  GATGCCGGTC  CTCGGAAGAA  GTGGCAGACC  CGGCTGCGGG

GCCTAACGTG  CCCTGTCGCG  CCTAGTCGGG  AACGTGCCCC  AGAGTGACAC  GGGTGGAGGA  360
CGGATTGCAC  GGGACAGCGC  GGATCAGCCC  TTGCACGGGG  TCTCACTGTG  CCCACCTCCT

CAACCGGGCA  GCGGGGCGCTC  GCCAGGGCCG  TGACCTCGTC  AGGGTCGCGT  TCGCCCCGGC  420
GTTGGCCCGT  CGCCCCGCGAG  CGGTCCGGC   ACTGGAGCAG  TCCCAGCGCA  AGCGGGGCCG

GGTGGTGGCA  CTGGTCATCA  TCGCCGCGGT  CACGCTGATC  CAGTTGTTGA  TCGCCAACAG  480
CCACCACCGT  GACCAGTAGT  AGCGGCGCCA  GTGCGACTAG  GTCAACAACT  AGCGGTTGTC

CGACATGACC  GGCGGTTGG   GGAATTC                                         507
GCTGTACTGG  CCGGCCAACC  CCTTAAG
```

FIG.7C

```
GAATTCCCGG GTGGTCAGCA GCATTCGCCG CAGGGCTACG GGTCGCAGTA CGGCGGTTAC
CTTAAGGGCC CACCAGTCGT CGTAAGCGGC GTCCCGATGC CCAGCGTCAT GCCGCCAATG    60

GGCCAGGGCG GCGCTCCGAC CGGCGGTTTC GGTGCCCAGC CGTCGCCGCA GTCCGGCCCG
CCGGTCCCGC CGCGAGGCTG GCCGCCAAAG CCACGGGTCG GCAGCGGCGT CAGGCCGGGC   120

CAACAGTCCG CGCAGCAGCA GGGCCCGTCC ACACCGCCCA CCGGCTTCCC CAGCTTCAGC
GTTGTCAGGC GCGTCGTCGT CCCGGGCAGG TGTGGCGGGT GGCCGAAGGG GTCGAAGTCG   180

CCGCCGCCCA ACGTCGGCGG GGGATCGGAC TCCGGTTCGG CGACCGCCAA TTACTCCGAG
GGCGGCGGGT TGCAGCCGCC CCCTAGCCTG AGGCCAAGCC GCTGGCGGTT AATGAGGCTC   240

CAGGCCGGTG GCCAGCAGTC CTACGGCCAG GAGCCTTCTT CACCGTCTGG GCCGACGCCC
GTCCGGCCAC CGGTCGTCAG GATGCCGGTC CTCGGAAGAA GTGGCAGACC CGGCTGCGGG   300

GCCTAACGTG CCCTGTCGCG CCTAGTCGGG AACGTGCCCC AGAGTGACAC GGGTGGAAGA
CGGATTGCAC GGGACAGCGC GGATCAGCCC TTGCACGGGG TCTCACTGTG CCCACCTCCT   360

CAACCGGGCA GCGGGGCGCTC GCCAGGCGCG TGACCTCGTC AGGGTCGCCT TCGCCCCGGC
GTTGGCCCGT CGCCCCGCGAG CGGTCCGCGC ACTGGAGCAG TCCCAGGCGA AGCGGGGCCG   420

GGTGGTGGCA CTGGTCATCA TCGCCGCGGT CACGCTGATC CAGTTGTTGA TCGCCAACAG
CCACCACCGT GACCAGTAGT AGCGGCGCCA GTGCGACTAG GTCAACAACT AGCGGTTGTC   480

CGACATGACC GGCGCGTTGG GGAATTC
GCTGTACTGG CCGCGCAACC CCTTAAG                                        507
```

FIG.8

| | | | | | | | | | | | | | | |
|---|---|---|---|---|---|---|---|---|---|---|---|---|---|---|
| GAA | TTC | CCG | GGT | GGT | CAG | CAG | CAT | TCG | CCG | CAG | GGC | TAC | GGG | TCG | 45
| Glu | Phe | Pro | Gly | Gly | Gln | Gln | His | Ser | Pro | Gln | Gly | Tyr | Gly | Ser |
| | | | | 5 | | | | | 10 | | | | | 15 |

| CAG | TAC | GGC | GGT | TAC | GGC | CAG | GGC | GGC | GCT | CCG | ACC | GGC | GGT | TTC | 90
|---|---|---|---|---|---|---|---|---|---|---|---|---|---|---|---|
| Gln | Tyr | Gly | Gly | Tyr | Gly | Gln | Gly | Gly | Ala | Pro | Thr | Gly | Gly | Phe |
| | | | | 20 | | | | | 25 | | | | | 30 |

| GGT | GCC | CAG | CCG | TCG | CCG | CAG | TCC | GGC | CCG | CAA | CAG | TCC | GCG | CAG | 135
|---|---|---|---|---|---|---|---|---|---|---|---|---|---|---|---|
| Gly | Ala | Gln | Pro | Ser | Pro | Gln | Ser | Gly | Pro | Gln | Gln | Ser | Ala | Gln |
| | | | | 35 | | | | | 40 | | | | | 45 |

| CAG | CAG | GGC | CCG | TCC | ACA | CCG | CCC | ACC | GGC | TTC | CCC | AGC | TTC | AGC | 180
|---|---|---|---|---|---|---|---|---|---|---|---|---|---|---|---|
| Gln | Gln | Gly | Pro | Ser | Thr | Pro | Pro | Thr | Gly | Phe | Pro | Ser | Phe | Ser |
| | | | | 50 | | | | | 55 | | | | | 60 |

| CCG | CCG | CCC | AAC | GTC | GGC | GGG | GGA | TCG | GAC | TCC | GGT | TCG | GCG | ACC | 225
|---|---|---|---|---|---|---|---|---|---|---|---|---|---|---|---|
| Pro | Pro | Pro | Asn | Val | Gly | Gly | Gly | Ser | Asp | Ser | Gly | Ser | Ala | Thr |
| | | | | 65 | | | | | 70 | | | | | 75 |

| GCC | AAT | TAC | TCC | GAG | CAG | GCC | GGT | GGC | CAG | CAG | TCC | TAC | GGC | CAG | 270
|---|---|---|---|---|---|---|---|---|---|---|---|---|---|---|---|
| Ala | Asn | Tyr | Ser | Glu | Gln | Ala | Gly | Gly | Gln | Gln | Ser | Tyr | Gly | Gln |
| | | | | 80 | | | | | 85 | | | | | 90 |

| GAG | CCT | TCT | TCA | CCG | TCT | GGG | CCG | ACG | CCC | GCC | TAA | | | | 306
|---|---|---|---|---|---|---|---|---|---|---|---|---|---|---|---|
| Glu | Pro | Ser | Ser | Pro | Ser | Gly | Pro | Thr | Pro | Ala | --- | | | |
| | | | | 95 | | | | | 100 | | | | | |

FIG.9B

From: pmTNF MPH

```
      3        9        15       21       27       33       39       45
      |        |        |        |        |        |        |        |
  1  AAT TCC GGG GAT CTC TCA CCT ACC AAA CAA TGC CCC CCT GCA AAA
     TTA AGG CCC CTA GAG AGT GGA TGG TTT GTT ACG GGG GGA CGT TTT

46  AAT AAA TTC ATA TAA AAA ACA TAC AGA TAA CCA TCT GCG GTG ATA
     TTA TTT AAG TAT ATT TTT TGT ATG TCT ATT GGT AGA CGC CAC TAT

91  AAT TAT CTC TGG CGG TGT TGA CAT AAA TAC CAC CGG TGA TAC
     TTA ATA GAG ACC GCC ACA ACT GTA TTT ATG GTG ACC GCC ACT ATG

136  TGA GCA CAT CAG CAG GAC GCA CTG ACC ATG AAG GTG ACG CTC
     ACT CGT GTA GTC CTG CGT GAC TGG TAC TTC CAC TGC GAG

181  TTA AAA ATT AAG CCC TGA AGA AGG GCA GGG GTA CCA GGA GGT TTA
     AAT TTT TAA TTC GGG ACT TCT CCT CGT CCC CAT GGT CCT CCA AAT

226  AAT CAT GGT AAG ATC TAG TCA AAA TTC GAG TGA CAA GCC TGT
     TTA GTA CCA TTC TAG ATC AGT TTT AAG CTC ACT GTT CGG ACA

271  AGC CCA CGT CGT AGC AAA CCA AGT GGA GCA GGG AAT TCA
     TCG GGT GCA GCA TCG TTT GGT TCA CCT CGT CCC TTA AGT

316  CCA TCA CCA TCA CCA CGT GGA TCC CGG GCC CAT GGC TTT CCG GAG
     GGT AGT GGT AGT GGT GCA CCT AGG GCC CGG GTA CCG AAA GGC CTC
```

FIG.9C

```
361  GCC TCT AGA GTC GAC CGG CAT GCA AGC TTA AGT AAG TAA GCC GCC
     CGG AGA TCT CAG CTG GCC GTA CGT TCG AAT TCA TTC ATT CGG CGG

406  AGT TCC GCT GGC GGC ATT TTN NTT GAT GCC CAA GCT TGG CTG TTT
     TCA AGG CGA CCG CCG TAA AAN NAA CTA CGG GTT CGA ACC GAC AAA

451  TGG CGG ATG AGA GAA GAT TTT CAG CCT GAT ACA GAT TAA ATC AGA
     ACC GCC TAC TCT CTT CTA AAA GTC GGA CTA TGT CTA ATT TAG TCT

496  ACG CAG AAG CGG TCT GAT AAA ACA GAA TTT GCC CGG CAG TAG
     TGC GTC TTC GCC AGA CTA TTT TGT CTT AAA CGG GCC GTC ATC

541  CGC GGT GGT CCC ACC TGA CCC CAT GCC GAA CTC AGA AGT GAA ACG
     GCG CCA CCA GGG TGG ACT GGG GTA CGG CTT GAG TCT TCA CTT TGC

586  CCG TAG CGC CGA TGG TAG TGT GGG GTC CAG TCC CCA TGC GAG AGT AGG
     GGC ATC GCG GCT ACC ATC ACA CCC GTC AGG GGT ACG CTC TCA TCC

631  GAA CTG CCA GGC ATC AAA TAA AAC GAA AGG CTC AGT CGA AAG ACT
     CTT GAC GGT CCG TAG TTT ATT TTG CTT TCC GAG TCA GCT TTC TGA

676  GGG CCT TTC GTT TTA TCT GTT TGT GTT CGG TGA ACG CTC TCC TGA
     CCC GGA AAG CAA AAT AGA CAA ACA ACA GCC ACT TGC GAG AGG ACT

721  GTA GGA CAA ATC CGC CGG GAG CGG ATT TGA ACG TTG CGA AGC AAC
     CAT CCT GTT TAG GCG GCC CTC GCC TAA ACT TGC AAC GCT TCG TTG
```

FIG.9D

```
766  GGC CCG GAG GGT GGC GGG CAG GAC GCC CGC CAT AAA CTG CCA GGC
     CCG GGC CTC CCA CCG CCC GTC CTG CGG GCG GTA TTT GAC GGT CCG

811  ATC AAA TTA AGC AGA AGG CCA TCC TGA CGG ATG GCC TTT TTG CGT
     TAG TTT AAT TCG TCT TCC GGT AGG ACT GCC TAC AAA AAC GCA

856  TTC TAC AAA CTC TTT TGT TTA TTT TTC TAA ATA CAT TCA AAT ATG
     AAG ATG TTT GAG AAA ACA AAT AAA AAG ATT TAT GTA AGT TTA TAC

901  TAT CCG CTC ATG AGA CAA TAA CCC TGA TAA ATG CTT CAA TAA TAA
     ATA GGC GAG TAC TCT GTT ATT GGG ACT ATT TAC GAA GTT ATT ATT

946  AAG GAT CTA GGT GAA GAT CCT TTT TGA TAA TCT CAT GAC CAA AAT
     TTC CTA GAT CCA CTT CTA GGA AAA ACT ATT AGA GTA CTG GTT TTA

991  CCC TTA ACG TGA GTT TTC GTT CCA CTG AGC GTC AGA CCC CGT AGA
     GGG AAT TGC ACT CAA AAG CAA GGT GAC TCG CAG TCT GGG GCA TCT

1036 AAA GAT CAA AGG ATC TTC TTG AGA TCC TTT TTT TCT GCG CGT AAT
     TTT CTA GTT TCC TAG AAG AAC TCT AGG AAA AAA AGA CGC GCA TTA
```

FIG.9E

```
1081  CTG CTG CTT GCA AAC AAA ACC ACC GCT ACC AGC GGT GGT TTG
      GAC GAC GAA CGT TTG TTT TGG TGG CGA TGG TCG CCA CCA AAC

1126  TTT GCC GGA TCA AGA GCT ACC AAC TCT TTT TCC GAA GGT AAC TGG
      AAA CGG CCT AGT TCT CGA TGG TTG AGA AAA AGG CTT CCA TTG ACC

1171  CTT CAG CAG AGC GCA GAT ACC AAA TAC TGT CCT TCT AGT GTA GCC
      GAA GTC GTC TCG CGT CTA TGG TTT ATG ACA GGA AGA TCA CAT CGG

1216  GTA GTT AGG CCA CCA CTT CAA GAA CTC TGT AGC ACC GCC TAC ATA
      CAT CAA TCC GGT GGT GAA GTT CTT GAG ACA TCG TGG CGG ATG TAT

1261  CCT CGC TCT GCT AAT CCT GTT ACC AGT GGC TGC TGC CAG TGG CGA
      GGA GCG AGA CGA TTA GGA CAA TGG TCA CCG ACG ACG GTC ACC GCT

1306  TAA GTC GTG TCT TAC CGG GTT GGA CTC AAG ACG ATA GTT ACC GGA
      ATT CAG CAC AGA ATG GCC CAA CCT GAG TTC TGC TAT CAA TGG CCT

1351  TAA GGC GCA GCG GTC GGG CTG AAC GGG TTC GTG CAC ACA GCC
      ATT CCG CGT CGC CAG CCC GAC TTG CCC AAG CAC GTG TGT CGG
```

FIG.9F

```
1396 CAG CTT GGA GCG AAC GAC CTA CAC CGA ACT GAG ATA CCT ACA GCG
     GTC GAA CCT CGC TTG CTG GAT GTG GCT TGA CTC TAT GGA TGT CGC

1441 TGA GCA TTG AGA AAG CGC CAC GCT TCC CGA AGG GAG AAA GGC GGA
     ACT CGT AAC TCT TTC GCG GTG CGA AGG GCT TCC CTC TTT CCG CCT

1486 CAG GTA TCC GGT AAG CGG CAG GGT CGG AAC AGG AGA GCG CAC GAG
     GTC CAT AGG CCA TTC GCC GTC CCA GCC TTG TCC TCT CGC GTG CTC

1531 GGA GCT TCC AGG GGG AAA CGC CTG GTA TCT TTA TAG TCC TGT CGG
     CCT CGA AGG TCC CCC TTT GCG GAC CAT AGA AAT ATC AGG ACA GCC

1576 GTT TCG CCA CCT CTG ACT TGA GCG TCG ATT TTT GTG ATG CTC GTC
     CAA AGC GGT GGA GAC TGA ACT CGC AGC TAA AAA CAC TAC GAG CAG
```

FIG. 9G

```
1621 AGG GGG GCG GAG CCT ATG GAA AAA CGC CAG CAA CGC GGC CTT TTT
     TCC CCC CGC CTC GGA TAC CTT TTT GCG GTC GTT GCG CCG GAA AAA

1666 ACG GTT CCT GGC CTT TTG CTG GCC TTT TGC CAT GTT CTT TCC
     TGC CAA GGA CCG GAA AAC GAC CGG AAA ACG GTA CAA GAA AGG

1711 TGC GTT ATC CCC TGA TTC TGT GGA TAA CCG TAT TAC CGC CTT TGA
     ACG CAA TAG GGG ACT AAG ACA CCT ATT GGC ATA ATG GCG GAA ACT

1756 GTG AGC TGA TAC CGC TCG CCG CAG AAC GAC CTG ACT TCC CAG CGA
     CAC TCG ACT ATG GCG AGC GGC GTC TTG CTG GAC TGA AGG GTC GCT

1801 GTC AGT GAG CGA GGA AGC GGA AGA GCG CTG ACT TCC GCG TTT CCA
     CAG TCA CTC GCT CCT TCG CCT TCT CGC GAC TGA AGG CGC AAA GGT

1846 GAC TTT ACG AAA CAC GGA AAC CGA AGA CCA TTC ATG TTG TTG CTC
     CTG AAA TGC TTT GTG CCT TTG GCT TCT GGT AAG TAC AAC AAC GAG

1891 AGG TCG CAG ACG TTT TGC AGC AGT CGC TTC ACG TTC GCT CGC
     TCC AGC GTC TGC AAA ACG TCG TCA GCG AAG TGC AAG CGA GCG
```

FIG.9H

```
1936 GTA TCG GTG ATT CAT TCT GCT AAC CAG TAA GGC AAC CCC GCC AGC
     CAT AGC CAC TAA GTA AGA CGA TTG GTC ATT CCG TTG GGG CGG TCG

1981 CTA GCC GGG TCC TCA ACG ACA GGA GCA CGA TCA TGC GCA CCC GTG
     GAT CGG CCC AGG AGT TGC TGT CCT CGT GCT AGT ACG CGT GGG CAC

2026 GCC AGG ACC CAA CGC TGC CCG AGA TGC GCC GCG TGC GGC TGC TGG
     CGG TCC TGG GTT GCG ACG GGC TCT ACG CGG CGC ACG CCG ACG ACC

2071 AGA TGG CGG ACG CGA TGG ATA TGT TCT GCC AAG GGT TGG TTT GCG
     TCT ACC GCC TGC GCT ACC TAT ACA AGA CGG TTC CCA ACC AAA CGC

2116 CAT TCA CAG TTC TCC GCA AGA ATT GAT TGG CTC CAA TTC TTG GAG
     GTA AGT GTC AAG AGG CGT TCT TAA CTA ACC GAG GTT AAG AAC CTC

2161 TGG TGA ATC CGT TAG CGA GGT GCC GCC GGC TTC CAT TCA GGT CGA
     ACC ACT TAG GCA ATC GCT CCA CGG CGG AAG GTA AGT CCA GCT

2206 GGT GGC CCG GCT CCA TGC ACC GCG ACG CAA CGC GGG GAG GCA GAC
     CCA CCG GGC CGA GGT ACG TGG CGC GTT GCG CCC CTC CGT CTG
```

FIG.9I

```
2251 AAG GTA TAG GGC GCC TAC AAT CCA TGC CAA CCC GTT CCA TGT
     TTC CAT ATC CCG CGG ATG TTA GGT ACG GTT GGG CAA GGT ACA

2296 GCT CGC CGA GGC ATA AAT CGC CGT GAT CAG CGG TCC AGT
     CGA GCG GCT CCG TAT TTA GCG GCA CTA GTC GCC AGG TCA

2341 GAT CGA AGT TAG GCT GGT AAG AGC CGC GAG CGA TCC TTG AAG CTG
     CTA GCT TCA ATC CGA CCA TTC TCG GCG CTC GCT AGG AAC TTC GAC

2386 TCC CTG ATG GTC ATC TAC CTG CCT GGA CAG CAT GGC CTG CAA
     AGG GAC TAC CAG TAG ATG GAC GGA CCT GTC GTA CCG GAC GTT

2431 CGC GGG CAT CCC GAT GCC GCC GGA AGC GAG AAG AAT CAT AAT GGG
     GCG CCC GTA GGG CTA CGG CGG CCT TCG CTC TTC TTA GTA TTA CCC
```

FIG.9J

```
2476  GAA GGC CAT CCA GCC TCG CGT CGC GAA CGC CAG CAA GAC GTA GCC
      CTT CCG GTA GGT CGG AGC GCA GCG CTT GCG GTC GTT CTG CAT CGG

2521  CAG CGC GTC GGC CGC CAT GGC CGC GAT AAT GGC CTG CTT CTC GCC
      GTC GCG CAG CCG GCG GTA CCG GCG CTA TTA CCG GAC GAA GAG CGG

2566  GAA ACG TTT GGT GGC GGG ACC AGT GAC GAA GGC TTG AGC GAG GGC
      CTT TGC AAA CCA CCG CCC TGG TCA CTG CTT CCG AAC TCG CTC CCG

2611  GTG CAA GAT TCC GAA TAC CGC AAG CGA CAG GCC GAT CAT CGT CGC
      CAC GTT CTA AGG CTT ATG GCG TTC GCT GTC CGG CTA GTA GCA GCG

2656  GCT CCA GCG AAA GCG CTC GTC CTC GCC GAA AAT GAC CCA GAG CGC TGC
      CGA GGT CGC TTT CGC CAG GAG CGG CTT TTA CTG GGT CTC GCG ACG

2701  CGG CAC CTG TCC TAC GAG TTG CAT GAT AAA GAA AGT CAT AAG
      GCC GTG GAC AGG ATG CTC AAC GTA CTA TTT CTT CTG TCA GTA TTC

2746  TGC GGC GAC GAT AGT CAT GCC CCG CGC CCA GAA GGA GCT GAC
      ACG CCG CTG CTA TCA GTA CGG GGC GCG GGT CTT CCT CGA CTG
```

FIG.9K

```
2791 TGG GTT GAA GGC TCT CAA GGG CAT CGG TCG ACG CTC TCC CTT ATG
     ACC CAA CTT CCG AGA GTT CCC GTA GCC TGC GAG AGG GAA TAC

2836 CGA CTC CTG CAT TAG GAA GCA GCC CAG TAG TAG GTT GAG GCC GTT
     GCT GAG GAC GTA ATC CTT CGT CGG GTC ATC CAA CTC CGG CAA

2881 GAG CAC CGC CGC AAG GAA TGG TGC ATG CAA GGA GAT GGC GCC
     CTC GTG GCG GCG TTC CTT ACC ACG TAC GTT CCT CTA CCG CGG

2926 CAA CAG TCC CCC GGC CAC GGG GCC TGC CAC ACC CAC GCC GAA
     GTT GTC AGG GGG CCG GTG CCC ACG GTG GTA TGG GTG CGG CTT

2971 ACA AGC GCT CAT GAG CCC GAA GTG GCG AGC CCG ATC TTC CCC ATC
     TGT TCG CGA CTC GGG CTT CAC CGC TCG GGC TAG AAG GGG TAG

3016 GGT GAT GTC GGC GAT ATA GGC GCC AGC AAC CGC ACC TGT GGC GCC
     CCA CTA CAG CCG CTA TAT CCG CGG TCG TTG GCG TGG ACA CCG

3061 GGT GAT GCC GGC CAC GAT GCG TCC GGG GTA GAG GAT CCA CAG GAC
     CCA CTA CGG CCG GTG CTA CGC AGG CCC CAT CTC CTA GGT GTC CTG
```

FIG.9L

```
3106  GGG TGT GGT CGC CAT GAT CGC GTA GTC GAT AGT GGC TCC AAG TAG
      CCC ACA CCA GCG GTA CTA GCG CAT CAG CTA TCA CCG AGG TTC ATC

3151  CGA AGC GAG CAG GAC TGG GCG GCG GCC AAA GCG GTC GGA CAG TGC
      GCT TCG CTC GTC CTG ACC CGC CGC CGG TTT CGC CAG CCT GTC ACG

3196  TCC GAG AAC GGG TGC GCA TAG AAA TTG CAT CAA CGC ATA TAG CGC
      AGG CTC TTG CCC ACG CGT ATC TTT AAC GTA GTT GCG TAT ATC GCG

3241  TAG CAG CAC GCC ATA GTG ACT GGC GAT GCT GTC GGA ATG GAC GAT
      ATC GTC GTG CGG TAT CAC TGA CCG CTA CGA CAG CCT TAC CTG CTA

3286  ATC CCG CAA GAG GCC CGG CAG TAC CGG CAT AAC CAA GCC TAT GCC
      TAG GGC GTT CTC CGG GCC GTC ATG GCC GTA TTG GTT CGG ATA CGG
```

FIG.9M

```
3331 TAC AGC ATC CAG GGT GAC CTG GCC GAG GAT GAC GAT GAG CGC ATT
     ATG TCG TAG GTC CCA CTG GAC CGG CTC CTA CTG CTC GCG TAA

3376 GTT AGA TTT CAT ACA CGG TGC CTG ACT GCG TTA GCA ATT TAA CTG
     CAA TCT AAA GTA TGT GCC ACG GAC TGA CGC AAT CGT TAA ATT GAC

3421 TGA TAA ACT ACC GCA TTA AAG CTT ATC GAT GAT AAG CTG TCA AAC
     ACT ATT TGA TGG CGT AAT TTC GAA TAG CTA CTA TTC GAC AGT TTG

3466 ATG AGA ATT
     TAC TCT TAA

Total number of bases is: 3474.
DNA sequence composition:  845 A;   933 C;   978 G;   716 T;
2 OTHER;
Sequence name: NPMTNFMPH.
```

FIG.10

| | |
|---|---|
| 1 | Met Val Arg Ser Ser Ser Gln Asn Ser Ser Asp Lys Pro Val Ala |
| 16 | His Val Val Ala Asn His Gln Val Glu Glu Gln Gly Ile His His |
| 31 | His His His His Val Asp Pro Gly Pro Met Ala Phe Arg Arg Pro |
| 46 | Leu Glu Phe Pro Gly Gly Gln Gln His Ser Pro Gln Gly Tyr Gly |
| 61 | Ser Gln Tyr Gly Gly Tyr Gly Gln Gly Gly Ala Pro Thr Gly Gly |
| 76 | Phe Gly Ala Gln Pro Ser Pro Gln Ser Gly Pro Gln Gln Ser Ala |
| 91 | Gln Gln Gln Gly Pro Ser Thr Pro Pro Thr Gly Phe Pro Ser Phe |
| 106 | Ser Pro Pro Pro Asn Val Gly Gly Gly Ser Asp Ser Gly Ser Ala |
| 121 | Thr Ala Asn Tyr Ser Glu Gln Ala Gly Gly Gln Gln Ser Tyr Gly |
| 136 | Gln Glu Pro Ser Ser Pro Ser Gly Pro Thr Pro Ala |

FIG.11A

```
GGG CCC GAA CTT GAC GAA CTC GCC GTC GTA GCT GGC TTC CTC GTC   45
GGT CCA CAG CGC CCG CAT CGC TTC CAG GTA TTC GCG CAG CAT GGT   90
GCG GCG CCG GCC CGC CGG CAC GCC GTG GTC GGC GAG TTC GTC GGT  135
GTT CCA GCC GAA CCC GAC GCC GAG GCT GAC CCG GCC GCC GGA CAG  180
ATG GTC AAG GGT GGC AAT ACT TTT CGC CAG CGT GAT CGG GTC GTG  225
TTC GAC CGG CAG GGC CAC CGC GGT GGA CAG CCG CAC CCG CGA GGT  270
GAC GGC ACA GGC CGC GCC CAG ACT GAC CCA CGG GTC CAG GGT GCG  305
CAT GTA GCG GTC GTC GGG CAG CGA CGC GTC GCC GGT GGT CGG GTG  360
CGC GGC CTC CCG CTT GAT CGG GAT ATG CGT GTG TTC CGG CAC GTA  405
GAA GGT CGC AAA CCC GTG GTC GTC GGC AAG CTT CGC GGC CGC AGC  450
CGG AGA GAT GCC ACG GTC GCT GGT GAA AAG CAC AAG CCC GTA ATC  495
CAT GCA GTG AAT TAG AAC GTG TTC TAC CTC TGC GGG GCA AGC TGT  540
CGT GAT ACG GAC CGT CTC GCC GCG CGG TCG TCT GCG AAG CCC GCG  585
GGC AAG CCA ATG GCG ACG GCA CCG GCC GTC GCA CGT GCG CTA GCG  630
TGG GTG ATC GAC CGT GTC GCT CGC GCA GTG ACG CGC CTG CAA GCA  675
CCG CGT CGC ATC GCA ACC GTG GCG CCC GCT CGG CAC TAA AAG GCA  720
GTG GAA GCA ACA GGA GGA GCC ATG ACC TAC TCT CCC GGC AGC CCC  765
                         MET Thr Tyr Ser Pro Gly Ser Pro
                          1               5

GGA TAT CCA CCG GCG CAG TCT GGC GGC ACC TAT GCA GGC GCC ACA  810
Gly Tyr Pro Pro Ala Gln Ser Gly Gly Thr Tyr Ala Gly Ala Thr
    10              15                  20

CCA TCT TTC GCC AAA GAC GAC GAC GGC AAG AGC AAA CTC CCG CTC  855
Pro Ser Phe Ala Lys Asp Asp Asp Gly Lys Ser Lys Leu Pro Leu
    25              30                  35

TAC CTC AAC ATC GCC GTG GTC GCC CTG GGT TTC GCG GCC TAC CTG  900
Tyr Leu Asn Ile Ala Val Val Ala Leu Gly Phe Ala Ala Tyr Leu
    40              45                  50

CTG AAT TTC GGC CCC ACC TTC ACC ATC GGC GCC GAC CTC GGC CCG  945
Leu Asn Phe Gly Pro Thr Phe Thr Ile Gly Ala Asp Leu Gly Pro
    55              60                  65
```

FIG.11B

```
GGT ATC GGC GGC CGC GCG GGT GAC GCC GGC ACC GCC GTC GTG GTG   990
Gly Ile Gly Gly Arg Ala Gly Asp Ala Gly Thr Ala Val Val Val
         70              75                  80

GCG CTG CTG GCC GCG CTG CTC GCC GGG CTG GGC CTG CTG CCC AAG  1035
Ala Leu Leu Ala Ala Leu Leu Ala Gly Leu Gly Leu Leu Pro Lys
         85              90                  95

GCC AAG AGT TAT GTG GGC GTG GTC GCG GTC GTC GCG GTG CTC GCC  1080
Ala Lys Ser Tyr Val Gly Val Val Ala Val Val Ala Val Leu Ala
        100             105                 110

GCG CTG CTG GCC ATC ACC GAG ACG ATC AAC CTG CCC GCC GGT TTC  1125
Ala Leu Leu Ala Ile Thr Glu Thr Ile Asn Leu Pro Ala Gly Phe
        115             120                 125

GCG ATC GGC TGG GCG ATG TGG CCG CTG GTG GCG TGC GTG GTG CTG  1170
Ala Ile Gly Trp Ala MET Trp Pro Leu Val Ala Cys Val Val Leu
        130             135                 140

CAG GCG ATC GCC GCG GTC GTC GTG GTC CTG CTG GAC GCC GGG GTG  1215
Gln Ala Ile Ala Ala Val Val Val Val Leu Leu Asp Ala Gly Val
        145             150                 155

ATC ACG GCG CCG GCG CCG CGG CCC AAG TAC GAC CCC TAC GCG CAG  1260
Ile Thr Ala Pro Ala Pro Arg Pro Lys Tyr Asp Pro Tyr Ala Gln
        160             165                 170

TAC GGC CAA TAC GGG CAA TAC GGC CAG TAC GGG CAA CAG CCC TAC  1305
Tyr Gly Gln Tyr Gly Gln Tyr Gly Gln Tyr Gly Gln Gln Pro Tyr
        175             180                 185

TAC GGT CAG CCG GGC GGT CAG CCC GGG GGC CAG CCG GGT GGT CAG  1350
Tyr Gly Gln Pro Gly Gly Gln Pro Gly Gly Gln Pro Gly Gly Gln
        190             195                 200

CAG CAT TCG CCG CAG GGC TAC GGG TCG CAG TAC GGC GGT TAC GGC  1395
Gln His Ser Pro Gln Gly Tyr Gly Ser Gln Tyr Gly Gly Tyr Gly
        205             210                 215

CAG GGC GGC GCT CCG ACC GGC GGT TTC GGT GCC CAG CCG TCG CCG  1140
Gln Gly Gly Ala Pro Thr Gly Gly Phe Gly Ala Gln Pro Ser Pro
        220             225                 230

CAG TCC GGC CCG CAA CAG TCC GCG CAG CAG CAG GGC CCG TCC ACA  1485
Gln Ser Gly Pro Gln Gln Ser Ala Gln Gln Gln Gly Pro Ser Thr
        235             240                 245
```

FIG.11C

```
CCG CCC ACC GGC TTC CCC AGC TTC AGC CCG CCG CCC AAC GTC GGC   1530
Pro Pro Thr Gly Phe Pro Ser Phe Ser Pro Pro Pro Asn Val Gly
        250             255             260

GGG GGA TCG GAC TCC GGT TCG GCG ACC GCC AAT TAC TCC GAG CAG   1575
Gly Gly Ser Asp Ser Gly Ser Ala Thr Ala Asn Tyr Ser Glu Gln
        265             270             275

GCC GGT GGC CAG CAG TCC TAC GGC CAG GAG CCT TCT TCA CCG TCT   1620
Ala Gly Gly Gln Gln Ser Tyr Gly Gln Glu Pro Ser Ser Pro Ser
        280             285             290

GGG CCG ACG CCC GCC TAA CGT GCC CTG TCG CGC CTA GTC GGG AAC   1665
Gly Pro Thr Pro Ala ---
        295

GTG CCC CAG AGT GAC ACG GGT GGA GGA CAA CCG GGC AGC GGG CGC   1710

TCG CCA GGC GCG TGA CCT CGT CAG GGT CGC GTT CGC CCC GGC GGT   1755

GGT GGC ACT GGT CAT CAT CGC CGC GGT CAC GCT GAT CCA GTT GTT   1800

GAT CGC CAA CAG CGA CAT GAC CGG CGC GTT GGG GAA TTC            1839
```

POLYPEPTIDES FROM MYCROBACTERIUM PARATUBERCULOSIS

The invention relates to polypeptides and peptides, particularly recombinant ones, which can be used for the diagnosis of paratuberculosis in cattle and possibly of Crohn's disease in human beings. The invention also relates to a process for preparing the above-said polypeptides and peptides, which are in a state of biological purity such that they can be used as part of the active principle in the preparation of vaccines against paratuberculosis.

It also relates to nucleic acids coding for said polypeptides and peptides.

Furthermore, the invention relates to the in vitro diagnostic methods and kits using the above-said polypeptides and peptides and to the vaccines containing the above-said polypeptides and peptides as active principle against paratuberculosis.

By "recombinant polypeptides or peptides" it is to be understood that it relates to any molecule having a polypeptidic chain liable to be produced by genetic engineering, through transcription and translation, of a corresponding DNA sequence under the control of appropriate regulation elements within an efficient cellular host. Consequently, the expression "recombinant polypeptides" such as is used herein does not exclude the possibility for the polypeptides to comprise other groups, such as glycosylated groups.

The term "recombinant" indeed involves the fact that the polypeptide has been produced by genetic engineering, particularly because it results from the expression in a cellular host of the corresponding nucleic acid sequences which have previously been introduced into an expression vector used in said host.

Nevertheless, it must be understood that the polypeptides or the peptides of the invention can be produced by a different process, for instance by classical chemical synthesis according to methods used in the protein synthesis or by proteolytic cleavage of larger molecules.

The expression "biologically pure" or "biological purity" means on the one hand a grade of purity such that the polypeptides can be used for the production of vaccinating compositions and on the other hand the absence of contaminants, more particularly of natural contaminants.

Paratuberculosis (Johne's disease) has been described as one of the most serious diseases affecting the world cattle industry. This mycobacteriosis produced by *M. paratuberculosis* is characterized by an ileocoecal enteritis leading successively to emaciation, dysentery, cachexy and death (Chiodini R. J. et al., 1984, "Ruminant paratuberculosis (Johne's disease): the current status and future prospects", Cronell Vet. 74:218–262). Histological examination shows oedema, infiltration and thickening of the ileal mucosa, and hypertrophy and necrosis of intestinal lymphnodes. A miliary syndrome with diffused parenchima granuloma in liver, spleen and lungs is not infrequent. The high contagiousness of this disease is due to excretion of large numbers of bacteria from the intestinal tract: contaminated pastures propagate the infection, rapidly producing live-stocks wherein infected animals represent a large part of the population. Chronical dysentery is an advanced stage of the disease, for epidemiological data suggest that the subclinical cases, with little sign of intestinal alteration correspond to the majority of infected animals and frequently to a large proportion of a live-stock population.

Diagnosis of paratuberculosis is essential, especially in the absence of clinical symptoms: it leads to identification of hidden bacterial shedders and avoids propagation of infection. Unfortunately, diagnostic indicators for early stages of the disease are missing. In fact, identification of the etiological agent (a slow grower) is a lengthy process, and histological examination of biopsy material is difficult and expensive. More interesting appear to be the immunological procedures for analysis of humoral immune reactions (Brugère-Picoux J., 1987, "Le diagnostic de la paratuberculose chez les ruminants", Rec. Méd. Vét. 163:539–546 Colgrave J. S. et al., 1989, "Paratuberculosis in cattle: a comparison of three serologic tests with results of fecal culture", Veterinary Microbiology 19:183–187). Although complement fixation and hemagglutination tests apparently lack both sensitivity and specificity, immunoenzymometric methods for evaluation of antimycobacterial antibodies seem to be more promising (Abbas B. et al., 1983, "Isolation of specific peptides from *Mycobacterium paratuberculosis* protoplasm and their use in an enzyme linked immunosorbent assay for the detection of paratuberculosis (Johne's disease) in cattle", Am. J. Vet. Res. 44:2229–2236; Colgrave J. S. et al., 1989, "Paratuberculosis in cattle: a comparison of three serologic tests with results of fecal culture" Veterinary Microbiology, 19:183–187; Yokomizo Y. et al., 1983, "Enzyme-linked immunosorbent assay for detection of bovine immunoglobulin G1 antibody to a protoplasmic antigen of *Mycobacterium paratuberculosis*" Am. J. Vet. Res. 44:2205–2207; Yokomizo Y. et al., 1985, "A method for avoiding false-positive reactions in an enzyme-linked immunosorbent assay (ELISA) for the diagnosis of bovine paratuberculosis" Japan, J. Vet. Sci. 47:111–119).

Moreover, since slaughtering of cattle affected by tuberculosis (caused by *M. bovis* and/or *M. tuberculosis*), but not of those with paratuberculosis, is compulsory in Occidental countries, a distinction at the immunological level between the two mycobacterial diseases is essential. Moreover, *M. paratuberculosis* is known to be genetically close-related to *M. avium* (Chiodini R. J. et al., 1989, "The genetic relationship between *Mycobacterium paratuberculosis* and the *M. avium* complex" Acta Leprol. 7:249–251; Hurley S. S. et al., 1988, "Deoxyribonucleic acid-relatedness of *Mycobacterium paratuberculosis* to others members of the family Mycobacteriaceae" Int. J. Syst. Bacteriol. 38:143–146), which is a possible host of the intestinal tract of ruminants.

Taking into account the cross reactivity between *M. paratuberculosis* and many other mycobacteria, it was a priori a difficult approach to find an antigen containing specific epitopes liable to be used as reagents for the diagnosis of paratuberculosis, said reagents having no cross reactivity with other close related mycobacteria.

In addition to the above-mentioned aspects relative to paratuberculosis in cattle, *M. paratuberculosis* has been found to play an etiologic role in at least some cases of Crohn's disease in human.

The disease originally described by Crohn and coworkers was a chronical ileitis producing hyperplastic granulomata of the intestine and lymphnodes. The syndrome presently known as Crohn's disease entails inflammatory alterations of different organs of the digestive tract (month, larynx, esophagus, stomach, ileum and colon). Segments of the motive apparatus (joints, muscles and bones) can also be involved. Isolation of mycobacteria from patients affected by the Crohn's disease has been repeatedly related: in several instances isolates were identified as *M. paratuberculosis*. The induction by these isolates of a syndrome mimicking Crohn's disease in laboratory animals and primates has been successful. In a recent review article (Chiodini R. J., 1989, "Crohn's disease and the mycobacterioses: a review and comparison of two disease entities", Clin. Microbiol. Rev. 2:90–117), Chiodini suggests this syndrome to be the expression of several pathological entities and concludes, that, if Crohn's disease has a mycobacterial etiology, the most likely agent would be *M. paratuberculosis*.

At this present time, larger epidemiological investigation with an ELISA based on a specific protein of *M. paratuberculosis* is expected to help to solve the problem of the etiology of this enteritis resembling in many respects the Johne's disease of cattle.

The expression "cattle" means ruminants, such as bovines, sheeps, goats, cervidae, but also include some non ruminant animals which may also be infected by Johne's disease such as monkeys and horses.

An aspect of the invention is to provide recombinant polypeptides which can be used as purified antigens for the detection and control of paratuberculosis.

Another aspect of the invention is to provide nucleic acids coding for the peptidic chains of biologically pure recombinant polypeptides which enable their preparation on a large scale.

Another aspect of the invention is to provide antigens which can be used in serological tests as an in vitro rapid diagnosis of paratuberculosis, as well as in skin tests for in vivo diagnosis of paratuberculosis and as an immunogenic principle in vaccines.

Another aspect of the invention is to provide a rapid in vitro diagnostic means for paratuberculosis, enabling it to discriminate between cattle suffering from tuberculosis from the ones suffering from paratuberculosis.

Another aspect of the invention is to provide a rapid in vitro diagnostic means for paratuberculosis, enabling it to discriminate between cattle suffering from paratuberculosis from the ones infected or colonized by *M. avium*, *M. bovis* or *M. tuberculosis* or *M. phlei*.

Another aspect of the invention is to provide in vitro diagnostic means for patients suffering from Crohn's disease.

The invention relates to an antigen complex from *M. paratuberculosis*, named hereafter "the antigen A36", liable to be obtained as follows:
  sonication of bacterial suspensions of *M. paratuberculosis* to obtain a homogenate (also named sonicate),
  centrifugation of the above-mentioned homogenate to obtain a supernatant (which corresponds to the cytoplasm of the bacteria),
  RNAase digestion of the above-mentioned supernatant,
  fractionation of the digested supernatant, for instance by gel exclusion chromatography, for instance on Sepharose 6B columns,
  recovery of the antigen complex (A36) which is the excluded fraction of the fractionation.

It is to be noted that the antigen complex hereabove defined corresponds to the TMA complex (thermostable macromolecular antigens), belonging to a family of complexes present in all mycobacteria and consisting of or containing lipid, polysaccharide and protein moieties.

The proteic part of the antigen complex of the invention can be fractionated and visualized as follows:
  fractionation of the proteins of the above-mentioned antigen complex by electrophoresis in a gel, for instance 10% polyacrylamide gels to obtain the protein on bands,
  detection of the proteins by staining for instance with Coomassie blue.

The polypeptides of the invention contain in their polypeptidic chain:

the amino acid sequence of 101 amino acids of FIG. 8, or a fragment of this sequence, this fragment being such that:
  it is liable to be recognized by antibodies also recognizing the abovesaid sequence of 101 amino acids, but it is not recognized by antibodies raised respectively against *M. bovis*, *M. avium*, *M. phlei* and *M. tuberculosis*,
  it is liable to generate antibodies which also recognizing the abovesaid sequence of 101 amino acids but which do not recognize *M. bovis*, *M. avium*, *M. phlei* and *M. tuberculosis*,
  it reacts with the majority of sera from cattle suffering from Johne's disease,
or the polypeptidic sequences resulting from the modification by substitution and/or by addition and/or by deletion of one or several amino acids in so far as this modification does not alter the above-mentioned properties.

Recognition of one of the above-mentioned fragments by the above-mentioned antibodies—or of the abovesaid sequence of 101 amino acids by the above-mentioned antibodies—means that the above-mentioned fragment can form a complex with one of the above-said antibodies.

The formation of the complex antigen (i.e. the sequence of 101 amino acids (SEQ ID NO:5) or of the above-said fragment)—antibody and the detection of the existence of a formed complex can be done according to classical techniques such as the ones using a marker labeled by radioactive isotopes or by an enzyme.

Hereafter is also given in a non limitative way, a test for giving evidence of the fact that polypeptides of the invention are recognized selectively by the majority of the sera from cattle suffering from Johne's disease (immunodominant polypeptides), for instance bovines.

This test is an immunoblotting (Western blotting) analysis, in the case where the polypeptides of the invention are obtained by recombinant techniques. This test can also be used for polypeptides of the invention obtained by a different preparation process. After sodium dodecyl sulfate-polyacrylamide gel electrophoresis, polypeptides of the invention are blotted onto nitrocellulose membranes (Hybond C. (Amersham)) as described by Towbin H. et al., 1979, "Electrophoretic transfer of proteins from polyacrylamide gels to nitrocellulose sheets: procedure and some applications", Proc. Natl. Acad. Sci. USA 76:4350–4354. The expression of polypeptides of the invention fused to β-galactosidase in *E. coli* Y1089, is visualized by the binding of a polyclonal rabbit anti-A36 antiserum (or polyclonal rabbit anti-homogenate antiserum defined hereafter in the examples, or polyclonal rabbit anti-βgal-p362 antiserum, defined hereafter in the examples) (1:1,000) or by using a monoclonal anti-β-galactosidase antibody (Promega). The secondary antibody (anti-rabbit immunoglobulin G and anti-mouse immunoglobulin G respectively, both alkaline phosphatase conjugated) is diluted as recommended by the supplier (Promega). Colour reaction is developed by adding NBT/BCIP (Nitro Blue Tetrazolium 5-bromo 4-chloro-3-indolyl phosphate [Promega]) using conditions recommended by suppliers.

In order to identify selective recognition of polypeptides of the invention and of fusion proteins of the invention by sera of bovine suffering from Johne's disease, nitrocellulose sheets are incubated overnight with each of these sera (1:50) (after blocking a specific protein-binding sites).

Reactive areas on the nitrocellulose sheets are revealed by incubation with peroxidase conjugated goat anti-bovine immunoglobulin G antibody (Dakopatts, Copenhagen, Denmark) (1:200) for 4 h, and after repeated washings, color reaction is developed by adding α-chloronaphtol (Bio-Rad Laboratories, Richmond, Calif.) in the presence of hydrogen peroxide.

The non-recognition of the antibodies raised against the above-mentioned fragments of the invention by *M. bovis, M. avium, M. phlei* and *M. tuberculosis* and by other mycobacteria can be done according to a process detailed in the examples.

As to the non-recognition of the above-mentioned fragments of the invention by antibodies raised respectively against *M. bovis, M. avium, M. phlei* and *M. tuberculosis* or other mycobacteria, it can also be done according to a process detailed in the examples.

Advantageous above-defined fragments of the invention are liable not to be recognized by antibodies raised against other mycobacteria such as *M. leprae, M. intracellulare, M. scrofulaceum, M. fortuitum, M. gordonae* and *M. smegmatis*, and are liable to generate antibodies which do not recognize *M. leprae, M. intracellulare, M. scrofulaceum, M. fortuitum, gordonae* and *M. smegmatis*.

It goes without saying that the free reactive functions which are present in some of the amino acids, which are part of the constitution of the polypeptides of the invention, particularly the free carboxyl groups which are carried by the groups Glu and Asp or by the C-terminal amino acid on the one hand and/or the free NH$_2$ groups carried by the N-terminal amino acid or by amino acids inside the peptidic chain, for instance Lys, on the other hand, can be modified in so far as this modification does not alter the above mentioned properties of the polypeptide.

The molecules which are thus modified are naturally part of the invention. The above mentioned carboxyl groups can be acylated or esterified.

Other modifications are also part of the invention. Particularly, the amine or carboxyl functions or both of terminal amino acids can be themselves involved in the bond with other amino acids. For instance, the N-terminal amino acid can be linked to the C-terminal amino acid of another peptide comprising from 1 to several amino acids.

Furthermore, any peptidic sequences resulting from the modification by substitution and/or by addition and/or by deletion of one or several amino acids of the polypeptides according to the invention are part of the invention in so far as this modification does not alter the above mentioned properties of said polypeptides.

The polypeptides according to the invention can be glycosylated or not, particularly in some of their glycosylation sites of the type Asn-X-Ser or Asn-X-Thr, X representing any amino acid.

An advantageous recombinant polypeptide of the invention is constituted by the sequence represented on FIG. 8, extending from the extremity constituted by amino acid at position (1) to the extremity constituted by amino acid at position (101), or by the following peptides:

Glu-Phe-Pro-Gly-Gly-Gln-Gln-His-Ser-Pro-Gln, (position 1 to 11 on FIG. 8) (SEQ ID NO:12)

Gln-Gln-Ser-Tyr-Gly-Gln-Glu-Pro-Ser-Ser-Pro-Ser-Gly-Pro-Thr-Pro-Ala (position 85 to 101 on FIG. 8) (SEQ ID NO:13).

It is to be noted that this polypeptide is derived from the expression product of a DNA derived from the nucleotide sequence coding for a polypeptide of 10 kDa being the carboxy terminal part of a 34 kDa protein of *M. paratuberculosis*, defined hereafter.

An advantageous recombinant polypeptide of the invention is characterized by the fact that:

it contains the amino sequence of 101 amino acids of FIG. 8 (SEQ ID NO: 5) as its C-terminal part, it has a molecular weight of about 34 kDa, in SDS-PAGE, it is coded by a nucleotide sequence liable to hybridize with the complementary strand of the sequence of FIG. 11 (SEQ ID NO:2), it reacts with the majority of sera from cattle suffering from Johne's disease, it is advantageously liable to elicit a cellular immune response in sensitized subjects.

Subjects can be either test animals such as mice or guinea pigs or cattle or human beings.

"Sensitized" means that these subjects have been in contact previously with *M. paratuberculosis*, resulting in a priming of the cellular immune system.

Sensitization can be induced by inoculating the subjects with killed or attenuated *M. paratuberculosis* or it can result from a natural infection with *M. paratuberculosis*.

A positive cellular immune response to the polypeptides of the invention can be detected for example in vivo by a delayed—type hypersensitivity reaction upon skintesting with the polypeptides of the invention or in vitro by proliferation of peripheral blood lymphocytes isolated from sensitized subjects, in response to the added polypeptides.

An advantageous recombinant polypeptide of the invention contains or is constituted by the amino acid sequence of FIG. 11 (SEQ ID NO:11).

Another advantageous recombinant polypeptide of the invention contains or is constituted by the amino acid sequence extending from amino acid at position (1) to the amino acid at position (199), of FIG. 11 (SEQ ID NO:11).

It is to be noted that this polypeptide is a 34 kDa protein which is present in the proteic part of the TMA complex of *M. paratuberculosis* (A36).

Hereafter is given, in a non limitative way, a process for preparing this 34 kDa protein of the invention.

The DNA sequence (306 bp) coding for p362 (SEQ ID NO:4), being the carboxyterminal end of the 34 kDa protein has been determined (SEQ ID NO:5) (see FIG. 8). It contains a unique ApaI (GGGCCC) site at position 141.

Using this information, the full gene coding for the 34 kDa protein can be isolated as follows:

An oligonucleotide coding for a stretch of at least 30 bp, situated within the region EcoRI-ApaI (1–141 bp) of the known sequence, is synthesized.

It is labeled and used as a probe to hybridize to the DNA of *M. paratuberculosis* (strain ATCC 19698), which has previously been cut by ApaI, separated by agarose gel electrophoresis, denatured and transferred to a nylon membrane.

This hybridization indicates a band on the nylon membrane of around 1500 bp, which contains the coding part for the rest of the 34 kDa protein. After having located this 1500 bp fragment, flanked by 2 ApaI sites, in the agarose gel, it is isolated from the gel, purified and subcloned in the ApaI site of the sequencing vector pBluescript SK$^+$.

After sequencing of this fragment, the coding region, starting with the initiation codon ATG or GTG, is delineated. Using a restriction site near the initiation codon (5' end), naturally present or created by site-directed mutagenesis, and the ApaI site at the 3' end, the DNA fragment coding for the N-terminal part of the protein (about 750 bp) is excised from pBluescript SK$^+$, and purified. It is ligated to the ApaI site of the fragment coding for the C-terminal part of p362 (142–306, FIG. 8), that for example has been prepared synthetically.

The complete gene coding for the 34 kDa protein (about 910 bp) is subcloned in an expression vector and expressed in *E. coli*. The recombinant 34 kDa protein is then purified.

The invention also relates to the amino acid sequences constituted by the above mentioned polypeptides and a protein or an heterologous sequence with respect to said polypeptide, said protein or heterologous sequence comprising for instance from about 1 to about 1100 amino acids. These amino acid sequences will be called fusion proteins.

In an advantageous fusion protein of the invention, the heterologous protein is β-galactosidase.

The invention also relates to a nucleic acid characterized by the fact that it comprises or is constituted by:
- a nucleotide chain liable to hybridize with the nucleotide chain coding for the polypeptides according to the invention, or
- a nucleotide chain coding for the polypeptides according to the invention, or
- the complementary sequences of the above nucleotide chains.

The invention also relates to nucleic acids comprising nucleotide sequences which hybridize with the nucleotide sequences coding for any of the above mentioned polypeptides under the following hybridization conditions:
  hybridization and wash medium:
    a preferred hybridization medium contains about 3×SSC [SSC=0.15 M sodium chloride, 0.015 M sodium citrate, pH 7], about 25 mM of phosphate buffer pH 7.1, and 20% deionized formamide, 0.02% Ficoll, 0.02% BSA, 0.02% polyvinylpyrrolidone and about 0.1 mg/ml sheared denatured salmon sperm DNA,
    a preferred wash medium contains about 3×SSC, about 25 mM phosphate buffer, pH 7.1 and 20% deionized formamide;
  hybridization temperature (HT) and wash temperature (WT) for the nucleic acids of the invention defined by x-y: i.e. by the sequence extending from the extremity constituted by the nucleotide at position (x) to the extremity constituted by the nucleotide at position (y) represented on FIGS. 7A (SEQ ID NO:1), 7B (SEQ ID NO:2) or 7C (SEQ ID NO:3):
1–306 (for FIGS. 7B (SEQ ID NO:16) and 7c (SEQ ID NO:17)) or
HT=WT=65° C.
1–307 (for FIG. 7A (SEQ ID NO:14))
1–507 (for FIGS. 7B (SEQ ID NO:2) and 7c (SEQ ID NO:3))
HT=WT=65° C.
1–508 (for FIG. 7A (SEQ ID NO:1))

The above mentioned temperatures are to be considered as approximately ±5° C.

It is to be noted that in the above defined nucleic acids, as well as in the hereafter defined nucleic acids, the nucleotide sequences which are brought into play are such that T can be replaced by U.

A group of preferred nucleic acids of the invention comprises one at least of the following nucleotide sequences:
  the one extending from the extremity constituted by nucleotide at position (1) to the extremity constituted by nucleotide at position (307) (SEQ ID NO:14) represented in FIG. 7A,
  the one extending from the extremity constituted by nucleotide at position (1) to the extremity constituted by nucleotide at position (508) (SEQ ID NO:1) represented in FIG. 7A, wherein X and E represent phosphodiester bonds,
Y and F represent respectively G and C,
Z and H represent respectively C and G, or
X and E represent respectively G and C,
Y and F represent respectively C and G,
Z and H represent phosphodiester bonds.

A group of preferred nucleic acids of the invention comprises one at least of the following nucleotide sequences:
  the one extending from the extremity constituted by nucleotide at position (1) to the extremity constituted by nucleotide at position (306) (SEQ ID NO:15) represented in FIG. 7B,
  the one extending from the extremity constituted by nucleotide at position (1) to the extremity constituted by nucleotide at position (507) represented in FIG. 7B (SEQ ID NO:2).

The nucleotide sequence represented in FIG. 7B corresponds to the one represented in FIG. 7A, wherein
X and E represent phosphodiester bonds,
Y and F represent respectively G and C,
Z and H represent respectively C and G.

The invention also relates to a nucleic acid characterized by the fact that it comprises or is constituted by a nucleotide chain,
  extending from the extremity constituted by nucleotide at position (1) to the extremity constituted by nucleotide at position (306) (SEQ ID NO:16) on FIG. 7C, or
  extending from the extremity constituted by nucleotide at position (1) to the extremity constituted by nucleotide at position (507) (SEQ ID NO:3) on FIG. 7C.

The nucleotide sequence represented on FIG. 7C corresponds to the one represented on FIG. 7A, wherein
X and E represent respectively G and C,
Y and F represent respectively C and G,
Z and H represent phosphodiester bonds.

The invention also relates to a nucleic acid which comprises or is constituted by:
  a nucleotide sequence liable to hybridize with the complementary strand of the nucleotide sequence of FIG. 11 (SEQ ID NO:10), or with the complementary strand of the nucleotide sequence extending from nucleotide at position (742) to nucleotide at position (1338) (SEQ ID NO:17) of FIG. 11,
  the nucleotide sequence of FIG. 11 or the nucleotide sequence extending from nucleotide at position (742) to nucleotide at position (1338) (SEQ ID NO:17) of FIG. 11,
  the complementary sequences of the nucleotide sequences above-defined.

From the nucleic acids of the invention, probes (i.e. cloned or synthetic oligonucleotides) can be inferred.

These probes can be from 15 to the maximum number of nucleotides of the selected nucleic acids. The oligonucleotides can also be used either as amplification primers in the PCR technique (PCR, Mullis and Faloona, Methods in Enzymology, vol. 155, p. 335, 1987) to generate specific enzymatically amplified fragments and/or as probes to detect fragments amplified between bracketing oligonucleotide primers.

The specificity of a PCR-assisted hybridization assay can be controlled at different levels.

The amplification process or the detection process or both can be specific. The latter case giving the higher specificity is preferred.

The invention also relates to any recombinant nucleic acid containing at least one of the nucleic acids of the invention combined to or inserted in a heterologous nucleic acid.

The invention relates more particularly to recombinant nucleic acid such as defined, in which the nucleotide sequence of the invention is preceded by a promoter (particularly an inducible promoter) under the control of which the transcription of said sequence is liable to be processed and possibly followed by a sequence coding for transcription termination signals.

The invention also relates to the recombinant nucleic acids in which the nucleic acid sequences coding for the polypeptide of the invention and possibly the signal peptide, are recombined with control elements which are heterologous with respect to the ones to which they are normally associated with in the mycobacterial genome and, more particularly, the regulation elements adapted to control their expression in the cellular host which has been chosen for their production.

The invention also relates to recombinant vectors, particularly for cloning and/or expression, comprising a vector sequence, notably of the type plasmid, cosmid or phage or virus DNA, and a recombinant nucleic acid of the invention, inserted in one of the non essential sites for its replication.

According to an advantageous embodiment of the invention, the recombinant vector contains necessary elements to promote the expression in a cellular host of polypeptides coded by nucleic acids according to the invention inserted in said vector and notably a promoter recognized by the RNA polymerase of the cellular host, particularly an inducible promoter and possibly a sequence coding for transcription termination signals and possibly a signal sequence and/or an anchoring sequence.

According to another additional embodiment of the invention, the recombinant vector contains the elements enabling the expression by *E. coli* of a fusion protein consisting of the polypeptide of β-galactosidase or part thereof linked to a polypeptide coded by a nucleic acid according to the invention.

The invention also relates to a cellular host, chosen from among bacteria such as *E. coli* or chosen from among eukaryotic organism, such as CHO cells or insect cells, which is transformed by a recombinant vector according to the invention, and containing the regulation elements enabling the expression of the nucleotide sequence coding for the polypeptide according to the invention in this host.

The invention relates to an expression product of a nucleic acid expressed by a transformed cellular host according to the invention.

The invention also relates to a process for preparing a recombinant polypeptide according to the invention comprising the following steps:
- the culture in an appropriate medium of a cellular host which has previously been transformed by an appropriate vector containing a nucleic acid according to the invention,
- the recovery of the polypeptide produced by the above said transformed cellular host from the above said culture medium, or from the cellular host, and
- possibly the purification of the polypeptide produced, eventually by means of immobilized metal ion affinity chromatography (IMAC).

The polypeptides of the invention can be prepared according to the classical techniques in the field of peptide synthesis.

The synthesis can be carried out in homogeneous solution or in solid phase.

For instance, the synthesis technique in homogeneous solution which can be used is the one described by Houben-weyl in the book titled "Methode der organischen chemie" (Method of organic chemistry) edited by E. Wunsh, vol. 15-I et II. THIEME, Stuttgart 1974.

The polypeptides of the invention can also be prepared in solid phase according to the method described by Atherton & Shepard in their book titled "Solid phase peptide synthesis" (Ed. IRL Press, Oxford, NY, Tokyo, 1989).

The invention also relates to a process for preparing the nucleic acids according to the invention.

A suitable method for chemically preparing the single-stranded nucleic acids (containing at most 100 nucleotides of the invention) comprises the following steps:
- DNA synthesis using the automatic β-cyanoethyl phosphoramidite method described in Bioorganic Chemistry 4; 274–325, 1986.

In the case of single-stranded DNA, the material which is obtained at the end of the DNA synthesis can be used as such.

A suitable method for chemically preparing the double-stranded nucleic acids (containing at most 100 bp of the invention) comprises the following steps:
- DNA synthesis of one sense oligonucleotide using the automatic β-cyanoethyl phosphoramidite method described in Bioorganic Chemistry 4; 274–325, 1986, and DNA synthesis of one anti-sense oligonucleotide using said above-mentioned automatic β-cyanoethyl phosphoramidite method,
- combining the sense and anti-sense oligonucleotides by hybridization in order to form a DNA duplex,
- cloning the DNA duplex obtained into a suitable plasmid vector and recovery of the DNA according to classical methods, such as restriction enzyme digestion and agarose gel electrophoresis.

A method for the chemical preparation of nucleic acids of length greater than 100 nucleotides—or bp, in the case of double-stranded nucleic acids—comprises the following steps:
- assembling of chemically synthesized oligonucleotides, provided at their ends with different restriction sites, the sequences of which are compatible with the succession of amino acids in the natural peptide, according to the principle described in Proc. Nat. Acad. Sci. USA 80; 7461–7465, 1983,
- cloning the DNA thereby obtained into a suitable plasmid vetor and recovery of the desired nucleic acid according to classical methods, such as restriction enzyme digestion and agarose gel electrophoresis.

The invention also relates to antibodies themselves formed against the polypeptides according to the invention, and characterized by the fact that they recognize neither *M. bovis,* nor *M. avium,* nor *M. phlei,* nor *M. tuberculosis.*

It goes without saying that this production is not limited to polyclonal antibodies.

It also relates to any monoclonal antibody produced by any hybridoma liable to be formed according to classical methods from splenic cells of an animal, particularly of a mouse or rat, immunized against the purified polypeptide of the invention on the one hand, and of cells of a myeloma cell line on the other hand, and to be selected by its ability to produce the monoclonal antibodies recognizing the polypeptide which has been initially used for the immunization of the animals.

The invention also relates to any antibody of the invention labeled by an appropriate label of the enzymatic, fluorescent or radioactive type.

The polypeptide which is advantageously used to produce antibodies, particularly monoclonal antibodies, is the one or part of the one extending from the extremity constituted by amino acid at position (1) to the extremity constituted by amino acid at position (101) (SEQ ID NO:5) represented on FIG. 8.

Variations of this peptide are also possible depending on its intended use. For example, if the peptide is to be used to raise antisera, the peptide may be synthesized with an extra cysteine residue added. This extra cysteine residue is preferably added to the amino terminus and facilitates the coupling of the peptide to a carrier protein which is necessary to render the small peptide immunogenic. If the peptide is to be labeled for use in radioimmune assays, it may be advantageous to synthesize the protein with a tyrosine attached to either the amino or carboxyl terminus to facilitate iodination. This peptide possesses therefore the primary sequence of the peptide above-mentioned but with additional amino acids which do not appear in the primary sequence of the protein and whose sole function is to confer the desired chemical properties to the peptide.

The invention also relates to a process for detecting in vitro antibodies related to paratuberculosis in a biological sample of an animal liable to contain them, this process comprising contacting the biological sample with a polypeptide or a peptide according to the invention, or the expression product of the invention, under conditions enabling an in vitro immunological reaction between said polypeptide and the antibodies which are possibly present in the biological sample and the in vitro detection of the antigen/antibody complex which may be formed.

Preferably, the biological medium is constituted by an animal serum, and particularly by bovine serum.

The detection can be carried out according to any classical process.

By way of example a preferred method brings into play an immunoenzymatic process according to ELISA technique or immunofluorescent or radioimmunlogical (RIA) or the equivalent ones.

Thus the invention also relates to any polypeptide according to the invention labeled by an appropriate label of the enzymatic, fluorescent, radioactive . . . type.

Such a method for detecting in vitro antibodies related to paratuberculosis comprises for instance the following steps:

deposit of determined amounts of a polypeptidic composition according to the invention in the wells of a titration microplate, introduction into said wells of increasing dilutions of the serum to be diagnosed, incubation of the microplate, repeated rinsing of the microplate, introduction into the wells of the microplate of labeled antibodies against the blood immunoglobulins, the labeling of these antibodies being based on the activity of an enzyme which is selected from among the ones which are able to hydrolyze a substrate by modifying the absorption of the radiation of this latter at least at a given wave length, detection by comparing with a control standard of the amount of hydrolyzed substrate.

The invention also relates to a process for detecting and identifying in vitro antigens of *M. paratuberculosis* in an animal biological sample liable to contain them, this process comprising:

contacting the biological sample with an appropriate antibody of the invention under conditions enabling an in vitro immunological reaction between said antibody and the antigens of *M. paratuberculosis* which are possibly present in the biological sample and the in vitro detection of the antigen/antibody complex which may be formed.

Preferably, the biological medium is constituted by serum or faeces, milk or urine, particularly of bovine origin.

Appropriate antibodies are advantageously monoclonal antibodies directed against the above-mentioned peptide.

The invention also relates to an additional method for the in vitro diagnosis of paratuberculosis in an animal liable to be infected by *Mycobacterium paratuberculosis* comprising:

contacting a biological sample taken from an animal with a polypeptide or a peptide of the invention, or the expression product of the invention, under conditions enabling an in vitro immunological reaction between said polypeptide or peptide and the antibodies which are possibly present in the biological sample and the in vitro detection of the antigen/antibody complex which has possibly been formed.

To carry out the in vitro diagnostic method for paratuberculosis in an animal liable to be infected by *Mycobacterium paratuberculosis*, the following necessary or kit can be used, said necessary or kit comprising:

a polypeptide or a peptide according to the invention, or the expression product of the invention, reagents for making a medium appropriate for the immunological reaction to occur, reagents enabling to detect the antigen/antibody complex which has been produced by the immunological reaction, said reagents possibly having a label, or being liable to be recognized by a labeled reagent, more particularly in the case where the above mentioned polypeptide or peptide is not labeled.

The invention also relates to an additional method for the in vitro diagnosis of paratuberculosis in an animal liable to be infected by *M. paratuberculosis*, comprising the following steps:

contacting a biological sample of said animal with an appropriate antibody of the invention under conditions enabling an in vitro immunological reaction between said antibody and the antigens of *M. paratuberculosis* which are possibly present in the biological sample and the in vitro detection of the antigen/antibody complex which may be formed.

To carry out the in vitro diagnostic method for paratuberculosis in an animal liable to be infected by *Mycobacterium paratuberculosis*, the following necessary or kit can be used, said necessary or kit comprising:

an antibody of the invention, reagents for making a medium appropriate for the immunological reaction to occur, reagents enabling to detect the antigen/antibody complexes which have been produced by the immunological reaction, said reagent possibly having a label or being liable to be recognized by a labeled reagent, more particularly in the case where the above-mentioned antibody is not labeled.

An advantageous kit for the in vitro diagnosis of paratuberculosis comprises:

at least a suitable solid phase system, e.g. a microtiterplate for deposition thereon of the biological sample to be diagnosed in vitro, a preparation containing one of the monoclonal antibodies of the invention, a specific detection system for said monoclonal antibody, appropriate buffer solutions for carrying out the immunological reaction between a test sample and said monoclonal antibody on the one hand, and the bonded monoclonal antibodies and the detection system on the other hand.

The invention also relates to a kit, as described above, also containing a preparation of one of the polypeptides or peptides of the invention, said antigen of the invention being either a standard (for quantitative determination of the antigen of M. paratuberculosis which is sought) or a competitor, with respect to the antigen which is sought, for the kit to be used in a competition dosage process.

The invention also relates to a method for the in vitro diagnosis of Crohn's disease in a patient liable to be infected by Mycobacterium paratuberculosis comprising the following steps:

contacting the biological sample with an appropriate antibody according to the invention, under conditions enabling an in vitro immunological reaction between said antibody and the antigens of M. paratuberculosis which are possibly present in the biological sample and the in vitro detection of the antigen/antibody complex which may be formed.

The invention also relates to a method for the in vitro diagnosis of Crohn's disease in a patient liable to be infected by M. paratuberculosis, comprising the following steps:

contacting a biological sample taken from a patient with a polypeptide or peptide according to the invention, or the expression product of the invention, under conditions enabling an in vitro immunological reaction between said polypeptide and the antibodies which are possibly present in the biological sample and the in vitro detection of the antigen/antibody complex which has been possibly formed.

The invention also relates to a necessary or kit for an in vitro diagnosis method of Crohn's disease in a patient liable to be infected by Mycobacterium paratuberculosis, said necessary or kit comprising:

an antibody according to the invention, reagents for making a medium appropriate for the immunological reaction to occur, reagents enabling to detect the antigen/antibody complexes which have been produced by the immunological reaction, said reagents possibly having a label or being liable to be recognized by a labeled reagent, more particularly in the case where the above-mentioned antibody is not labeled.

The invention also relates to a necessary or kit for an in vitro diagnosis method of Crohn's disease in a patient liable to be infected by Mycobacterium paratuberculosis said necessary or kit comprising:

a polypeptide or a peptide according to the invention, or the expression product of the invention, reagents for making a medium appropriate for the immunological reaction to occur, reagents enabling to detect the antigen/antibody complex which has been produced by the immunological reaction, said reagents possibly having a label, or being liable to be recognized by a labeled reagent, more particularly in the case where the above mentioned polypeptide is not labeled.

The invention also relates to an immunogenic composition comprising a polypeptide or a peptide according to the invention, or the expression product of the invention, in association with a pharmaceutically acceptable vehicle.

The invention also relates, to a vaccine composition comprising among other immunogenic principles anyone of the polypeptides or peptides of the invention or the expression product of the invention, possibly coupled to a natural protein or to a synthetic polypeptide having a sufficient molecular weight so that the conjugate is able to induce in vivo the production of antibodies neutralizing Mycobacterium paratuberculosis, or induce in vivo a protective cellular immune response by activating M. paratuberculosis antigen-responsive T cells.

The invention also relates to a necessary or kit for the diagnosis of prior exposure of an animal to M. paratuberculosis, said necessary or kit containing a preparation of at least one of the polypeptides or peptides of the invention, or the expression product of the invention, with said preparation being able to induce in vivo after being intradermally injected to an animal a delayed type hypersensitivity reaction, at the site of injection, in case the animal has had prior exposure to M. paratuberculosis.

Other characteristics and advantages of the invention will appear in the following examples and the figures illustrating the invention.

LEGENDS TO FIGURES

FIG. 1 (1) represents the two-dimensional cross immunoelectrophoresis (CIE) of total cytoplasm (the supernatant fraction obtained after centrifugation of the sonicate) from M. paratuberculosis and FIG. 1(2) represents the two-dimensional cross immunoelectrophoresis of the exclusion fraction obtained by gel exclusion chromatography of the same cytoplasm.

In the second dimension (upward in the figure), migration was made in a gel containing rabbit antiserum directed against the mycobacterial sonicate. Preparations in 1 and 2 contained 10 μg of proteins. This figure identifies the TMA complex of M. paratuberculosis (A36) present in the exclusion fraction.

FIG. 2 represents the serological analysis of infected animals with polypeptide p362. Multiwell plates were coated with 4 μg of proteins/well of E. coli-a362 total cytoplasm (white) or E. coli-control total cytoplasm (black). Samples of diluted (1/400) bovine sera previously exhausted by incubation with E. coli-control homogenate (said homogenate and total cytoplasm being obtained in the same way as M. paratuberculosis homogenate and total cytoplasm as described above) were added, followed by washing, incubation with labeled anti-bovine Ig, peroxidase reagents and spectrophotometric reading at 450 nm.

The following sera were used: asymptomatic non-excretory (sample 1), asymptomatic excretory (samples 2 to 13), symptomatic excretory (samples 14 to 24) and healthy bovine (samples 26 to 32).

FIG. 3 represents the serological analysis of infected animals with a A36-based immunoassay.

Multiwell plates were coated with comparable amounts (0.5 μg total proteins/well) of: M. paratuberculosis total cytoplasm (black), A36 (white) and B. subtilis total cytoplasm (control: hatched). Samples of diluted (1/400) bovine sera previously exhausted by incubation with B. subtilis homogenate (said homogenate and total cytoplasm being obtained in the same way as M. paratuberculosis homogenate and total cytoplasm as above-described) were added, followed by washing, incubation with labeled anti-bovine Ig, peroxidase reagents and spectrophotometric reading at 450 nm. The following bovine sera were used:

a) symptomatic-excretory forms of paratuberculosis (samples 1 to 7); b) asymptomatic-excretory forms (samples 8 to 12); and c) healthy cattle (samples 13 to 15). Mean values of absorbance and standard deviations are the results of 4 repeats.

FIG. 4 represents the recognition of different A36 proteins by the sera of infected bovines. A36 proteins from *M. paratuberculosis* were fractionated by gel electrophoresis and transferred to nitrocellulose. Membranes were incubated with sera from uninfected (lane 8) or infected animals (lanes 4 to 7), either pre-absorbed (lane 7) or not (lanes 4, 5, 6) with a mixture of homogenates of *M. avium, M. bovis* and *M. phlei*. Membrane-bound primary Ig were revealed by labeled secondary Ig. Sera of infected animals were as follows: asymptomatic-non excretory (lane 4), asymptomatic-excretory (lane 5), and symptomatic-excretory (lane 6, 7) cases of paratuberculosis. Reference molecular weight standards (lane 1) and A36 proteins (lane 2) were stained by India ink. Reference: A36 proteins immunoblotted with anti-A36 rabbit antiserum (lane 3).

FIG. 5 represents the analysis of the size of the polypeptide (p362) fused to β-galactosidase expressed by recombinant clone a362 (hereafter defined). This fusion protein is named βgal-p362.

Lysate proteins of *E. coli* Y1089 lysogenized either by standard λgt11 (tracks C and E) or by the same phage carrying the insert coding for p362 (clone a362) (tracks D and F) were fractionated by 7.5% polyacrylamide gel electrophoresis. Tracks C and D and molecular weight standards (tracks A and B) were stained with Coomassie brilliant blue, whereas tracks E and F were treated with rabbit anti-A36 antiserum and stained with peroxydase-labeled anti-rabbit antiserum.

FIG. 6 represents the evidence of the belonging of the recombinant polypeptide p362 to the 34 kD protein of the A36 complex.

The TMA complex from *M. paratuberculosis* was dissociated and its protein components were fractionated by 10% polyacrylamide gel electrophoresis and transblotted to a nitrocellulose membrane. Fractionated proteins were either stained with India ink (track b) or incubated with rabbit anti-βgal-p362 antiserum (track c). Track a: molecular weight standards.

FIG. 7A (SEQ ID NO:1) represents the nucleic acid sequence encompassing the nucleic acid sequence of FIG. 7B and the one of FIG. 7C.

FIG. 7B (SEQ ID NO:2) represents a sequence homologous to the one represented on FIG. 7C.

FIG. 7C (SEQ ID NO:3) represents the base sequence of the *M. paratuberculosis* genomic fragment present in clone a362 and coding for p362.

It should be noted that the two EcoRI sites [GAATTC] present at both ends of the sequence are a result of the cloning strategy and are not naturally present in the genomic sequence.

FIG. 8 (SEQ ID NO:5) represents the amino acid sequence and corresponding nucleotide sequence (SEQ ID NO:4) of the recombinant polypeptide p362.

It should be noted that the first two amino acids, corresponding to the EcoRI sites in the DNA sequence, are not naturally present in the native protein, but are a result of cloning.

Figure 9A:
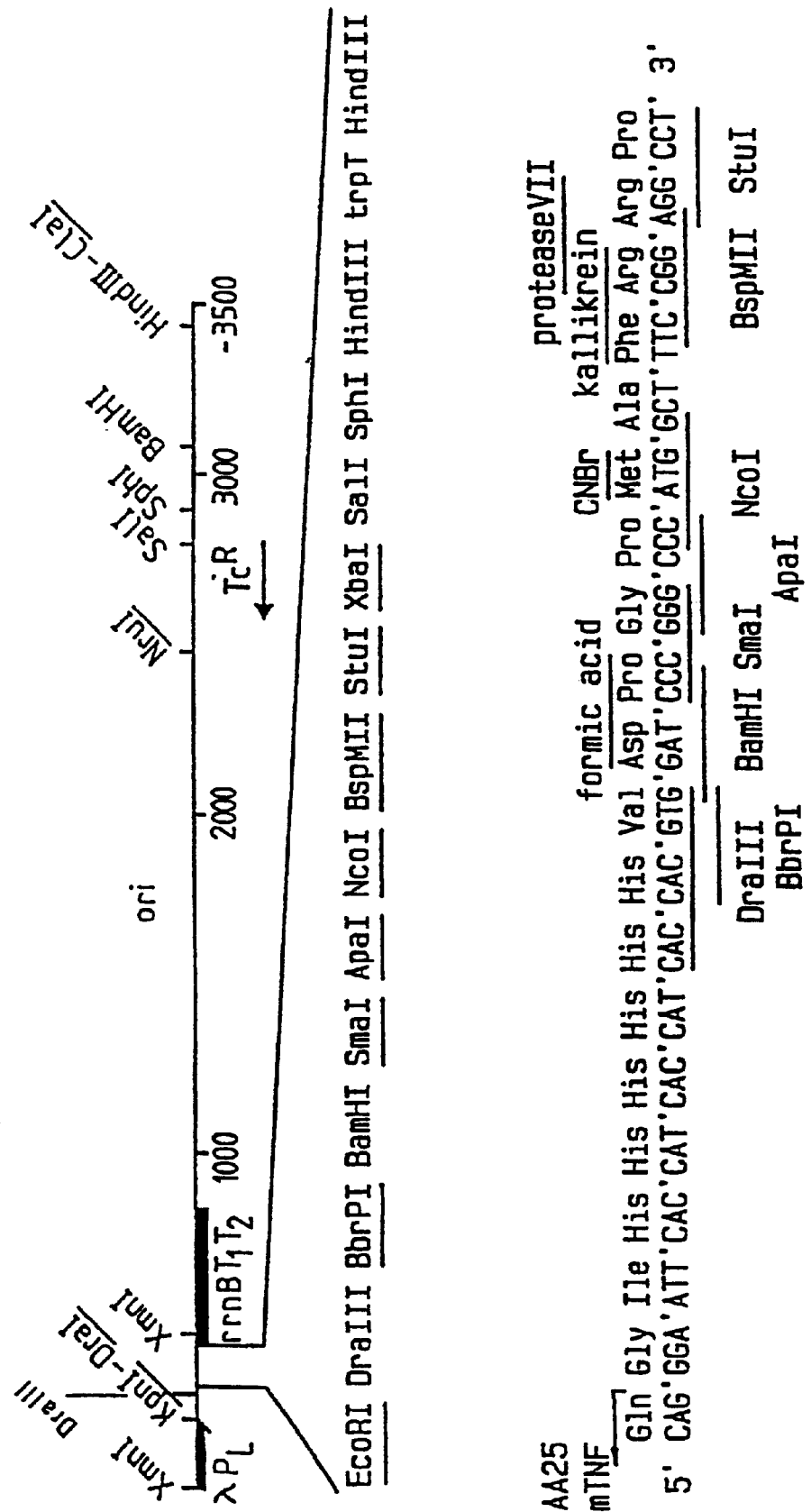

FIG. 9a (SEQ ID NO:6 and SEQ ID NO:7) corresponds to the restriction and genetic map of the pmTNF-MPH plasmid used in Example II for the expression of p362 of the invention in *E. coli*.

FIG. 9b (SEQ ID NO:8) corresponds to the pmTNF-MPH nucleic acid sequence.

On this figure, the origin of nucleotide stretches used to construct plasmid pmTNF-MPH is specified hereafter. Position 1–208: lambda PL containing EcoRI blunt-MboII blunt fragment of pPL(λ) (Pharmacia)
209–436: synthetic DNA fragment
230–232: initiation codon (ATG) of mTNF fusion protein
236–307: sequence encoding AA 2 to 25 of mature mouse TNF
308–384: multiple cloning site containing $His_6$ encoding sequence at position 315–332
385–436: HindIII fragment containing *E. coli* trp terminator
437–943: $rrnBT_1T_2$ containing HindIII-SspI fragment from pKK223 (Pharmacia)
944–3474: DraI-EcoRI blunt fragment of $pAT_{153}$ (Bioexcellence) containing the tetracycline resistance gene and the origin of replication.

FIG. 10 (SEQ ID NO:9) represents the complete amino acid sequence of the recombinant polypeptide mTNF-H6-p362. The amino acids 1–26 represent the mTNF part, the amino acids from 27–46 correspond to the polylinker part (H6) and the remaining amino acids (47–147) represent the *M. paratuberculosis* 10 kDa polypeptide (p362).

FIG. 11 represents the DNA sequence (SEQ ID NO:10) containing the nucleic acid coding for the protein of 34 kDa hereabove defined and the corresponding amino acid sequence (SEQ ID NO:11). Nucleotides are numbered in the right-hand side margin and amino acids are numbered below the protein sequence.

It is to be noted that the arrow before amino acid 200 corresponds to the third amino acid of FIG. 8, since the first two amino acids of FIG. 8 are artficial, corresponding to the EcoRI site from cloning.

Table 5 hereafter corresponds to the complete restriction site analysis of pmTNF-MPH.

TABLE 5

RESTRICTION-SITE ANALYSIS

Done on DNA sequence PMTNFMPH.
Total number of bases is: 3474.
Analysis done on the complete sequence.

List of cuts by enzyme.

| | | | | | | | | | |
|---|---|---|---|---|---|---|---|---|---|
| Acc I: | 371 | 2818 | | | | | | | |
| Acy I: | 788 | 2264 | 2921 | 3035 | 3056 | | | | |
| Afl II: | 387 | | | | | | | | |
| Afl III: | 1698 | | | | | | | | |
| Aha III: | 224 | | | | | | | | |
| Alu I: | 386 | 439 | 1141 | 1398 | 1534 | 1760 | 2382 | 2785 | 3441 | 3456 |

TABLE 5-continued

RESTRICTION-SITE ANALYSIS

| | | | | | | | | | | |
|---|---|---|---|---|---|---|---|---|---|---|
| Alw NI: | 1289 | | | | | | | | | |
| Apa I: | 345 | | | | | | | | | |
| Apa LI: | 1384 | | | | | | | | | |
| Asp 718I: | 210 | | | | | | | | | |
| Asu I: | 341 | 342 | 547 | 676 | 766 | 1988 | 2030 | 2209 | 2333 | 2582 | 267 |
| | 2945 | 3297 | | | | | | | | |
| Ava I: | 338 | 2043 | | | | | | | | |
| Ava II: | 547 | 1988 | 2030 | 2333 | 2582 | 2670 | | | | |
| Bal I: | 2026 | | | | | | | | | |
| Bam BI: | 334 | 3093 | | | | | | | | |
| Bbe I: | 2267 | 2924 | 3038 | 3059 | | | | | | |
| Bbv I: | 1369 | 1788 | 1806 | 1919 | 1922 | 2866 | 3255 | | | |
| Bbv I*: | 1070 | 1276 | 1279 | 2026 | 2050 | 2683 | | | | |
| Bbv II: | 1875 | 2738 | | | | | | | | |
| Bgl I: | 2306 | 2540 | | | | | | | | |
| Bin I: | 17 | 342 | 956 | 1054 | 1140 | 3101 | | | | |
| Bin I*: | 329 | 955 | 1052 | 2366 | 3088 | | | | | |
| Bsp III: | 908 | 978 | 2979 | | | | | | | |
| Bsp HI: | 2414 | | | | | | | | | |
| Bsp HII: | 354 | | | | | | | | | |
| Bst NI: | 215 | 528 | 638 | 806 | 1539 | 1552 | 1673 | 2028 | 2411 | 3340 | |
| Cau II: | 6 | 339 | 340 | 736 | 769 | 1321 | 1986 | 2212 | 2936 | 3300 | |
| Cfr 10I: | 374 | 2185 | 2539 | 2699 | 3058 | 3067 | 3308 | | | | |
| Cfr I: | 2024 | 2529 | 2937 | 3069 | 3173 | | | | | | |
| Cla I: | 3446 | | | | | | | | | | |
| Cvi JI: | 192 | 265 | 272 | 343 | 350 | 361 | 386 | 400 | 439 | 444 | 47 |
| | 660 | 678 | 767 | 828 | 844 | 1141 | 1170 | 1213 | 1224 | 1289 | 136 |
| | 1393 | 1398 | 1534 | 1632 | 1658 | 1676 | 1687 | 1760 | 1779 | 1979 | 198 |
| | 2026 | 2063 | 2145 | 2189 | 2210 | 2215 | 2353 | 2363 | 2382 | 2423 | 248 |
| | 2488 | 2518 | 2531 | 2552 | 2597 | 2641 | 2785 | 2801 | 2857 | 2875 | 293 |
| | 2947 | 2985 | 2999 | 3071 | 3140 | 3175 | 3298 | 3322 | 3441 | 3456 | |
| Cvi QI: | 211 | 3306 | | | | | | | | | |
| Dde I: | 135 | 571 | 661 | 717 | 1015 | 1424 | 1888 | | | | |
| Dpn I: | 11 | 238 | 336 | 950 | 962 | 1040 | 1048 | 1059 | 1134 | 2010 | 232 |
| | 2342 | 2373 | 2645 | 3004 | 3095 | 3122 | | | | | |
| Dra II: | 1988 | 2030 | 2945 | | | | | | | | |
| Dra III: | 295 | 331 | | | | | | | | | |
| Dsa I: | 345 | 2021 | 2940 | | | | | | | | |
| Eco 31I: | 615 | | | | | | | | | | |
| Eco 47III: | 1826 | 2695 | 2976 | 3238 | | | | | | | |
| Eco 57I: | 216 | | | | | | | | | | |
| Eco 57I*: | 1156 | | | | | | | | | | |
| Eco 78I: | 2265 | 2922 | 3036 | 3057 | | | | | | | |
| Eco NI: | 198 | 2845 | | | | | | | | | |
| Eco RI: | 309 | | | | | | | | | | |
| Eco RII: | 213 | 526 | 636 | 804 | 1537 | 1550 | 1671 | 2026 | 2409 | 3338 | |
| Eco RV: | 3285 | | | | | | | | | | |
| Fnu 4HI: | 401 | 417 | 532 | 1084 | 1290 | 1293 | 1358 | 1501 | 1656 | 1774 | 177 |
| | 1795 | 1908 | 1911 | 2040 | 2054 | 2061 | 2064 | 2183 | 2262 | 2307 | 236 |
| | 2447 | 2532 | 2697 | 2748 | 2855 | 2889 | 2892 | 3170 | 3173 | 3244 | |
| Fnu DII: | 542 | 1074 | 1655 | 1837 | 1934 | 2056 | 2082 | 2227 | 2237 | 2366 | 243 |
| | 2493 | 2498 | 2525 | 2654 | 2769 | 3125 | | | | | |
| Fok I: | 468 | 852 | 3370 | | | | | | | | |
| Fok I*: | 816 | 2423 | 2468 | 3322 | | | | | | | |
| Gsu I: | 2088 | | | | | | | | | | |
| Gsu I*: | 2642 | | | | | | | | | | |
| Hae I: | 361 | 828 | 844 | 1224 | 1676 | 1687 | 2026 | 2423 | 2480 | 2552 | |
| Hae II: | 594 | 1458 | 1828 | 2267 | 2697 | 2924 | 2978 | 3038 | 3059 | 3240 | |
| Hae III: | 343 | 361 | 678 | 767 | 828 | 844 | 1224 | 1658 | 1676 | 1687 | 202 |
| | 2210 | 2423 | 2480 | 2531 | 2552 | 2641 | 2875 | 2939 | 2947 | 3071 | 317 |
| | 3298 | | | | | | | | | | |
| Hga I: | 160 | 183 | 796 | 2088 | 2238 | 2829 | | | | | |
| Hga I*: | 1008 | 1586 | 2482 | 2514 | 3068 | | | | | | |
| Hgi AI: | 141 | 1388 | 2007 | 2298 | 2885 | 3196 | | | | | |
| Hgi CI: | 210 | 2179 | 2263 | 2702 | 2920 | 3034 | 3055 | 3349 | 3392 | | |
| Hgi JII: | 345 | 2987 | 3001 | | | | | | | | |
| Hha I: | 542 | 593 | 1074 | 1183 | 1357 | 1457 | 1524 | 1794 | 1827 | 2017 | 205 |
| | 2115 | 2266 | 2525 | 2656 | 2696 | 2771 | 2923 | 2977 | 3037 | 3058 | 321 |
| | 3239 | 3371 | | | | | | | | | |
| Hin P1I: | 540 | 591 | 1072 | 1181 | 1355 | 1455 | 1522 | 1792 | 1825 | 2015 | 205 |
| | 2113 | 2264 | 2523 | 2654 | 2694 | 2769 | 2921 | 2975 | 3035 | 3056 | 320 |
| | 3237 | 3369 | | | | | | | | | |
| Hind II: | 109 | 372 | 2819 | | | | | | | | |
| Hind III: | 384 | 437 | 3439 | | | | | | | | |
| Hinf I: | 368 | 1328 | 1724 | 1799 | 1944 | 2165 | 2463 | 2617 | 2837 | | |
| Hpa II: | 5 | 339 | 355 | 375 | 735 | 769 | 1130 | 1320 | 1346 | 1493 | 198 |
| | 2186 | 2212 | 2450 | 2540 | 2700 | 2776 | 2936 | 3059 | 3068 | 3083 | 330 |

TABLE 5-continued

RESTRICTION-SITE ANALYSIS

| Enzyme | | | | | | | | | | |
|---|---|---|---|---|---|---|---|---|---|---|
| | 3309 | | | | | | | | | |
| Hph I: | 96 | 140 | 183 | 716 | 967 | 1953 | 2174 | 3028 | 3073 | 3355 |
| Hph I*: | 8 | 305 | 311 | 317 | | | | | | |
| Kpn I: | 214 | | | | | | | | | |
| Mae I: | 365 | 952 | 1205 | 1981 | 3240 | | | | | |
| Mae II: | 276 | 330 | 751 | 997 | 1900 | 1924 | 2513 | 2569 | | |
| Mae III: | 171 | 257 | 1162 | 1278 | 1341 | 2320 | 2587 | 3255 | 3343 | |
| Mbo I: | 9 | 236 | 334 | 948 | 960 | 1038 | 1046 | 1057 | 1132 | 2008 | 232 |
| | 2340 | 2371 | 2643 | 3002 | 3093 | 3120 | | | | |
| Mbo II: | 209 | 475 | 970 | 1832 | 1880 | 2472 | 2743 | | | |
| Mbo II*: | 1041 | 2997 | | | | | | | | |
| Mme I*: | 1305 | 1489 | 3165 | 3252 | | | | | | |
| Mnl I: | 372 | 1271 | 1595 | 2001 | 2499 | 2683 | | | | |
| Mnl I*: | 210 | 291 | 350 | 764 | 1520 | 1803 | 2169 | 2196 | 2234 | 2295 | 259 |
| Mse I: | 181 | 188 | 223 | 388 | 486 | 817 | 994 | 3414 | 3436 | |
| Mst I: | 2016 | 2114 | 3210 | | | | | | | |
| Nae I: | 2187 | 2541 | 2701 | 3069 | | | | | | |
| Nar I: | 2264 | 2921 | 3035 | 3056 | | | | | | |
| Nco I: | 345 | | | | | | | | | |
| Nhe I: | 3239 | | | | | | | | | |
| Nla III: | 168 | 232 | 349 | 382 | 565 | 620 | 912 | 982 | 1702 | 1881 | 201 |
| | 2222 | 2279 | 2294 | 2422 | 2539 | 2725 | 2764 | 2910 | 2983 | 3121 | 346 |
| Nla IV: | 212 | 336 | 343 | 549 | 1631 | 1670 | 1989 | 2032 | 2146 | 2181 | 221 |
| | 2265 | 2583 | 2704 | 2922 | 2946 | 3036 | 3057 | 3095 | 3141 | 3351 | 339 |
| Nru I: | 2498 | | | | | | | | | |
| Nsp BII: | 412 | 1115 | 1360 | 2331 | | | | | | |
| Nsp HI: | 382 | 1702 | 2910 | | | | | | | |
| Pfl MI: | 295 | 2105 | 2154 | | | | | | | |
| Ple I: | 376 | 1807 | | | | | | | | |
| Ple I*: | 1322 | 2831 | | | | | | | | |
| Pma CI: | 331 | | | | | | | | | |
| Ppu MI: | 1988 | 2030 | | | | | | | | |
| Pss I: | 1991 | 2033 | 2948 | | | | | | | |
| Rsa I: | 212 | 3307 | | | | | | | | |
| Sal I: | 370 | 2817 | | | | | | | | |
| Scr PI: | 6 | 215 | 339 | 340 | 528 | 638 | 736 | 769 | 806 | 1321 | 153 |
| | 1552 | 1673 | 1986 | 2028 | 2212 | 2411 | 2936 | 3300 | 3340 | |
| Sdu I: | 141 | 345 | 1388 | 2007 | 2298 | 2885 | 2987 | 3001 | 3196 | |
| Sec I: | 5 | 338 | 345 | 1538 | 2021 | 2099 | 2301 | 2934 | 2940 | 3339 | 335 |
| Sfa NI: | 650 | 818 | 2445 | 2820 | 3231 | 3344 | | | | |
| Sfa NI*: | 420 | 1601 | 2038 | 2433 | 3054 | 3066 | 3255 | | | |
| Sma I: | 340 | | | | | | | | | |
| Sph I: | 382 | 2910 | | | | | | | | |
| Sso II: | 4 | 213 | 337 | 338 | 526 | 636 | 734 | 767 | 804 | 1319 | 153 |
| | 1550 | 1671 | 1984 | 2026 | 2210 | 2409 | 2934 | 3298 | 3338 | |
| Stu I: | 361 | | | | | | | | | |
| Sty I: | 345 | 2099 | | | | | | | | |
| Taq I: | 254 | 371 | 666 | 1600 | 2202 | 2343 | 2818 | 3131 | 3446 | |
| Taq IIB: | 1802 | | | | | | | | | |
| Taq IIB*: | 2804 | | | | | | | | | |
| Tth111II: | 40 | 1107 | | | | | | | | |
| Tth111II*: | 686 | 1075 | 1114 | | | | | | | |
| Xba I: | 364 | | | | | | | | | |
| Xho II: | 9 | 334 | 948 | 960 | 1046 | 1057 | 3093 | | | |
| Xma I: | 338 | | | | | | | | | |
| Xma III: | 2529 | | | | | | | | | |
| Xmn I: | 467 | | | | | | | | | |

Total number of cuts is: 743.

List of non cutting selected enzymes.

| | | | | | | | |
|---|---|---|---|---|---|---|---|
| Aat II, | Asu II, | Avr II, | Bbv II*, | Bcl I, | Bgl II, | | Bsp MI* |
| Bss HII, | Bst EII, | Bst XI, | Eco 31I*, | Esp I, | Hpa I, | | Mlu I |
| Mme I, | Nde I, | Not I, | Nsi I, | Pst I, | Pvu I, | | Pvu II |
| Rsr II, | Sac I, | Sac II, | Sau I, | Sca I, | Sci I, | | Sfi I |
| Sna BI, | Spe I, | Spl I, | Ssp I, | Taq IIA, | Taq IIA*, | | Tth 111I |
| Vsp I, | Xca I, | Xho I | | | | | |

Total number of selected enzymes which do not cut: 38

EXAMPLE I

Purification of the TMA Complex of *M. paratuberculosis* (A36), Characterization of the Proteic Part of A36, Identification of the 34 kDa Protein and Development of A36 Based Immunoassay Materials and Methods Bacteria:

The following mycobacteria were used: *M. paratuberculosis* strain 2E and 316F (from Dr. F. Saxegaard, National Veterinary Institute, Oslo, Norway; Saregaard F. et al., 1985, "Control of paratuberculosis (Johne's disease) in goats by vaccination" 116:439–441); *M. avium* serotype 4 (from Dr. F. Portaels, Institute of Tropical Medicine, Antwerpen, Belgium) (Shaefer W. B., 1965, "Serologic identification and classification of the atypical mycobacteria by their agglutination", Am. Rev. Resp. Dis. suppl. 92:85–93); *M. bovis* strain BCG GL2 (from Dr. Weckx, Pasteur Institute, Brussels, Belgium) and *M. phlei* strain AM76 (from Dr. M. Desmecht, National Institute for Veterinary Research, Brussels, Belgium). The 168 strain of *B. subtilis* was used as control ATCC no 33234.

Preparation of bacterial cytoplasms:

Bacterial suspensions in buffered saline (100 mg wet weight cells/ml 0.15 N NaCl 0.02 M $K_2HPO_4$ pH 7.5 containing 10 mM phenylmethylsulfonyl fluoride) were disrupted by sonication (15 min treatment with a 500-W ultrasonic processor, Vibra cell from Sonics and Materials Inc, Danbury, Conn. USA (3 min sonication for *B. subtilis*). Homogenates were centrifuged (5000×g, 10 min, 4° C.), and supernatants (i.e. mycobacterial cytoplasms) were stored at −20° C. and used as sources of antigens.

Purification of TMA complexes:

The supernatant (about 4.5 mg proteins/ml) was submitted to RNAase digestion (10 µg enzyme/100 g wet weight bacteria, 30 min, 37° C.) and fractionated by gel exclusion chromatography on Sepharose 6B columns (Pharmacia, Uppsala, Sweden) equilibrated with buffered saline, as previously detailed (Cocito C. et al., 1986, "Preparation and properties of antigen 60 from *Mycobacterium bovis* BCG" Clin. Exp. Immunol. 66:262–272). TMA complexes (thermostable macromolecular antigen complexes) were found within the excluded fractions (which contained on the average 0.5 mg soluble proteins/ml). Solutions of TMA (with 1 mM phenylmethylsulfonyl fluoride as conservative) were stored at −20° C.

Purity of TmA complexes was checked by crossed immunoelectrophoresis, according to the reference systems (Closs O. et al., 1980, "The antigens of *Mycobacterium bovis*, strain BCG, studied by crossed immunoelectrophoresis: a reference system" Scand. J. Immunol. 12:249–263; Gunnarsson E. et al., 1979, "Analysis of antigens in *Mycobacterium paratuberculosis*" Acta Vet. Scand. 20:200–215).

For this purpose agarose gels (1% type 2 agarose from Sigma, St Louis, Mo.) on glass plates (5 by 7 cm) were used, the top gel containing 200 µl of rabbit anti-mycobacterial homogenate. Mycobacterial antigen (10 µl of samples containing 0.5 mg TMA/ml) was applied to a corner well and electrophoretic runs were made as described (1 h, 8 V/cm, 15° C. in 1st dimension; 3 V/cm, 18 h, 15° C. in 2nd dimension). Slants were washed, dried, stained with Coomassie blue and photographed.

Animal sera:

For production of polyclonal antisera, mycobacterial homogenate or TMA preparations (10 µg soluble proteins/ 0.5 ml buffered saline emulsified with equal volume of incomplete Freund adjuvant) were repeatedly injected (6 inoculations at 1-week intervals) into rabbits by subcutaneous way.

The antibody titer of the sera was evaluated by an immunoenzymometric procedure (see below).

Here is thus obtained a polyclonal anti-TMA complex antiserum, more particularly anti-A36 antiserum, and a polyclonal anti-homogenate antiserum referred to in the Western blotting test.

Four kinds of sera from bovines either healthy or at different stages of the Johne's disease were used:
a) healthy controls with no sign of mycobacterial infection and with negative tests of coproculture and complement fixation; b) asymptomatic non-excretory stage I of the disease (a case which appeared negative at the moment of sampling but became positive later);
c) asymptomatic excretory stage II of the disease (positive coproculture with no clinical signs of disease); and d) symptomatic excretory stage III of the disease (with positive complement fixation test). These sera were provided by the National Institute of Veterinary Research (Dr. M. Desmecht, Brussels, Belgium) and the Center of Veterinary Medicine (Dr. B. Limbourg, Erpent, Belgium).

Electrophoretic fractionation and Western blotting of TMA proteins:

The protein moiety of TMA complexes was fractionated by electrophoresis on 10% polyacrylamide gels, in the presence of Na dodecyl sulfate (SDS-PAGE procedure) (Laemmli U. K., 1970, "Cleavage of structural proteins during the assembly of the head of bacteriophage T4" Nature 227:680–695). Protein samples (25 µg soluble polypeptides in 50 µl 0.125 mM Tris-HCl pH 6.8 containing 5% w/v SDS, 20% v/v glycerol, 10% V:V β-mercaptoethanol and 0.05% bromophenol blue) were boiled for 5 min and then applied to vertical gel slabs. Molecular weight protein markers (Sigma Chem. Co., St Louis, Mo.) were: bovine serum albumin (66 kDa), ovalbumin (45 kDa), glyceraldehyde-3-phosphate dehydrogenase (36 kDa), carbonic anhydrase (29 kDa), trypsinogen (24 kDa), trypsin inhibitor (20.1 kDa) and α-lactalbumin (14.2 kDa). Electrophoretic runs (4 h, 50 V, 20° C.) were made in a vertical unit (LKB, Bromma, Sweden). Protein bands were visualized by staining with coomassie brilliant blue. Controls of total cytoplasmic proteins were run in parallel with TMA samples.

Electrophoresed proteins were transferred from polyacrylamide gels to nitrocellulose membranes (BA 85, Macherey-Nagel, Germany) by the use of a transblot-unit (217 multiphor 2, LKB, Bramma, Sweden).

Transfer buffer contained 20% methanol, 0.039 M glycine and 0.048 M Tris base pH 8.8, and runs were made at 10 V for 2 h. Transblotted proteins were identified by reaction with a primary antibody (either polyclonal rabbit antiserum [1/1500] or bovine serum [1/1001]) and then with a labeled secondary antibody.

Transblotted nitrocellulose sheets were first incubated for 30 min with TBS buffer (0.5 M NaCl, 0.023 M Tris-HCl pH 7.5) containing 3% w/v gelatin and then for 3 h with the primary antibodies diluted with TBST buffer (TBS containing 0.05% v/v Tween 20) and 1% w/v gelatin. After repeated washings with TBST, sheets were incubated for 2 h with secondary IgG (1/400 diluted preparations of peroxydase-labeled anti-rabbit, or anti-mouse or anti-cow IgG, Dako, Copenhagen, Denmark), followed by washings with TBST and TBS buffers. A color reaction was developed by addition of α-chloronaphtol (Bio-Rad Laboratories, Richmond, Calif.) in the presence of hydrogen peroxide. The color reaction was stopped by washing sheets with distilled water. A similar protocol was used for antigens directly spotted on nitrocellulose membranes (dot-blot analysis). Reference samples of transblotted total proteins and molecular weight markers were visualized by India ink staining (10% solution of fount India, Pelikan, Germany, in 0.2 M NaCl, 0.05 M Tris-HCl pH 7.4 containing 0.3% v/v Tween 20) for 30 min (Hancok K. et al., 1983, "India ink staining of proteins on nitrocellulose paper" Anal. Biochem. 133:157–162).

Immunoassay for determination of anti-mycobacterial Ig:

Multiwell microtiter plates (Microwell Module, Nunc, Denmark) were coated either with purified A36 or with *M. paratuberculosis* total cytoplasm (i.e. supernatant) (0.5 μg soluble proteins/50 μl 0.05 M Na carbonate buffer pH 9.6/well). Air dry wells were saturated with bovine serum albumin (0.1% w/v BSA in 0.15 M NaCl, 1 h, 37° C.). Increasing dilutions of serum to be tested in 0.15 M NaCl 0.02 M Na phosphate buffer pH 7.2 0.005% Tween 80 (PBST buffer) were added (50 μl/well, 1 h, 37° C.), optimal dilutions being identified by checker board titration. Horseradish peroxydase-labeled swine anti-rabbit, or rabbit anti-cow antiserum (Dako, Copenhagen, Denmark) were added (50 μl of 1/400 IgG dilution in PBST/well, 1 h, 37° C.). Excess reagent was removed by 5 buffer washings. After incubation with the peroxidase reagent (50 μl per well of a 17 mE Na citrate buffer pH 6.3 containing 0.2% O-phenylene diamine and 0.015% $H_2O_2$, 30 min, 37° C. in the dark), the reaction was stopped (50 μl 2 M $H_2SO_4$) and samples were spectrometrically measured (Plate reader SLT 210 from Kontron Analytical, U.K.). Results were recorded as ELISA absorbance values ($A_{450\ nm}$).

In some experiments, cross-reactive Ig were removed by incubation (18 h, 4° C.) with either purified TMA preparations (0.2 mg protein/ml of serum) or bacterial homogenates or intact mycobacteria (equivalents of 2 mg dry weight bacteria/ml of serum). Absorbed preparations were checked by dot-blot trials before application in immunoblot or immunoassay.

Immune electron microscopy:

Suspensions of mycobacteria in water ($5 \times 10^7$ cells/5 μl) were placed an carbon-formvar 200-mesh copper grids and air dried. Grids were serially incubated with: a) bovine serum albumin (3% solution in buffered saline, 30 min, 37° C.); b) anti-TMA complex rabbit antiserum (a $10^{-3}$ dilution of Ig in buffered saline with 0.05% Tween 20, 2 h, 37° C.); c) sheep anti-rabbit biotinylated Ig (1/200 dilution of Ig from Amersham, U.K., in buffered saline-Tween, 1 h, 20° C.); d) gold-labeled streptavidin (a 1/20 dilution of a preparation from Amersham, U.K.) (Cloeckaert A. et al., 1990, "Identification of seven surface-exposed Brucella outer membrane proteins by use of monoclonal antibodies: immunogold labeling for electron microscopy and enzyme-linked immunosorbent assay" Infect. Immun. 58:000-000). Grids were analyzed in a transmission electron microscope (Philips CM 10).

Results

Purification of TMA complexes and preparation of anti-TMA antisera:

The TMA complex of *M. paratuberculosis* (A36) has been prepared from the total homogenate. Cytoplasm fractionation by gel exclusion chromatography yielded said TMA complex within the exclusion fraction. The immunoelectrophoretic patterns of total cytoplasmic antigens (supernatant) (FIG. 1(1)) and of the exclusion fraction (FIG. 1(2)) are compared. From these tracings, which were obtained with polyclonal antisera elicited by inoculation of rabbits with whole mycobacterial homogenate, the purity of the A36 preparation can be inferred.

A similar protocol was used for preparation of other antigens of the TMA group from *M. avium, M. bovis* and *M. phlei*, which were used for comparative analysis.

The polyclonal antisera corresponding to the TMA complexes have also been prepared. The purity of these Ig preparations was checked by crossed immunoelectrophoresis: using total cell homogenates as antigens in every case, a single immunoprecipitogen line corresponding to the TMA complex was obtained (patterns not shown, mimicking that of FIG. 1(2)). It is to be noted that subcutaneous injection of TMA complex preparations invariably induced the synthesis of high titer antisera (ELISA absorbance higher than 2.5 for dilutions at $10^{-5}$), a result which stressed the high immunogenicity of these antigen complexes.

Development of A36-based serological assay for paratuberculosis:

The availability of A36 has prompted the development of an enzymometric ELISA-type immunoassay for paratuberculosis. Accordingly, multiwell plates were coated with A36 and incubated with sera of infected animals. Peroxidase-labeled rabbit anti-bovine IgG were added as second antibody, and the color developed after addition of peroxydase reagent was measured spectrophotometrically, as detailed in Materials and Methods. A comparative survey was made in parallel with A36 and with total cytoplasm (supernatant) of *M. paratuberculosis* (equal amounts of proteins were used for the two assays).

Figure 3:
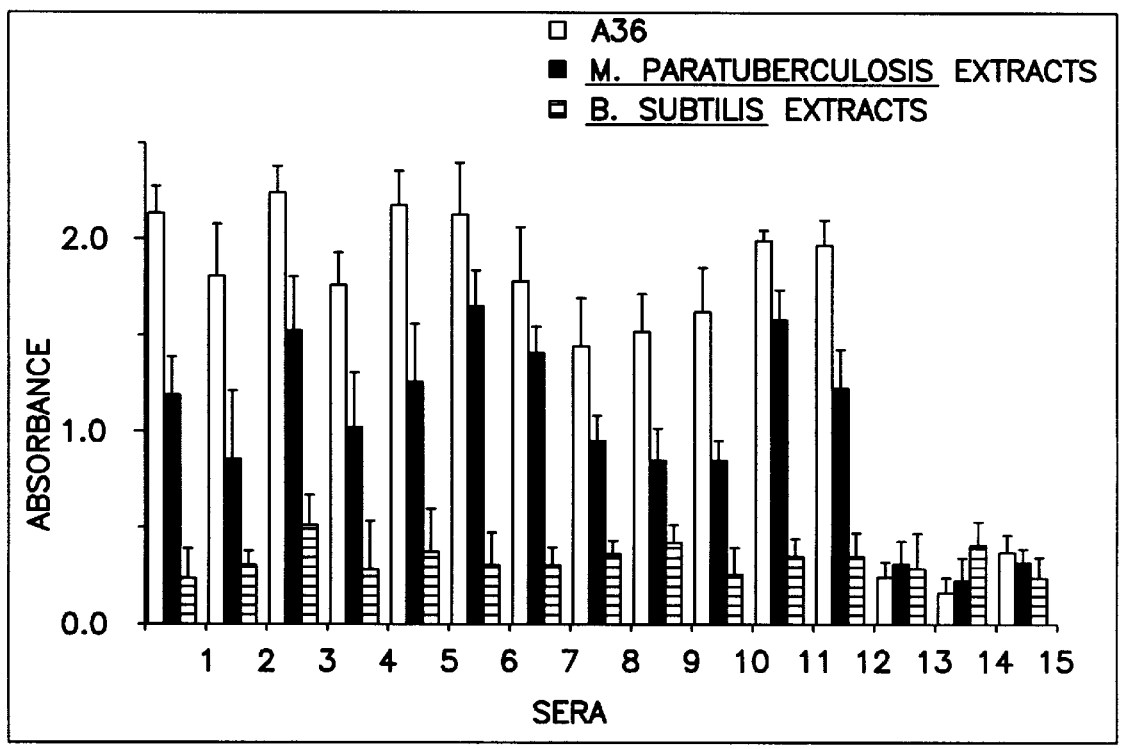

All the sera of infected animals (stages II and III of the Johne's disease) yielded a positive answer (values of 0.84 to 2.25 units) to both types of the ELISA assay (FIG. 3). On the contrary, uninfected animals were invariably negative (values lower than 0.38 units). With A36-ELISA, considerably higher absorbance values (1.44 to 2.25 units) were obtained than with the total cytoplasm-ELISA (0.84 to 1.65).

These results suggest the immunodominance of the A36 antigen in the Johne's disease, and the usefulness of the A36-based ELISA as a diagnostic assay.

Peripheral location of the TMA complex in mycobacteria:

The observed immunodominance of A36 is more compatible with a surface component than with an antigen complex located in the cytoplasm. However, a transfer of TMA complex through the envelope and its protrusion at the cell surface is conceivable.

The use of the immunoelectron microscopy methodology has allowed a direct approach to this problem. Multiplying cells of *M. paratuberculosis* were incubated with anti-A36 Ig from immunized rabbits. Cell-bound primary antibodies were revealed by secondary swine anti-rabbit IgG labeled with colloidal gold. Electron micrographs show the presence of antigen reactive spots on the surface of mycobacteria (results not shown).

These data indicate that part of the TMA complex does indeed occur within the cell wall and is presented on the cell surface.

Imunological crosareactivity of A36 and other TMA antigens:

In the preceding section, the development of a A36-based ELISA assay for titration of anti-mycobacterial antibodies has been described. The possible use of this assay in veterinary Medicine relies on its specificity with respect to: a) other mycobacteria which are usual hosts of the intestinal tracts of ruminants; and b) *M. bovis*, and *M. tuberculosis* which can cause tuberculosis in cattle (compulsory slaughtering of PPD-positive cattle). This problem was approached by evaluating the crossreactivity of TMA complexes from different mycobacteria with two procedures (see Table 1).

A first series of assays was carried out with microtitration plates coated with the TMA complex from *M. avium, M. bovis, M. paratuberculosis* and *M. phlei*. All these plates were used to titrate a single anti-A36 antiserum, a procedure yielding an evaluation of the percentage of shared TMA epitopes. Considering the autologous reaction (A36-anti A36 IgG) equal to 100, percentage of homology of *M. paratuberculosis* TMA complex with the TMA complex of *M. avium* and *bovis* was very high; it was much lower for *M. phlei* TMA complex.

When the A36-based ELISA assay was repeated with anti-A36 antiserum previously absorbed by different mycobacterial TMA complexes, an evaluation of the A36 specific epitopes was obtained. From Table 1, it results that the percentage of specific epitopes was low when the A36 was compared to the TMA of *M. avium* and *M. bovis,* it was high when compared to the TMA of *M. phlei.*

TABLE 1

CROSSREACTING AND SPECIES SPECIFIC EPITOPES
IN THE TMA COMPLEXES OF FOUR MYCOBACTERIA
TMA in ELISA

| Parameter | Coating reagent (plate)[a] | Absorbing reagent (antiserum)[b] | ELISA units ($A_{450\,nm}$)[c] | Epitopes (%) Cross-reacting | specific[d] |
|---|---|---|---|---|---|
| A. Crossreactivity | *M. parat.* | — | 2.367 | 100 | |
| | *M. avium* | — | 2.376 (±0.247) | 100 (±13) | |
| | *M. bovis* | — | 2.240 (±0.181) | 96 (±10) | |
| | *M. phlei* | — | 1.083 (±0.156) | 49 (±8) | |
| B. Specificity | *M. parat.* | *M. parat.* | 0.462 | | 0 |
| | *M. parat.* | *M. avium* | 0.574 (±0.197) | | 7 (±11) |
| | *M. parat.* | *M. bovis* | 0.603 (±0.238) | | 10 (±13) |
| | *M. parat.* | *M. phlei* | 1.073 (±0.141) | | 48 (±8) |

[a]TMA preparations from different mycobacteria (0.5 μg/well) were used to coat microtitration plates
[b]anti-A36 antiserum was pre-absorbed (samples B) or not (samples A) with TMA complex from different mycobacteria
[c]to plates coated with A36 (samples B) or with different TMAs (samples A) anti-A36 antiserum (1/150000 dilution) was added, and bound Ig were revealed by a second labeled antibody
[d]percentage of crossreacting or specific epitopes calculated on a logarithmic scale.

These results show the lack of species-specificity of the A36-ELISA as a diagnostic reagent for the Johne's disease. They suggest, however, the possible occurrence of A36 components endowed with such a specificity.

Immunodominance and specificity of the A36 proteins:

The species specificity, which was missing at the level of the complete A36 antigen complex, was sought with respect to its proteins components. The TMA complexes from *M. avium, M. bovis, M. paratuberculosis* and *M. phlei* were isolated, and their protein components were fractionated by polyacrylamide electrophoresis. A similarity of *M. avium* and *M. paratuberculosis* tracks is apparent, whereas those of *M. bovis* and *M. phlei* TMA were clearly different to the *M. paratuberculosis* track.

When fractionated A36 proteins were immunoblatted with anti-A36 antiserum, a dozen of major polypeptides were stained, most of them located in the 28–42 kDa region. Immunoblotting with anti-A36 antiserum pre-absorbed with a lysate of *M. phlei* yielded 5 polypeptide bands; they were 3 in the case of *M. bovis* and one with *M. avium.* Table 2 provides a comparative evaluation of the main A36 components according to two properties: immunogenicity level (staining intensity by pooled sera of infected bovines) and species specificity (lack of cross-reactivity with the other mycobacteria). Eleven major components of 22 to 74 kDa are listed: two of them (of 23 and 31 kDa) containing specific epitopes with respect to the tested organisms except *M. avium,* and one of 34 kDa containing specific epitopes with respect to all of the tested organisms including *M. avium.*

TABLE 2

IMMUNOLOGICAL CHARACTERISTICS OF
SOME PROTEINS OF THE TMA COMPLEX OF
MYCOBACTERIUM PARATUBERCULOSIS (A36)

| Pro-tein[a] (kDa) | Immunogenicity[b,c] (level in hosts) | | | | Specificity[d] towards | | |
|---|---|---|---|---|---|---|---|
| | rabbit anti-A36 | infected bovines | | | *M. avium* | *M. bovis* | *M. phlei* |
| | | I | II | III | | | |
| 74 | ++ | − | − | + | no | no | no |
| 52 | + | − | − | − | no | no | no |
| 41 | + | + | + | + | no | no | yes |
| 40 | +++ | + | + | + | no | no | no |
| 37 | ++ | ++ | − | ++ | no | no | yes |
| 35 | + | ++ | ++ | ++ | no | no | yes |
| 34 | +++ | +++ | +++ | +++ | yes | yes | yes |
| 31 | ++ | +++ | − | +++ | no | yes | yes |
| 29 | +++ | − | − | + | no | no | yes |
| 23 | +++ | − | + | − | no | yes | yes |
| 22 | + | − | ++ | − | no | no | yes |

[a]A36 was dissociated and protein components were fractionated by SDS-PAGE electrophoresis and identified by immunoblotting
[b]degree of immunogenicity for rabbits and cows was evaluated from the intensity of immunoblot staining with the corresponding sera
[c]sera from cattle affected by different stages of the Johne's disease: I, asymptomatic-non excretory; II, asymptomatic-excretory; and III, symptomatic-excretory forms
[d]crossreactivity was expressed by a no, and specificity by a yes.

Figure 4:
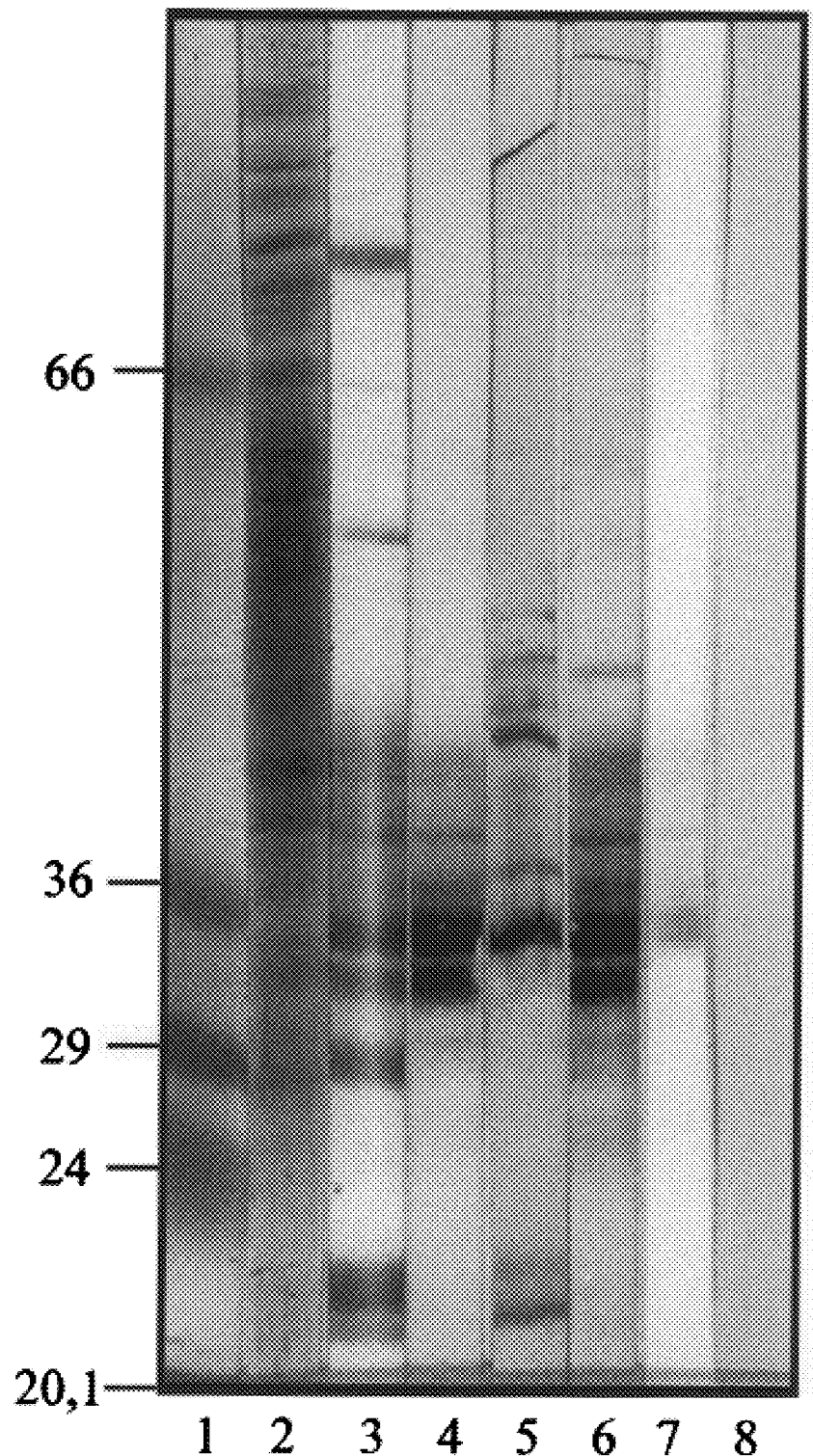
Figure 5:
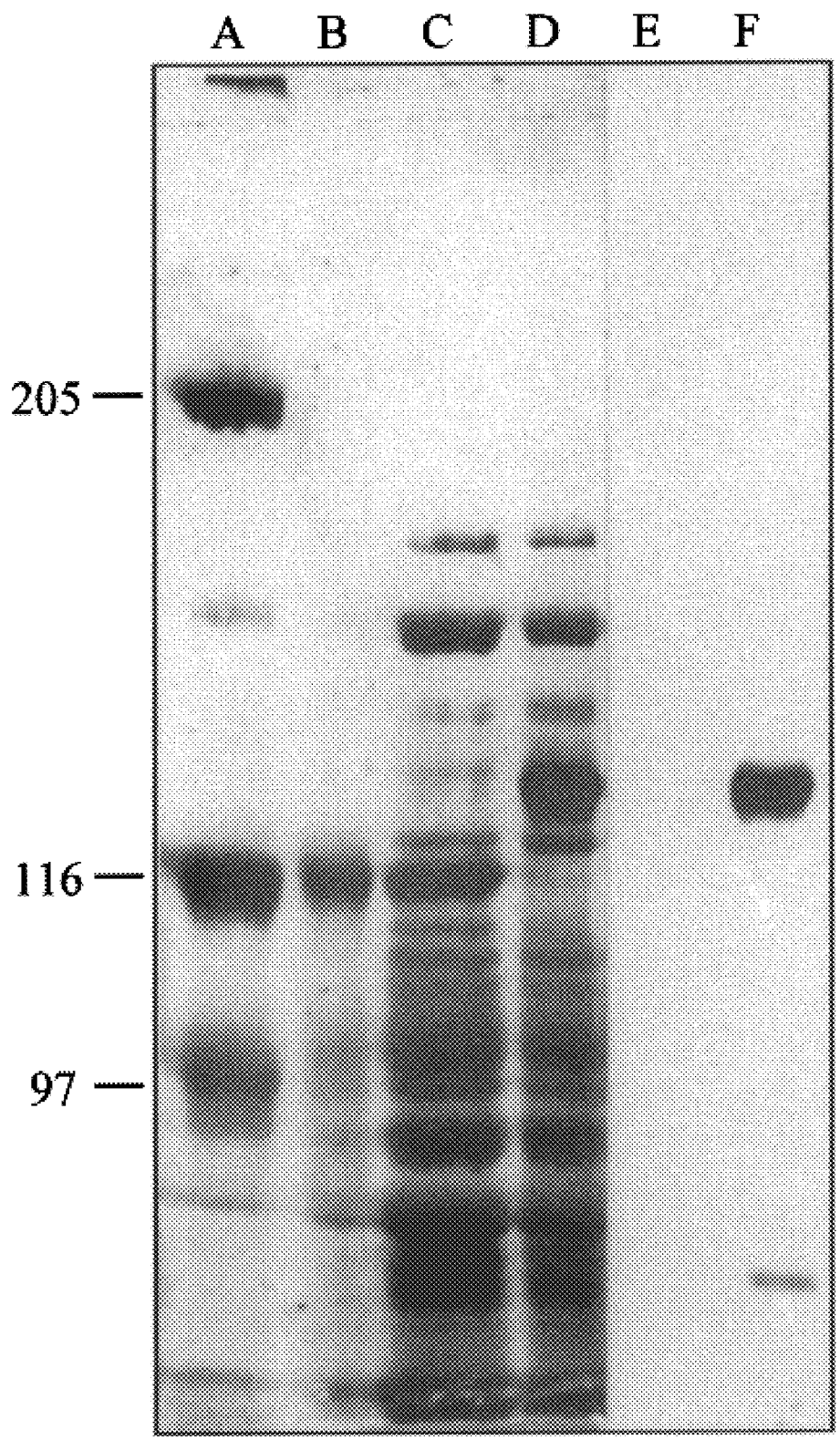
Figure 6:
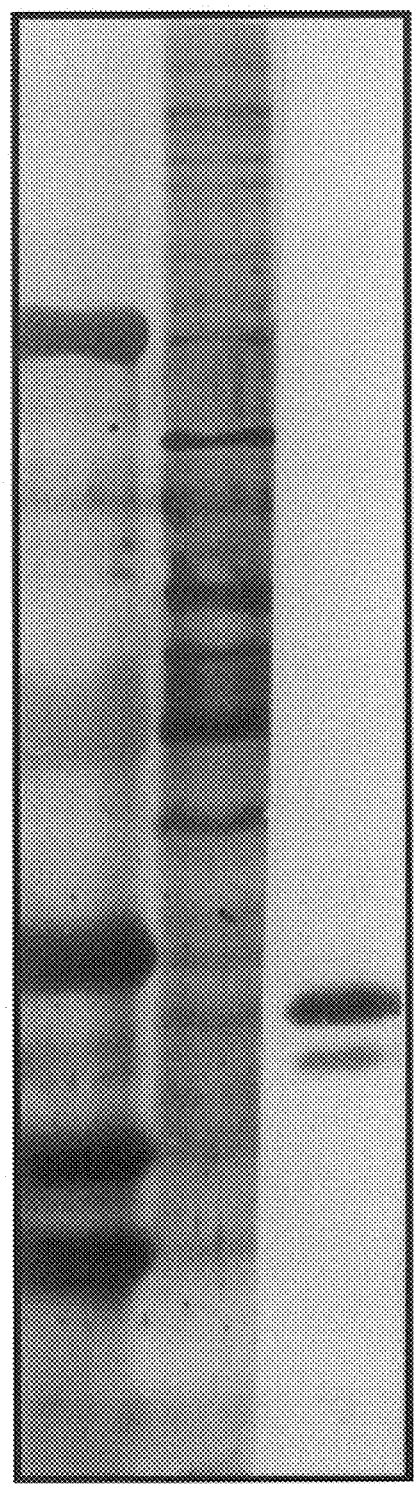

The immunological relevance of the latter protein was checked by immunoblot analysis of A36 proteins with infected bovine sera: a major band at the level of the 34 kDa marker was observed (FIG. 4, lanes 4, 5, 6 and 7). This band was missing in the control (lane 8 with healthy bovine serum).

It is thus evident that the 34 kDa protein component of the TMA complex is immunodominant in cattle, relevant to Johne's disease, and containing species-specific epitopes with respect to related mycobacteria.

The present invention enables to develop a A36 based ELISA test for paratuberculosis: its ability to reveal the presence of a mycobacterial infection in cattle has been proven in FIG. 3. Basic requirements for the use of a given antigen as reagent for immunoassays of medical interest are: 1) its immunodominance; 2) its relevance to the targeted disease; and 3) its specificity. Requirements 1 and 2 were therefore fulfilled by the A36 based-ELISA. Requirements 1 to 3 are completely fulfilled by the p362 polypeptide which is part of the 34 kDa protein belonging to A36, as described hereafter.

EXAMPLE II

Isolation of Clone a362 Expressing a 10 kDa Polypeptide (p362), DNA Sequencing of the Insert of Clone a362 and Testing of p362 in an ELISA for Johne's Disease Material and Methods Cloning Vectors The following types were used: λgt11 (Young R. A. and Davis R. W., 1983, "Yeast RNA polymerase II genes: isolation with antibody probes" Proc. Natl. Acad. Sci. USA 80:1195–1198) and pUEX2 (Brennan G. M. et al., 1987, pUEX, a bacterial expression vector related to pEX with universal host specificity" Nucl. Acids Res. 15:10056) and pmTNF-MPH (see FIGS. 9a, 9b and Table 5) as expression vectors, and the Blue-Script SK$^+$as sequencing vector (Stratagene).

Bacteria

*Mycobacterium paratuberculosis* 19698 (from the American Type Culture Collection). *M. paratuberculosis:* strain 2887 (Crohn): ATCC n° 43015. *M. avium* serotype 4, *M. avium* serotype 2, *M. avium* serotype 8 (Schaefer W. B., 1965, "Serologic identification and classification of the atypical mycobacteria by their agglutination" Am. Rev. Resp. Dis. suppl. 92:85–93). *M. tuberculosis* H37rv: ATCC n° 25618. *M. gordonae:* ATCC n° 14470. *Brucella abortus* B3 (Cloeckaent A. et al., 1990, Infect. Immun. 58:3980–3987). Strains of *Escherichia coli:* Y1089 (Δ(lacU169), Δ(lon), hflA150 (chr::Tn10), (pMC9), (rK$^-$, mK$^+$)), Y1090 (Δ(lacU169), Δ(lon), sup F, (trpC22::Tn10), (pMC9), (rK$^-$, mK$^+$)), MC1061 (Δ(lacX74), galU$^-$, galK$^-$, (rK$^-$, mK$^+$)) and DH5αF' (F', (rK$^-$, mK$^+$), supE44, lacZΔM15, Δ(lacZYA argF) U169), K12ΔH, ATCC 33767 (lacZ(am) Δ(bio uvr B) (λ Nam7 am53 cI 857 ΔH1) rpsL20).

Antisera

Rabbit anti-*M. paratuberculosis* antiserum was from Dako (Copenhagen, Denmark, lot n° 014). Sera from paratuberculosis-infected cattle were provided by Dr. M. Desmecht (National Institute for Veterinary Research, Brussels) and Dr. B. Limbourg (Erpent, Center of Veterinary Medicine, Belgium).

Polyclonal antisera against whole homogenate of *M. avium* serotype 4, *M. bovis* BCG, and *M. phlei,* as well as those against the TMA complex and βgal-p362 (recombinant polypeptide of the invention fused to β-galactosidase hereafter described) were produced by repeated subcutaneous inoculations into rabbits (10 μg proteins/0.5 ml buffered saline emulsified with equal volume of incomplete Freund's adjuvant, 6 inoculations at 1-week intervals).

Purification of *M. paratuberculosis* DNA

Suspensions of bacteria (10 mg in 0.5 ml of 100 mM NaCl, 1 mM EDTA, 50 mM Tris-HCl pH 7.4) were incubated sequentially with lysozyme (25 μl of 20 mg/ml, 14 h, 50° C.), pronase (25 μl of 20 mg/ml, 1 h, 37° C.), and SDS (25 μl of 20%, 1 h 37° C.). Mixtures were extracted with chloroform-isoamyl alcohol (24:1, vol:vol), water-saturated phenol, and ether. After incubation with ribonuclease (5 μl of 2 mg/ml, 1 h, 37° C.), DNA was purified on columns of Sephadex G50 (equilibrated with 4.8 mM sodium phosphate pH 6.8) and hydroxyapatite (washed with 8 M urea, 0.1 M sodium phosphate buffer pH 6.8 containing 1% SDS, and then with 4.8 M sodium phosphate pH 6.8, and eluted with 480 mM sodium phosphate pH 6.8).

Construction of a λgt11 Library of *M. paratuberculosis*

*M. paratuberculosis* DNA was sheared to average length segments of 0.5 to 1.5 kb (Vibra Cell ultrasonicator 60 W, 2 sec). Shearing was monitored by agarose gel electrophoresis. EcoR1 sites were methylated with EcoR1 methylase (5 μg of sheared DNA in 50 μl of buffer (50 mM Tris-HCl pH 7.5, 1 mM Na$_3$EDTA, 5 mM dithiothreitol, 50 μM S-adenosyl-L-methionine and 10 units of EcoR1 methylase). Methylation was pursued for 30 min at 37° C., and stopped by 10 min incubation at 70° C. Blunt-end DNA fragments were obtained by incubation with T4 DNA polymerase (5 μl of 0.1 M MgCl$_2$, 2.5 μl of 1 mM dTNPs, 1 μl of 1 M(NH$_4$)$_2$SO$_4$, and 20 units of T4 DNA polymerase per 40 μl methylation reaction medium; 20 min incubation at 37° C.). EDTA (15 mM final concentration) was added, reaction mixture was extracted with phenol/chloroform twice, and the aqueous. phase was extracted with ether. After addition of sodium acetate 0.3 M final concentration, DNA was precipitated with 2 vol of EtOH at −20° C. and washed with 70% EtOH. DNA pellet was dissolved in buffer (10 μl of 100 mM Tris-HCl pH 7,5, 20 mM MgCl$_2$, 20 mM dithiothreitol), phosphorylated EcoR1 linkers (200 μg/ml) were added, followed by addition of PEG 6000 (final concentration 15%), 1 mM ATP (final concentration) and 2 units of T4 DNA ligase, and the reaction mixture was incubated overnight at 12° C. This mixture was incubated at 37° C. with an excess of EcoR1, and DNA fragments were purified from linker excess on Sephadex G25. The DNA solution thus obtained was extracted sequentially with phenol/chloroform and ether, precipitated, and washed with ethanol. DNA pellet (0.5 μg) was dissolved in TE buffer (10 mM Tris-HCl pH 7.5, 0.1 mM EDTA) and ligated (18 h, 4° C.) with 1 μg of dephosphorylated EcoR1-digested λgt11 DNA (Promega). Methylation, ligation, and digestion steps were controlled by agarose gel electrophoresis. Phage packaging of cloned DNA was obtained with the Stratagene gigapack extract.

Screening of the λgt11 Library and Dot-blot Technique

After infection of *E. coli* Y1090 by the recombinant phage mixture and spreading them out over the plate, they were incubated for 3–4 h at 42° C.

For identification of recombinant phages, IPTG (isopropylthio β-galactopyranoside) (10 mM) saturated nitrocellulose filters were placed directly on the surface of the overlay plates containing the plaques and incubated for 18 h at 37° C. (Young R. A. and Davis R. W., 1983, "Yeast RNA polymerase II: genes: isolation with antibody probes" Proc. Natl. Acad. Sci. USA 80:1195–1198). After spotting of control antigens (1 μg) and washing for 10 min with TBS buffer (0.5 M NaCl, 0.023 M Tris-HCl pH 7.5), filters were incubated for 30 min with the same buffer containing 3% (w/v) gelatin and then with the rabbit anti-*M. paratuberculosis* antiserum (Dako) previously diluted with TBST buffer (TBS buffer containing 0,05% (v/v) Tween 20) containing 1% (w/v) gelatin. After washing, filters were incubated for 1 h with 1/400 dilutions of peroxydase-labeled anti-rabbit Ig. After repeated washing with TBST and TBS, the peroxydase substrate α-chloronaphtol (Bio Rad Laboratories, Richmond, Calif.) and hydrogen peroxide were added. Reaction was stopped by washing with distilled water. Plaques corresponding to reactive spots on the filters were picked off, transferred to SM medium (100 mM NaCl, 10 mM MgSO$_4$, 20 mM Tris-HCl pH 7.4) and purified by repeated passages in E. coli Y1090. Recombinant clones were then further characterized with respect to their antigenicity (incubation with bovine sera and anti-A36) and their specificity (incubation with antibodies directed against homogenate of M. avium, M. bovis and M. phlei) using the same procedure as described above.

A similar technique was used for dot-blot experiments in which the specificity of the recombinant polypeptide p362 was tested with respect to different mycobacteria: spots of mycobacterial homogenates on nitrocellulose membranes were incubated with anti-βgal-p362 Ig.

High Level Expression of Fusion Protein in E. coli

Colonies of E. coli Y1089 lysogenized with the appropriate λgt11 recombinants were multiplied at 30° C. in Luria-Bertani medium ($A_{6000\ nM}$=0.5). After heat shock (20 min at 45° C.), production of β-galactosidase fusion proteins of the invention was induced by the addition of 10 mM IPTG (final concentration) and further incubation (60 min at 37° C.). Cells harvested by centrifugation were suspended in buffer (10 mM Tris-HCl, pH 8.2, 2 mM EDTA) and rapidly frozen in liquid nitrogen.

For enhanced expression, λgt11 inserts were subcloned into the expression vector pUEX2 (Brennan G. M. et al., 1987, "pUEX, a bacterial expression vector related to pEX with universal host specificity" Nucl. Acids Res. 15:10056), commercially available from Amersham, which was. used to transform E. coli MC1061 (Maniatis, Molecular Cloning). Single colonies of transformed E. coli were grown at 30° C. to $A_{600}$=0.3 and heat-shocked (90 min at 42° C.). Harvested cells were lysed by sonication and frozen in liquid nitrogen.

Protein Fractionation and Immunoblotting

The TMA complex and recombinant proteins were analyzed by polyacrylamide gel electrophoresis under denaturing conditions (SDS PAGE) (Laemmli, U. K. 1970, "Cleavage of structural proteins during the assembly of the head of bacteriophage T4", Nature 227:680–695).

Fractionation on 7.5 or 10% acrylamide gels was carried out in a 2001 vertical electrophoresis unit (LKB-Produkter AB, Bromma, Sweden) (4 h, 50 V, 20° C.). Molecular weight protein markers (Sigma, St Louis, Mo.) were: myosin (205 kDa), β-galactosidase (116 kDa), phosphorylase B (97,4 kDa), bovine serum albumin (66 kDa), ovalbumin (45 kDa), glyceraldehyde-3-phosphate dehydrogenase (36 kDa) carbonic anhydrase (29 kDa), trypsinogen (24 kDa), trypsin inhibitor (20.1 kDa), and α-lactalbumin (14.2 kDa). Protein bands were stained with Coomassie brilliant blue. Electrophoresed proteins were transblotted (LKB 217 Multiphor 2 Electrophoresis System, 10 V, 2 h, with buffer 20% methanol, 0.039 M glycine and 0,048 M Tris base, pH 8.8) onto nitrocellulose membranes. Mycobacterial antigens were visualized by sequential incubation with polyclonal rabbit antisera (anti-A36 for recombinant mycobacterial antigens fused to β-galactosidase or anti-βgal-p362 for TMA proteins) and peroxydase-labeled anti-rabbit Ig (Dako, Copenhagen, Denmark) (1/400 dilution). Total protein blotted on the membrane was visualized by staining with India ink.

DNA Sequencing

Sequence analysis of the DNA insert of the recombinant clone a362 was done by the primer extension and dideoxy termination method (Sanger F. et al., 1977, "DNA sequencing with chain terminating inhibitors", Proc. Natl. Acad. Sci. USA 74:5463–5467), after subcloning of the λgt11 insert into the sequencing vector pBluescript SK$^+$ (Stratagene). Sequencing reactions were performed with T7 DNA polymerase and different primers (universal, reverse, SK, and KS primers from Deaza Kit, Pharmacia, Uppsala, Sweden). Computer-aided analysis of nucleic acid and polypeptide sequences were performed with the program COD-FICK (PC-GENE, Intelligenetics, USA). Homology searches were performed on DNA level in EMBL bank (release 29) and UGEN bank (release 70-29)(Intelligenetics Inc., CA-USA), and on protein level in PIR bank (release 31) and Swiss Prot (release 20). No homologous sequences were found.

Serological Analysis (ELISA) with Recombinant Polypeptides

Multiwell microtiter plates (Microwell Module, High binding Capacity, Nunc, Denmark) were coated with total cytoplasm of E. coli-a362 and with total cytoplasm of E. coli as a control. Four μg of soluble proteins/50 μl 0.05 M Na carbonate buffer pH 9.6 were coated per well. Plates were air dried overnight and saturated (0.1% serum albumin in 0.15 M NaCl, 1 h at 37° C.). Dilutions of bovine Ig in PBST (0.15 M NaCl, 0.02 M phosphate buffer pH 7.2, containing 0.005% Tween 80) were added to plate wells (50 μl, 1 h at 37° C.), Peroxydase-labelled rabbit anti-cow Ig (Dako) (50 μl, 1/400 dilution in PBST/per well) were added (1 h at 37° C.). Excess of reagent was removed by 5 PBST washings. After incubation with peroxydase reagent (50 μl/well of 0.2% O-phenylenediamine with 0.015% hydrogen peroxyde in 0.017 M Na citrate buffer pH 6.3, 30 min, 37° C. in the dark), the reaction was stopped with 50 μl 2 M H$_2$SO$_4$, and $A_{450\ nm}$ was measured in a calorimetric plate reader (SLT 210, Kontron Analytical, UK). Results were recorded as ELISA absorbance values. In some experiments, cross reactive Ig were removed by incubation (18 h at 4° C.) with bacterial homogenate. Absorbed preparations were checked by dot-blot trials before applications in immunoblots or immunoassays.

Immune Electron Microscopy

Suspensions of mycobacteria in water (5×10$^7$ cells/5 μl) were placed on carbon-formvar 200-mesh copper grids and air-dried. Grids were serially incubated with: a) bovine serum albumin (3% solution in buffered saline, 30 min, 37° C.); b) anti-βgal-p362 rabbit antiserum (a 10$^{-3}$ dilution of Ig in buffered saline with 0.05% Tween 20, 2 h, 37° C.); c) sheep anti-rabbit biotinylated Ig (1/200 dilution of Ig from Amersham, U.K., in buffered saline-Tween, 1 h, 20° C.); d) gold-labelled streptavidin (a 1/20 dilution of a preparation from Amersham, U.K.) (Cloeckaert A. et al., 1990, "Identification of seven surface-exposed Brucella outer membrane proteins by use of monoclonal antibodies: immunogold labeling for electron microscopy and enzyme-linked immunosorbent assay", Infec. Immun. 58:3980–3987).

Grids were analyzed in a transmission electron microscope (Philips CM 10).

Results

1. Preparation of a Genomic Library of M. paratuberculosis and Isolation of Recombinant Clones A genomic library of M. paratuberculosis has been prepared by the use of the expression vector λgt11. For this purpose, purified mycobacterial DNA was sonicated under controlled conditions yielding segments of 10$^3$ L on the average (0.5 to 2×10$^3$). These fragments were methylated by EcoR1 DNA methylase (efficiency of methylation was controlled by incubation with EcoR1), incubated with T4 DNA polymerase to obtain blunt-end DNA, and provided with EcoR1 linkers by incubation with T4 DNA ligase. After EcoR1 digestion, DNA segments were purified free of linker excess and inserted into EcoR1-cleaved λgt11 by incubation with T4 DNA ligase (a step checked by gel electrophoresis). After packaging and infection of E. coli Y1090, 7.5×10⁵ recombinant clones (75% of total clones) were obtained, one third of which was screened with rabbit anti-M. paratuberculosis antiserum (Dako). After repeated purifications, ten recombinant clones were selected: three of them expressed TMA complex proteins, and seven produced epitopes of proteins not present within the TMA complex.

2. Analysis of Antigenicity and Specificity of Polypeptides Produced by Recombinant Clones Since cloning of M. paratuberculosis genes was aimed at producing polypeptides to be used as diagnostic reagents, it appeared essential to test the reactivity of recombinant clones towards sera of cattle affected by the Johne's disease. As shown in Table 3, all the selected clones reacted with sera of animals bearing one of the clinical forms of the disease. The strongest reactions were afforded by clones a4 and a362. On the contrary, no reactivity was observed with sera from healthy bovines.

TABLE 3

Characteristics of clones expressing an antigenic polypeptide of *M. paratuberculosis*

| | Antigenicity** | | | Specificity with respect to** | | |
|---|---|---|---|---|---|---|
| Clones* | 1 | 2 | 3 | *M. avium* | *M. bovis* | *M. phlei* |
| a1 | (+) | + | + | no | no | yes |
| a2 | + | + | + | yes | yes | yes |
| a3 | + | + | ++ | no | yes | yes |
| a4 | ++ | ++ | ++ | no | no | yes |
| a5 | + | + | + | no | yes | yes |
| a6 | + | + | ++ | no | no | yes |
| a7 | (+) | + | + | no | no | no |
| a361 | + | + | ++ | no | yes | yes |
| a362 | ++ | ++ | ++ | yes | yes | yes |
| a363 | (+) | + | + | no | no | yes |

*only clones a361 to a363 express polypeptides belonging to the TMA complex.
**detected by sera from asymptomatic and non excretory bovine (1), asymptomatic and excretory bovine (2) and symptomatic and excretory bovine (3); quantified as low reaction "(+)", good reaction "+" and very good reaction "++".
***cross reactivity was expressed by a "no", and specificity by a "yes".

Another requirement of paramount importance was the specificity with respect to mycobacteria belonging to the saprophytic and pathogenic flora of cattle. Recombinant clones were tested for reactivity with antisera against homogenates of *M. avium, M. bovis* and *M. phlei.* It was previously shown that the overall DNA homology levels of these three mycobacteria with respect to *M. paratuberculosis* were respectively 94, 52, and 19 percent (Hurley S. S. et al., 1988, "DNA relatedness of *M. paratuberculosis* to other members of the family of mycobacteriaceae", Int. Journal Syst. Bact. 38:143–146). Data in Table 3 indicate that, although all clones but one were specific towards *M. phlei,* only five of them were specific for *M. bovis* and two for *M. avium.*

In conclusion, only two of the selected clones, a2 and a362 fulfilled both requirements for species-specificity and relevance to Johne's disease. Moreover, only the latter clone reacted with anti-A36 antiserum and corresponded, therefore, to a A36 protein, presumably the 34 kDa protein previously identified as a TMA complex component with species-specific epitopes. The remaining part of this example relates to the characterization and use of clone a362.

3. Size of Clone a362 Insert and its Expressed Polypeptide P362

EcoR1 cleavage of DNA of clone a362 yielded an insert of about 500 bp devoid of internal EcoR1 restriction sites (not shown).

*E. coli* Y1089 was lysogenized by the recombinant phage, and the synthesis of a chimaeric protein fused with β-galactosidase was induced by IPTG: a fusion protein of about 125 kDa (βgal-p362) was produced (FIG. 5). Since β-galactosidase (116 kDa) misses 2 kDa in λgt11, the recombinant polypeptide coded for by the insert of clone a362 (p362) is expected to be about 11 kDa in size. Consequently, only a roughly 300 bp portion of the 500 bp insert coded for such an 11 kDa polypeptide. This was confirmed by sequencing and determination of the orientation of the insert DNA as described further.

4. Production of P362 Recombinant Polypeptide and Evidence of its Belonging to a 34 kDa Protein of A436

Since the production of the β-gal p362 by *E. coli* Y1089 containing the λgt11-recombinant phage was only 2% of total proteins, the corresponding insert was recloned in a more favorable expression vector. For this purpose, the λgt11 insert of the a362 recombinant clone was freed by incubation with EcoR1, purified by electroelution from an agarose gel (75% recovery), and recloned into the EcoR1 site of the expression vector pUEX2 (Amersham). In this case, production of βgal-p362 fusion protein in the transformed MC1061 strain of *E. coli* ($6\times10^5$ transformants/μg DNA) was about 25% of total proteins.

After running the SDS-PAGE of the lysate from the transformed strains, the recombinant fusion protein was eluted from the polyacrylamide gel and used to elicit antibodies in rabbits (anti-βgal-p362).

The protein components of the TMA complex from *M. paratuberculosis* were fractionated by electrophoresis on polyacrylamide gels (SDS PAGE). After transfer to nitrocellulose sheets, TMA proteins were incubated with anti-βgal-p362. As shown in FIG. 6, a major band corresponding to the 34 kDa protein of the TMA complex was immunolabeled: this was the unique TMA protein containing species-specific epitopes as above reported. A second band of about 31 kDa was stained to minor extent: it was also present in the immunoblots of TMA proteins with sera of infected cattle.

5. Localization of the P362 Polypeptide at the Bacterial Surface

Since the A36 antigen complex was previously shown to be present at the cell surface, a peripheral location of the p362 recombinant polypeptide would further confirm the belonging of p362 recombinant polypeptide to a protein of the A36 complex. Electron micrographs show indeed the presence of the p362 polypeptide within the cell wall and its release during the declining growth phase (results not shown).

6. Assessment of the Species-specificity of the Recombinant Polypeptide p362

From what is above-mentioned, it is shown that the 34 kDa protein component of the TMA complex of *M. paratuberculosis* contains epitopes devoid of crossreactivity towards *M. bovis, M. avium* and *M. phlei.* Although the recombinant p362 polypeptide, which apparently represents a portion of the 34 kDa protein, is likely to be endowed of species-specificity, a more stringent confirmation is needed for a polypeptide forecast as reagent for serological tests. Consequently, the specificity of p362 was tested against two series of *M. paratuberculosis* and *M. avium* isolates from cattle as well as against certain Gram-positive and Gram-negative bacteria being usual hosts of bovine gut (Table 4).

The dot-blot experiment was carried out by spotting on a nitrocellulose membrane 2 μg samples of different bacterial homogenates. Membranes were then incubated successively with rabbit anti-βgal-p362 antiserum and, after washing, with peroxydase-labeled swine anti-rabbit IgG. Spots were revealed by the peroxydase reaction. All of eight *M. paratuberculosis* isolates were positive, whereas the closely related organisms of the MAIS group were negative. None of the other tested mycobacteria gave a positive reaction, neither did the Nocardia and Brucella species (see Table 4).

8. Testing of p362 in an ELISA for Johne's Disease

The 10 kDa polypeptide (p362), endowed with species-specificity, and being part of the 34 kDa protein of A36, can be used as a specific test for paratuberculosis.

Figure 2:
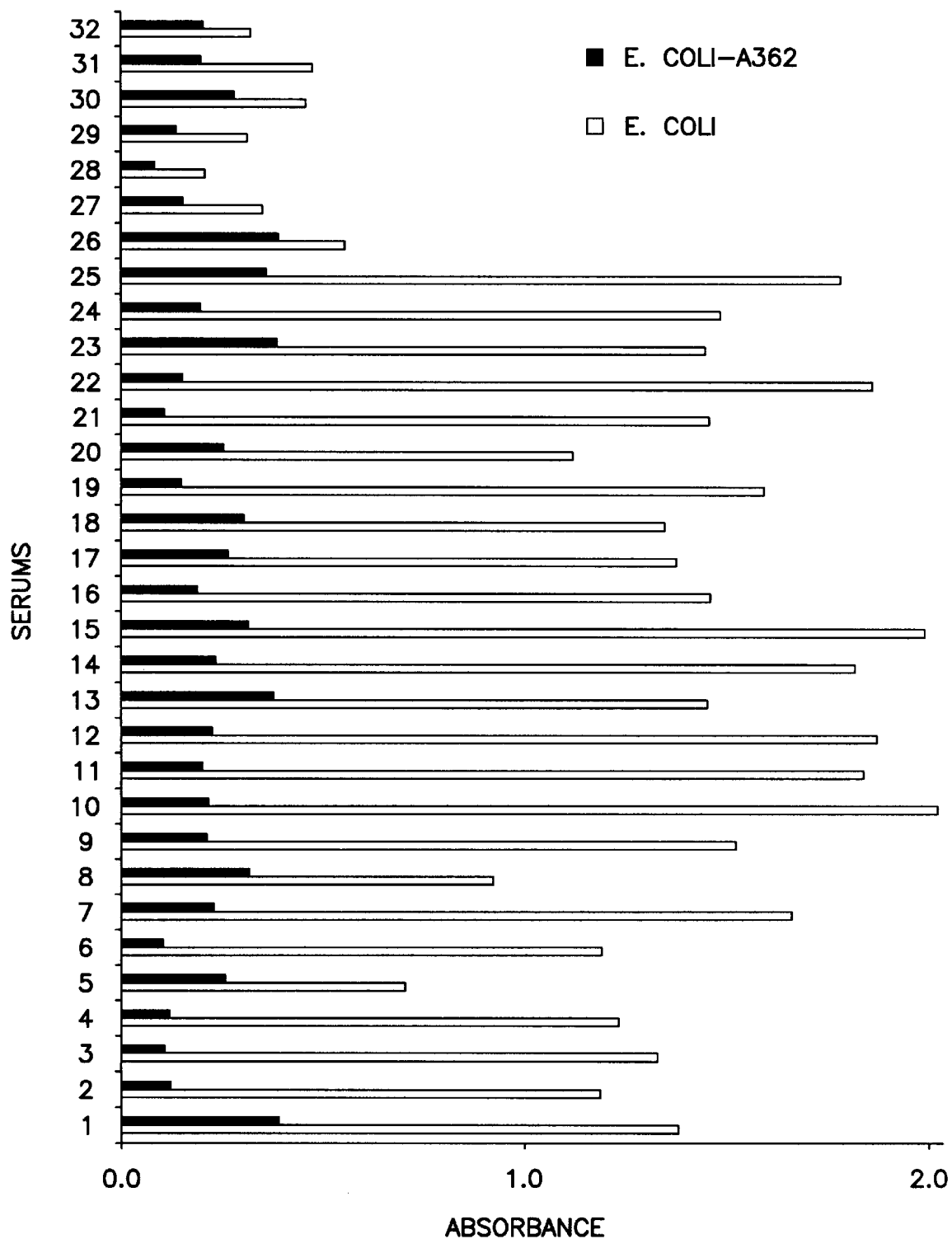

A preliminary test has been done using plates coated with total cytoplasm of *E. coli*-a362 containing p362. Bovine sera were preabsorbed to *E. coli*-control homogenate. FIG. 2 shows that all sera from infected bovines react significantly with p362. On the contrary, healthy bovines (samples 26–32) do not give a signal which is significantly higher than that observed with *E. coli*-control cytoplasm.

TABLE 4

SPECIFICITY OF p362 TOWARDS OTHER [MYCO]BACTERIA

| Bacterium lysates | Anti-βgal-p362 | Bacterium lysates | Anti-βgal-p362 |
|---|---|---|---|
| *M. paratuberculosis:* | | | |
| 2E | + | *M. intracellulare* (1) | – |
| 316F | + | MAIS A3 (4) | – |
| ATCC 19698 | + | MAIS A84 (4) | – |
| ATCC 43015 | + | MAIS 8715 (4) | – |
| 2890 (bovine) (1) | + | MAIS 87537 (4) | – |
| 2891 (bovine) (1) | + | *M. bovis* BCG GL2 | – |
| 2895 (goat) (1) | + | *M. tuberculosis* H37rv (6) | – |
| 172 28/66 (bovine) (2) | + | *M. phlei* AM76 (1) | – |
| *M. avium* D4(5) | – | *M. leprae* (1) | – |
| *M. avium* serotype 4 | – | *M. fortuitum* M62 (1) | – |
| *M. avium* serotype 8 | – | *M. smegmatis* (1) | – |
| *M. avium* serotype 2 | – | *M. gordonae* ATCC 14430 | – |
| *M. scrofulaceum* (1) | – | *Nocardia asteroides* (1) | – |
| *Salmonella typhimurium* (3) | – | *Brucella abortus* B3(3) | – |

(+) positive immunological reaction
(–) absence of reaction
(1) Portaels IMTA (Institut de Médecine Tropicale, Anvers Belgique)
(2) from Kaeckenbeeck DBUL (Département de Bactériologie, Université de Liège, Belgique)
(3) from LIMET ICP (Institut of Cellular Pathology, Belgique)
(4) from Defoe IPB (Institut Pasteur du Brabant, Belgique)
(5) from Saxegaard NVIN (National Veterinary Institute, Norway).
(6) ATCC 25618

7. Sequencing of the Cloned Insert Coding for Polypeptide p362

To sequence the 500 bp DNA segment coding for the polypeptide p362, the insert of clone a362 was isolated by EcoR1 cleavage from the chimaeric vector λgt11 and recloned into the Bluescript vector SK⁺. After transformation of *E. coli* DH5αF', clones carrying inserts coding for p362 were selected.

The sequence of the insert showed the occurrence of a 507 bp DNA segment flanked by two EcoR1 extremities (FIG. 7C (SEQ ID NO:3)). The G+C content of this segment was 70%, in agreement with the 64% G+C of the whole *M. paratuberculosis* genome. The sequence in FIG. 7C (SEQ ID NO:3) yielded two open reading frames in phase with the EcoRI sites: a 306 bp region (1 to 306) in one direction, and a 185 bp region (507 to 322) into opposite orientation. The program COD-FICK (PC-GENE) which takes in account the codon usage, confirmed the coding ability of the two open reading frames. They coded respectively for 10 kDa and 7 kDa polypeptides. The insert was subcloned in an expression vector in *E. coli* in both orientations. only one orientation yielded an expression product reacting with the rabbit anti-βgal-p362 antiserum. Restriction analysis led to the selection of the 306 bp open reading frame as being the one coding for the p362 polypeptide [10 kDa]. The selected coding region and the aninoacid sequence of polypeptide p362, corresponding to the carboxyterminal extremity of the 34 kDa protein are displayed in FIG. 8.

Antibodies directed against p362 are already present in the early stages of the disease (samples 1–13). p362 can thus be considered as a very suitable antigen for specific and sensitive diagnosis of paratuberculosis.

To decrease the background levels due to cross reaction with the β-galactosidase part of the fusion protein, the insert coding for p362 was recloned into another expression vector (pmTNF-MPH, Innogenetics) (FIGS. 9a and 9b)(SEQ ID NOS:6,7 and 8).

It contains the tetracycline resistance gene and the origin of replication of $pAT_{153}$ (obtainable from Bioexcellence, Biores B. V., Woerden. The Netherlands), the lambda PL promoter up to the MboII site in the N gene 5' untranslated region (originating from pPL(λ); Pharmacia), followed by a synthetic ribosome binding site (see sequence data), and the information encoding the first 25 AA of mTNF (except for the initial Leu which is converted to Val). This sequence is, in turn, followed by a synthetic polylinker sequence which encodes six consecutive histidines followed by several proteolytic sites (a formic acid, CNBr, kallikrein, and *E. coli* protease VII sensitive site, respectively), each accessible via a different restriction enzyme which is unique for the plasmid (SmaI NcoI, BspMII and StuI, respectively; see restriction and genetic map, FIG. 9a) (SEQ ID NO:6 and 7). Downstream from the polylinker, several transcription terminators are present including the *E. coli* trp terminator (synthetic) and the $rrnBT_1T_2$ (originating from pKK223-3; Pharmacia). The total nucleic acid sequence of this plasmid is represented in FIG. 9b (SEQ ID NO:8).

Table 5 gives a complete restriction site analysis of pmTNF-MPH.

The presence of 6 successive histidines allows purification of the fusion protein by Immobilized Metal Ion Affinity Chromatography (IMAC).

To subclone the insert coding for p362 in pmTNF-MPH, it was set free from the construct in vector pUEX2 by EcoRI digestion. The EcoRI fragment (507 bp) was eluted from the gel, purified, blunted and inserted in the blunted XbaI site of pmTNF-MPH. The resulting recombinant plasmid, pmTNF-MPH-a362, is brought into E. coli strain K12ΔH (ATCC 33767) by transformation. After growth at 28° C., expression of the recombinant protein is induced by a temperature shift to 42° C., which is held on during 2 hours. Cells were harvested, centrifuged and lysed in French press.

The expressed fusion protein mTNF-H6-p362, present in the cytoplasm fraction of the E. coli recombinant, is purified by Immobilized Metal Ion Affinity Chromatography (IMAC) using conditions known by the man skilled in the art. The amino acid sequence of this complete fusion protein is represented in FIG. 10 (SEQ ID NO:9).

The purified fusion protein is used to coat 96-well microtitration plates, which were incubated with serial dilutions of sera from uninfected (control) and infected animals. Plate bound IgG were titrated with peroxydase-labeled rabbit anti-bovine IgG, as described in Materials and Methods.

What is claimed is:

1. A biologically pure polypeptide consisting of the amino acid sequence of SEQ ID NO 5, or a fragment thereof, wherein said fragment:

is recognized by antibodies also recognizing the sequence of SEQ ID NO 5, but the fragment is not recognized by antibodies raised against *M. bovis, M. avium, M. phlei* or *M. tuberculosis;* as an immunogen gives rise to antibodies which recognize the sequence of SEQ ID NO 5 but which do not recognize *M. bovis, M. avium, M. phlei* or *M. tuberculosis;* and reacts with the majority of sera from cattle suffering from Johne's disease.

2. An isolated polypeptide consisting of any of the following sequences:

the amino acid sequence of 101 amino acids of SEQ ID NO5,

Glu-Phe-Pro-Gly-Gly-Gln-Gln-His-Ser-Pro-Gln(SEQ ID NO 12), or

Gln-Gln-Ser-Tyr-Gly-Gln-Glu-Pro-Ser-Ser-Pro-Ser-Gly-Pro-Thr-Pro-Ala (SEQ ID NO 13).

3. A fusion protein comparing an amino acid sequence of the biologically pure polypeptide according to claim 1 and a heterologous amino acid sequence comprising from 1 to 1,100 amino acids.

4. A fusion protein consisting of the amino acid sequence represented in (SEQ ID NO 9).

5. An expression product expressed by cellular host transformed by a recombinant vector comprising regulating elements enabling the expression of a nucleic acid sequence encoding the polypeptide according to claim 1.

6. The expression product of claim 5, wherein the cellular host is a bacteria or a eukaryotic microorganism.

7. A method for the in virto diagnosis of paratuberculosis in an animal or of infection of an animal by *Mycobacterium paratuberculosis* comparing the steps of:

contacting a biological sample taken from said animal with a fusion protein according to claim 3, under conditions enabling an in vitro immunological reaction between said polypeptide and one or more antibodies recognizing said polypeptide, and decting in vitro the antigen/antibody complex which is formed, when paratuberculosis or infection by *Mycobacterium paratuberculosis* is present.

8. A method for in vitro diagnosis of Crohn's disease in a patient or infection of a patient by *Mycobacterium paratuberculosis* comprising the steps of:

contacting a bilogical sample taken from said patient with a fusion protein according to claim 3, under conditions enabling an in vitro immunological reaction between said polypeptide and one or more antibodies recognizing said polypeptide, and detecting in vitro the antigen/antibdy complex which has been formed, when Crohn's diseases or infection by *Mycobaterium paratuberculosis* is present.

9. An immunogenic composition comparing a fusion protein according to claim 3, and a pharmaceutically acceptable vehicle.

10. A method for in vitro diagnosis of paratuberculosis in an animal or of infection of an animal by *Mycobacterium paratuberculosis* comprising the steps of:

contacting a biological sample taken from said animal with a biologically pure polypeptide according to claim 1 under condition enabling an in vitro immunological reaction between said polypeptide and one or more antibodies recognizing said polypeptide, and decting in vitro the antigen/antibody complex which is formed, when paratuberculosis or infection by *Mycobacterium paratuberculosis* is present.

11. A method for in vitro diagnosis of Crohn's disease in a patient or infection of a patient by *Mycobacterium paratuberculosis* comprising the steps of:

contacting a biological sample taken from said patient with a biologically pure polypeptide according to claim 1 under conditions enabling an in vitro immunological reaction between said polypeptide and one or more antibodies recognizing said polpeptide, and detecting in vitro the antigen/antibody complex which has been formed, when Crohn's disease or infection by *Mycobacterium paratuberculosis* is present.

12. An immunogenic composition comprising a biologically pure polypeptide according to claim 1 and a pharmaceutically vehicle.

* * * * *

```
                         SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
          (A) LENGTH: 508 base pairs
          (B) TYPE: nucleic acid
          (C) STRANDEDNESS: double
          (D) TOPOLOGY: linear (ii) MOLECULE TYPE: DNA (genomic)

(vi) ORIGINAL SOURCE:
          (A) ORGANISM: Mycobacterium paratuberculosis (ix) FEATURE:
          (A) NAME/KEY: unsure
          (B) LOCATION: 35

(ix) FEATURE:
          (A) NAME/KEY: unsure
          (B) LOCATION: 185

(ix) FEATURE:
          (A) NAME/KEY: unsure
          (B) LOCATION: 252

(xi) SEQUENCE DESCRIPTION: SEQ ID NO:1:

GAATTCCCGG GTGGTCAGCA GCATTCGCCG CAGGNCTACG GGTCGCAGTA CGGCGGTTAC      60

GGCCAGGGCG GCGCTCCGAC CGGCGGTTTC GGTGCCCAGC CGTCGCCGCA GTCCGGCCCG     120

CAACAGTCCG CGCAGCAGCA GGGCCCGTCC ACACCGCCCA CCGGCTTCCC CAGCTTCAGC     180

CCGCNGCCCA ACGTCGGCGG GGGATCGGAC TCCGGTTCGG GGACCGCCAA TTACTCCGAG     240

CAGGCCGGTG GNCCAGCAGT CCTACGGCCA GGAGCCTTCT TCACCGTCTG GGCCGACGCC     300

CGCCTAACGT GCCCTGTCGC GCCTAGTCGG GAACGTGCCC CAGAGTGACA CGGGTGGAGG     360

ACAACCGGGC AGCGGGCGCT CGCCAGGCGC GTGACCTCGT CAGGGTCGCG TTCGCCCCGG     420

CGGTGGTGGC ACTGGTCATC ATCGCCGCGG TCACGCTGAT CCAGTTGTTG ATCGCCAACA     480

GCGACATGAC CGGCGCGTTG GGGAATTC                                        508

(2) INFORMATION FOR SEQ ID NO:2:

(i) SEQUENCE CHARACTERISTICS:
          (A) LENGTH: 507 base pairs
          (B) TYPE: nucleic acid
          (C) STRANDEDNESS: double
          (D) TOPOLOGY: linear
```

-continued

```
    (ii) MOLECULE TYPE: DNA (genomic)

(vi) ORIGINAL SOURCE:
         (A) ORGANISM: Mycobacterium paratuberculosis (xi) SEQUENCE DESCRIPTION: SEQ ID NO:2:

GAATTCCCGG GTGGTCAGCA GCATTCGCCG CAGGCTACGG GTCGCAGTAC GGCGGTTACG      60

GCCAGGGCGG CGCTCCGACC GGCGGTTTCG GTGCCCAGCC GTCGCCGCAG TCCGGCCCGC     120

AACAGTCCGC GCAGCAGCAG GGCCCGTCCA CACCGCCCAC CGGCTTCCCC AGCTTCAGCC     180

CGCGGCCCAA CGTCGGCGGG GGATCGGACT CCGGTTCGGC GACCGCCAAT TACTCCGAGC     240

AGGCCGGTGG CCCAGCAGTC CTACGGCCAG GAGCCTTCTT CACCGTCTGG GCCGACGCCC     300

GCCTAACGTG CCCTGTCGCG CCTAGTCGGG AACGTGCCCC AGAGTGACAC GGGTGGAGGA     360

CAACCGGGCA GCGGGCGCTC GCCAGGCGCG TGACCTCGTC AGGGTCGCGT TCGCCCCGGC     420

GGTGGTGGCA CTGGTCATCA TCGCCGCGGT CACGCTGATC CAGTTGTTGA TCGCCAACAG     480

CGACATGACC GGCGCGTTGG GGAATTC                                        507

(2) INFORMATION FOR SEQ ID NO:3:

(i) SEQUENCE CHARACTERISTICS:
        (A) LENGTH: 507 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
         (A) ORGANISM: Mycobacterium paratuberculosis (xi) SEQUENCE DESCRIPTION: SEQ ID NO:3:

GAATTCCCGG GTGGTCAGCA GCATTCGCCG CAGGGCTACG GGTCGCAGTA CGGCGGTTAC      60

GGCCAGGGCG GCGCTCCGAC CGGCGGTTTC GGTGCCCAGC CGTCGCCGCA GTCCGGCCCG     120

CAACAGTCCG CGCAGCAGCA GGGCCCGTCC ACACCGCCCA CCGGCTTCCC CAGCTTCAGC     180

CCGCCGCCCA ACGTCGGCGG GGGATCGGAC TCCGGTTCGG CGACCGCCAA TTACTCCGAG     240

CAGGCCGGTG GCCAGCAGTC CTACGGCCAG GAGCCTTCTT CACCGTCTGG GCCGACGCCC     300

GCCTAACGTG CCCTGTCGCG CCTAGTCGGG AACGTGCCCC AGAGTGACAC GGGTGGAGGA     360

CAACCGGGCA GCGGGCGCTC GCCAGGCGCG TGACCTCGTC AGGGTCGCGT TCGCCCCGGC     420

GGTGGTGGCA CTGGTCATCA TCGCCGCGGT CACGCTGATC CAGTTGTTGA TCGCCAACAG     480

CGACATGACC GGCGCGTTGG GGAATTC                                        507

(2) INFORMATION FOR SEQ ID NO:4:

(i) SEQUENCE CHARACTERISTICS:
        (A) LENGTH: 306 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Mycobacterium paratuberculosis (ix) FEATURE:
         (A) NAME/KEY: CDS
         (B) LOCATION: 1..306

(ix) FEATURE:
         (A) NAME/KEY: mat_peptide
```

(B) LOCATION: 1..303

(xi) SEQUENCE DESCRIPTION: SEQ ID NO:4:

```
GAA TTC CCG GGT GGT CAG CAG CAT TCG CCG CAG GGC TAC GGG TCG CAG        48
Glu Phe Pro Gly Gly Gln Gln His Ser Pro Gln Gly Tyr Gly Ser Gln
  1               5                  10                  15

TAC GGC GGT TAC GGC CAG GGC GGC GCT CCG ACC GGC GGT TTC GGT GCC        96
Tyr Gly Gly Tyr Gly Gln Gly Gly Ala Pro Thr Gly Gly Phe Gly Ala
             20                  25                  30

CAG CCG TCG CCG CAG TCC GGC CCG CAA CAG TCC GCG CAG CAG CAG GGC       144
Gln Pro Ser Pro Gln Ser Gly Pro Gln Gln Ser Ala Gln Gln Gln Gly
         35                  40                  45

CCG TCC AGA CCG CCC ACC GGC TTC CCC AGC TTC AGC CCG CCG CCC AAC       192
Pro Ser Arg Pro Pro Thr Gly Phe Pro Ser Phe Ser Pro Pro Pro Asn
     50                  55                  60

GTC GGC GGG GGA TCG GAC TCC GGT TCG GCG ACC GCC AAT TAC TCC GAG       240
Val Gly Gly Gly Ser Asp Ser Gly Ser Ala Thr Ala Asn Tyr Ser Glu
 65                  70                  75                  80

CAG GCC GGT GGC CAG CAG TCC TAC GGC CAG GAG CCT TCT TCA CCG TCT       288
Gln Ala Gly Gly Gln Gln Ser Tyr Gly Gln Glu Pro Ser Ser Pro Ser
                 85                  90                  95

GGG CCG ACG CCC GCC TAA                                                306
Gly Pro Thr Pro Ala
            100
```

(2) INFORMATION FOR SEQ ID NO:5:

(i) SEQUENCE CHARACTERISTICS:
        (A) LENGTH: 101 amino acids
        (B) TYPE: amino acid
        (D) TOPOLOGY: linear (ii) MOLECULE TYPE: protein (xi) SEQUENCE DESCRIPTION: SEQ ID NO:5:

```
Glu Phe Pro Gly Gly Gln Gln His Ser Pro Gln Gly Tyr Gly Ser Gln
  1               5                  10                  15

Tyr Gly Gly Tyr Gly Gln Gly Gly Ala Pro Thr Gly Gly Phe Gly Ala
             20                  25                  30

Gln Pro Ser Pro Gln Ser Gly Pro Gln Gln Ser Ala Gln Gln Gln Gly
         35                  40                  45

Pro Ser Arg Pro Pro Thr Gly Phe Pro Ser Phe Ser Pro Pro Pro Asn
     50                  55                  60

Val Gly Gly Gly Ser Asp Ser Gly Ser Ala Thr Ala Asn Tyr Ser Glu
 65                  70                  75                  80

Gln Ala Gly Gly Gln Gln Ser Tyr Gly Gln Glu Pro Ser Ser Pro Ser
                 85                  90                  95

Gly Pro Thr Pro Ala
            100
```

(2) INFORMATION FOR SEQ ID NO:6:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Mycobacterium paratuberculosis (ix) FEATURE:
            (A) NAME/KEY: CDS
            (B) LOCATION: 1..60

(ix) FEATURE:
            (A) NAME/KEY: mat_peptide
            (B) LOCATION: 1..57

(xi) SEQUENCE DESCRIPTION: SEQ ID NO:6:

```
CAG GGA ATT CAC CAT CAC CAT CAC CAC GTG GAT CCC GGG CCC ATG GCT        48
Gln Gly Ile His His His His His His Val Asp Pro Gly Pro Met Ala
  1               5                  10                  15

TTC CGG AGG CCT                                                          60
Phe Arg Arg Pro
            20
```

(2) INFORMATION FOR SEQ ID NO:7:

(i) SEQUENCE CHARACTERISTICS:
            (A) LENGTH: 20 amino acids
            (B) TYPE: amino acid
            (D) TOPOLOGY: linear (ii) MOLECULE TYPE: protein (xi) SEQUENCE DESCRIPTION: SEQ ID NO:7:

```
Gln Gly Ile His His His His His His Val Asp Pro Gly Pro Met Ala
  1               5                  10                  15

Phe Arg Arg Pro
            20
```

(2) INFORMATION FOR SEQ ID NO:8:

(i) SEQUENCE CHARACTERISTICS:
            (A) LENGTH: 3474 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:8:

```
AATTCCGGGG ATCTCTCACC TACCAAACAA TGCCCCCCTG CAAAAAATAA ATTCATATAA        60

AAAACATACA GATAACCATC TGCGGTGATA AATTATCTCT GGCGGTGTTG ACATAAATAC       120

CACTGGCGGT GATACTGAGC ACATCAGCAG GACGCACTGA CCACCATGAA GGTGACGCTC       180

TTAAAAATTA AGCCCTGAAG AAGGGCAGGG GTACCAGGAG GTTTAAATCA TGGTAAGATC       240

AAGTAGTCAA AATTCGAGTG ACAAGCCTGT AGCCCACGTC GTAGCAAACC ACCAAGTGGA       300

GGAGCAGGGA ATTCACCATC ACCATCACCA CGTGGATCCC GGGCCCATGG CTTTCCGGAG       360

GCCTCTAGAG TCGACCGGCA TGCAAGCTTA AGTAAGTAAG CCGCCAGTTC CGCTGGCGGC       420

ATTTTNNTTG ATGCCCAAGC TTGGCTGTTT TGGCGGATGA GAAGATTT TCAGCCTGAT         480

ACAGATTAAA TCAGAACGCA GAAGCGGTCT GATAAAACAG AATTTGCCTG GCGGCAGTAG       540

CGCGGTGGTC CCACCTGACC CCATGCCGAA CTCAGAAGTG AAACGCCGTA GCGCCGATGG       600

TAGTGTGGGG TCTCCCCATG CGAGAGTAGG GAACTGCCAG GCATCAAATA AAACGAAAGG       660

CTCAGTCGAA AGACTGGGCC TTTCGTTTTA TCTGTTGTTT GTCGGTGAAC GCTCTCCTGA       720

GTAGGACAAA TCCGCCGGGA GCGGATTTGA ACGTTGCGAA GCAACGGCCC GGAGGGTGGC       780

GGGCAGGACG CCCGCCATAA ACTGCCAGGC ATCAAATTAA GCAGAAGGCC ATCCTGACGG       840

ATGGCCTTTT TGCGTTTCTA CAAACTCTTT TGTTTATTTT TCTAAATACA TTCAAATATG       900
```

```
TATCCGCTCA TGAGACAATA ACCCTGATAA ATGCTTCAAT AATAAAAGGA TCTAGGTGAA    960

GTCCTTTTTG ATAATCTCAT GACCAAAATC CCTTAACGTG AGTTTTCGTT CCACTGAGCG   1020

TTCAGACCCC GTAGAAAAGA TCAAAGGATC TTCTTGAGAT CCTTTTTTTC TGCGCGTAAT   1080

CTGCTGCTTG CAAACAAAAA AACCACCGCT ACCAGCGGTG GTTTGTTTGC CGGATCAAGA   1140

GCTACCAACT CTTTTTCCGA AGGTAACTGG CTTCAGCAGA GCGCAGATAC CAAATACTGT   1200

CCTTCTAGTG TAGCCGTAGT TAGGCCACCA CTTCAAGAAC TCTGTAGCAC CGCCTACATA   1260

CCTCGCTCTG CTAATCCTGT TACCAGTGGC TGCTGCCAGT GGCGATAAGT CGTGTCTTAC   1320

CGGGTTGGAC TCAAGACGAT AGTTACCGGA TAAGGCGCAG CGGTCGGGCT GAACGGGGGG   1380

TTCGTGCACA CAGCCCAGCT TGGAGCGAAC GACCTACACC GAACTGAGAT ACCTACAGCG   1440

TGAGCATTGA GAAAGCGCCA CGCTTCCCGA AGGGAGAAAG GCGGACAGGT ATCCGGTAAG   1500

CGGCAGGGTC GGAACAGGAG AGCGCACGAG GGAGCTTCCA GGGGGAAACG CCTGGTATCT   1560

TTATAGTCCT GTCGGGTTTC GCCACCTCTG ACTTGAGCGT CGATTTTTGT GATGCTCGTC   1620

AGGGGGGCGG AGCCTATGGA AAAACGCCAG CAACGCGGCC TTTTTACGGT TCCTGGCCTT   1680

TTGCTGGCCT TTTGCTCACA TGTTCTTTCC TGCGTTATCC CCTGATTCTG TGGATAACCG   1740

TATTACCGCC TTTGAGTGAG CTGATACCGC TCGCCGCAGC CGAACGACCG AGCGCAGCGA   1800

GTCAGTGAGC GAGGAAGCGG AAGAGCGCTG ACTTCCGCGT TTCCAGACTT TACGAAACAC   1860

GGAAACCGAA GACCATTCAT GTTGTTGCTC AGGTCGCAGA CGTTTTGCAG CAGCAGTCGC   1920

TTCACGTTCG CTCGCGTATC GGTGATTCAT TCTGCTAACC AGTAAGGCAA CCCCGCCAGC   1980

CTAGCCGGGT CCTCAACGAC AGGAGCACGA TCATGCGCAC CCGTGGCCAG GACCCAACGC   2040

TGCCCGAGAT GCGCCGCGTG CGGCTGCTGG AGATGGCGGA CGCGATGGAT ATGTTCTGCC   2100

AAGGGTTGGT TTGCGCATTC ACAGTTCTCC GCAAGAATTG ATTGGCTCCA ATTCTTGGAG   2160

TGGTGAATCC GTTAGCGAGG TGCCGCCGGC TTCCATTCAG GTCGAGGTGG CCCGGCTCCA   2220

TGCACCGCGA CGCAACGCGG GGAGGCAGAC AAGGTATAGG GCGGCGCCTA CAATCCATGC   2280

CAACCCGTTC CATGTGCTCG CCGAGGCGGC ATAAATCGCC GTGACGATCA GCGGTCCAGT   2340

GATCGAAGTT AGGCTGGTAA GAGCCGCGAG CGATCCTTGA AGCTGTCCCT GATGGTCGTC   2400

ATCTACCTGC CTGGACAGCA TGGCCTGCAA CGCGGGCATC CCGATGCCGC CGGAAGCGAG   2460

AAGAATCATA ATGGGGAAGG CCATCCAGCC TCGCGTCGCG AACGCCAGCA AGACGTAGCC   2520

CAGCGCGTCG GCCGCCATGC CGGCGATAAT GGCCTGCTTC TCGCCGAAAC GTTTGGTGGC   2580

GGGACCAGTG ACGAAGGCTT GAGCGAGGGC GTGCAAGATT CCGAATACCG CAAGCGACAG   2640

GCCGATCATC GTCGCGCTCC AGCGAAAGCG GTCCTCGCCG AAAATGACCC AGAGCGCTGC   2700

CGGCACCTGT CCTACGAGTT GCATGATAAA GAAGACAGTC ATAAGTGCGG CGACGATAGT   2760

CATGCCCCGC GCCCACCGGA AGGAGCTGAC TGGGTTGAAG GCTCTCAAGG GCATCGGTCG   2820

ACGCTCTCCC TTATGCGACT CCTGCATTAG GAAGCAGCCC AGTAGTAGGT TGAGGCCGTT   2880

GAGCACCGCC GCCGCAAGGA ATGGTGCATG CAAGGAGATG GCGCCCAACA GTCCCCCGGC   2940

CACGGGGCCT GCCACCATAC CCACGCCGAA ACAAGCGCTC ATGAGCCCGA AGTGGCGAGC   3000

CCGATCTTCC CCATCGGTGA TGTCGGCGAT ATAGGCGCCA GCAACCGCAC CTGTGGCGCC   3060

GGTGATGCCG GCCACGATGC GTCCGGCGTA GAGGATCCAC AGGACGGGTG TGGTCGCCAT   3120

GATCGCGTAG TCGATAGTGG CTCCAAGTAG CGAAGCGAGC AGGACTGGGC GGCGGCCAAA   3180

GCGGTCGGAC AGTGCTCCGA GAACGGGTGC GCATAGAAAT TGCATCAACG CATATAGCGC   3240

TAGCAGCACG CCATAGTGAC TGGCGATGCT GTCGGAATGG ACGATATCCC GCAAGAGGCC   3300
```

```
CGGCAGTACC GGCATAACCA AGCCTATGCC TACAGCATCC AGGGTGACGG TGCCGAGGAT    3360

GACGATGAGC GCATTGTTAG ATTTCATACA CGGTGCCTGA CTGCGTTAGC AATTTAACTG    3420

TGATAAACTA CCGCATTAAA GCTTATCGAT GATAAGCTGT CAAACATGAG AATT          3474
```

(2) INFORMATION FOR SEQ ID NO:9:

(i) SEQUENCE CHARACTERISTICS:
        (A) LENGTH: 147 amino acids
        (B) TYPE: amino acid
        (D) TOPOLOGY: linear (ii) MOLECULE TYPE: peptide (xi) SEQUENCE DESCRIPTION: SEQ ID NO:9:

```
Met Val Arg Ser Ser Gln Asn Ser Ser Asp Lys Pro Val Ala His
1               5                   10                  15

Val Val Ala Asn His Gln Val Glu Glu Gln Gly Ile His His His His
            20                  25                  30

His His Val Asp Pro Gly Pro Met Ala Phe Arg Arg Pro Leu Glu Phe
        35                  40                  45

Pro Gly Gly Gln Gln His Ser Pro Gln Gly Tyr Gly Ser Gln Tyr Gly
    50                  55                  60

Gly Tyr Gly Gln Gly Gly Ala Pro Thr Gly Gly Phe Gly Ala Gln Pro
65              70                  75                  80

Ser Pro Gln Ser Gly Pro Gln Gln Ser Ala Gln Gln Gly Pro Ser
                85                  90                  95

Thr Pro Pro Thr Gly Phe Pro Ser Phe Ser Pro Pro Asn Val Gly
            100                 105                 110

Gly Gly Ser Asp Ser Gly Ser Ala Thr Ala Asn Tyr Ser Glu Gln Ala
        115                 120                 125

Gly Gly Gln Gln Ser Tyr Gly Gln Glu Pro Ser Ser Pro Ser Gly Pro
    130                 135                 140

Thr Pro Ala
145
```

(2) INFORMATION FOR SEQ ID NO:10:

(i) SEQUENCE CHARACTERISTICS:
        (A) LENGTH: 1839 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Mycobacterium paratuberculosis (ix) FEATURE:
        (A) NAME/KEY: CDS
        (B) LOCATION: 742..1638

(ix) FEATURE:
        (A) NAME/KEY: mat_peptide
        (B) LOCATION: 742..1635

(xi) SEQUENCE DESCRIPTION: SEQ ID NO:10:

```
GGGCCCGAAC TTGACGAACT CGCCGTCGTA GCTGGCTTCC TCGTCGGTCC ACAGCGCCCG    60

CATCGCTTCC AGGTATTCGC GCAGCATGGT GCGGCGCCGG CCCGCCGGCA CGCCGTGGTC   120

GGCGAGTTCG TCGGTGTTCC AGCCGAACCC GACGCCGAGG CTGACCCGGC CGCCGGACAG   180
```

-continued

```
ATGGTCAAGG GTGGCAATAC TTTTCGCCAG CGTGATCGGG TCGTGTTCGA CCGGCAGGGC    240

CAGCGCGGTG GACAGCCGCA CCCGCGAGGT GACGGCACAG GCCGCGCCCA GACTGACCCA    300

CGGGTCCAGG GTGCGCATGT AGCGGTCGTC GGGCAGCGAC GCGTCGCCGG TGGTCGGGTG    360

CGCGGCCTCC CGCTTGATCG GGATATGCGT GTGTTCCGGC ACGTAGAAGG TCGCAAACCC    420

GTGGTCGTCG GCAAGCTTCG CGGCCGCAGC CGGAGAGATG CCACGGTCGC TGGTGAAAAG    480

CACAAGCCCG TAATCCATGC AGTGAATTAG AACGTGTTCT ACCTCTGCGG GGCAAGCTGT    540

CGTGATACGG ACCGTCTCGC CGCGCGGTCG TCTGCGAAGC CCGCGGGCAA GCCAATGGCG    600

ACGGCACCGG CCGTCGCACG TGCGCTAGCG TGGGTGATCG ACCGTGTCGC TCGCGCAGTG    660

ACGCGCCTGC AAGCACCGCG TCGCATCGCA ACCGTGGCGC CCGCTCGGCA CTAAAAGGCA    720
```

| | | | |
|---|---|---|---|
| GTGGAAGCAA CAGGAGGAGC C ATG ACC TAC TCT CCC GGC AGC CCC GGA TAT | | | 771 |
| Met Thr Tyr Ser Pro Gly Ser Pro Gly Tyr | | | |
| 1 5 10 | | | |

| CCA CCG GCG CAG TCT GGC GGC ACC TAT GCA GGC GCC ACA CCA TCT TTC | 819 |
|---|---|
| Pro Pro Ala Gln Ser Gly Gly Thr Tyr Ala Gly Ala Thr Pro Ser Phe | |
| 15 20 25 | |

| GCC AAA GAC GAC GAC GGC AAG AGC AAA CTC CCG CTC TAC CTC AAC ATC | 867 |
|---|---|
| Ala Lys Asp Asp Asp Gly Lys Ser Lys Leu Pro Leu Tyr Leu Asn Ile | |
| 30 35 40 | |

| GCC GTG GTC GCC CTG GGT TTC GCG GCC TAC CTG CTG AAT TTC GGC CCC | 915 |
|---|---|
| Ala Val Val Ala Leu Gly Phe Ala Ala Tyr Leu Leu Asn Phe Gly Pro | |
| 45 50 55 | |

| ACC TTC ACC ATC GGC GCC GAC CTC GGC CCG GGT ATC GGC GGC CGC GCG | 963 |
|---|---|
| Thr Phe Thr Ile Gly Ala Asp Leu Gly Pro Gly Ile Gly Gly Arg Ala | |
| 60 65 70 | |

| GGT GAC GCC GGC ACC GCC GTC GTG GTG GCG CTG CTG GCC GCG CTG CTC | 1011 |
|---|---|
| Gly Asp Ala Gly Thr Ala Val Val Val Ala Leu Leu Ala Ala Leu Leu | |
| 75 80 85 90 | |

| GCC GGG CTG GGC CTG CTG CCC AAG GCC AAG AGT TAT GTG GGC GTG GTC | 1059 |
|---|---|
| Ala Gly Leu Gly Leu Leu Pro Lys Ala Lys Ser Tyr Val Gly Val Val | |
| 95 100 105 | |

| GCG GTC GTC GCG GTC CTC GCC GCG CTG CTG GCC ATC ACC GAG ACG ATC | 1107 |
|---|---|
| Ala Val Val Ala Val Leu Ala Ala Leu Leu Ala Ile Thr Glu Thr Ile | |
| 110 115 120 | |

| AAC CTG CCC GCC GGT TTC GCG ATC GGC TGG GCG ATG TGG CCG CTG GTG | 1155 |
|---|---|
| Asn Leu Pro Ala Gly Phe Ala Ile Gly Trp Ala Met Trp Pro Leu Val | |
| 125 130 135 | |

| GCG TGC GTG GTG CTG CAG GCG ATC GCC GCG GTG GTC GTG GTC CTG CTG | 1203 |
|---|---|
| Ala Cys Val Val Leu Gln Ala Ile Ala Ala Val Val Val Val Leu Leu | |
| 140 145 150 | |

| GAC GCC GGG GTG ATC ACG GCG CCG GCG CCG CGG CCC AAG TAC GAC CCC | 1251 |
|---|---|
| Asp Ala Gly Val Ile Thr Ala Pro Ala Pro Arg Pro Lys Tyr Asp Pro | |
| 155 160 165 170 | |

| TAC GCG CAG TAC GGC CAA TAC GGG CAA TAC GGC CAG TAC GGG CAA CAG | 1299 |
|---|---|
| Tyr Ala Gln Tyr Gly Gln Tyr Gly Gln Tyr Gly Gln Tyr Gly Gln Gln | |
| 175 180 185 | |

| CCC TAC TAC GGT CAG CCG GGC GGT CAG CCC GGG GGC CAG CCG GGT GGT | 1347 |
|---|---|
| Pro Tyr Tyr Gly Gln Pro Gly Gly Gln Pro Gly Gly Gln Pro Gly Gly | |
| 190 195 200 | |

| CAG CAG CAT TCG CCG CAG GGC TAC GGG TCG CAG TAC GGC GGT TAC GGC | 1395 |
|---|---|
| Gln Gln His Ser Pro Gln Gly Tyr Gly Ser Gln Tyr Gly Gly Tyr Gly | |
| 205 210 215 | |

| CAG GGC GGC GCT CCG ACC GGC GGT TTC GGT GCC CAG CCG TCG CCG CAG | 1443 |
|---|---|
| Gln Gly Gly Ala Pro Thr Gly Gly Phe Gly Ala Gln Pro Ser Pro Gln | |
| 220 225 230 | |

| TCC GGC CCG CAA CAG TCC GCG CAG CAG CAG GGC CCG TCC ACA CCG CCC | 1491 |
|---|---|

```
Ser Gly Pro Gln Gln Ser Ala Gln Gln Gln Gly Pro Ser Thr Pro Pro
235                 240                 245                 250

ACC GGC TTC CCC AGC TTC AGC CCG CCG CCC AAC GTC GGC GGG GGA TCG    1539
Thr Gly Phe Pro Ser Phe Ser Pro Pro Pro Asn Val Gly Gly Gly Ser
                    255                 260                 265

GAC TCC GGT TCG GCG ACC GCC AAT TAC TCC GAG CAG GCC GGT GGC CAG    1587
Asp Ser Gly Ser Ala Thr Ala Asn Tyr Ser Glu Gln Ala Gly Gly Gln
                270                 275                 280

CAG TCC TAC GGC CAG GAG CCT TCT TCA CCG TCT GGG CCG ACG CCC GCC    1635
Gln Ser Tyr Gly Gln Glu Pro Ser Ser Pro Ser Gly Pro Thr Pro Ala
            285                 290                 295

TAACGTGCCC TGTCGCGCCT AGTCGGGAAC GTGCCCAGA GTGACACGGG TGGAGGACAA   1695

CCGGGCAGCG GGCGCTCGCC AGGCGCGTGA CCTCGTCAGG GTCGCGTTCG CCCCGGCGGT  1755

GGTGGCACTG GTCATCATCG CCGCGGTCAC GCTGATCCAG TTGTTGATCG CCAACAGCGA  1815

CATGACCGGC GCGTTGGGGA ATTC                                        1839

(2) INFORMATION FOR SEQ ID NO:11:

(i) SEQUENCE CHARACTERISTICS:
        (A) LENGTH: 298 amino acids
        (B) TYPE: amino acid
        (D) TOPOLOGY: linear (ii) MOLECULE TYPE: protein (xi) SEQUENCE DESCRIPTION: SEQ ID NO:11:

Met Thr Tyr Ser Pro Gly Ser Pro Gly Tyr Pro Pro Ala Gln Ser Gly
 1               5                  10                  15

Gly Thr Tyr Ala Gly Ala Thr Pro Ser Phe Ala Lys Asp Asp Asp Gly
                20                  25                  30

Lys Ser Lys Leu Pro Leu Tyr Leu Asn Ile Ala Val Val Ala Leu Gly
            35                  40                  45

Phe Ala Ala Tyr Leu Leu Asn Phe Gly Pro Thr Phe Thr Ile Gly Ala
    50                  55                  60

Asp Leu Gly Pro Gly Ile Gly Gly Arg Ala Gly Asp Ala Gly Thr Ala
65                  70                  75                  80

Val Val Val Ala Leu Leu Ala Ala Leu Leu Ala Gly Leu Gly Leu Leu
                85                  90                  95

Pro Lys Ala Lys Ser Tyr Val Gly Val Val Ala Val Val Ala Val Leu
                100                 105                 110

Ala Ala Leu Leu Ala Ile Thr Glu Thr Ile Asn Leu Pro Ala Gly Phe
            115                 120                 125

Ala Ile Gly Trp Ala Met Trp Pro Leu Val Ala Cys Val Val Leu Gln
    130                 135                 140

Ala Ile Ala Ala Val Val Val Leu Leu Asp Ala Gly Val Ile Thr
145                 150                 155                 160

Ala Pro Ala Pro Arg Pro Lys Tyr Asp Pro Tyr Ala Gln Tyr Gly Gln
                165                 170                 175

Tyr Gly Gln Tyr Gly Gln Tyr Gly Gln Gln Pro Tyr Tyr Gly Gln Pro
                180                 185                 190

Gly Gly Gln Pro Gly Gly Gln Pro Gly Gly Gln Gln His Ser Pro Gln
            195                 200                 205

Gly Tyr Gly Ser Gln Tyr Gly Gly Tyr Gly Gln Gly Ala Pro Thr
    210                 215                 220

Gly Gly Phe Gly Ala Gln Pro Ser Pro Gln Ser Gly Pro Gln Gln Ser
225                 230                 235                 240
```

Ala Gln Gln Gln Gly Pro Ser Thr Pro Pro Thr Gly Phe Pro Ser Phe
                245                 250                 255

Ser Pro Pro Pro Asn Val Gly Gly Gly Ser Asp Ser Gly Ser Ala Thr
            260                 265                 270

Ala Asn Tyr Ser Glu Gln Ala Gly Gly Gln Gln Ser Tyr Gly Gln Glu
        275                 280                 285

Pro Ser Ser Pro Ser Gly Pro Thr Pro Ala
    290                 295

(2) INFORMATION FOR SEQ ID NO:12:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:12:

Glu Phe Pro Gly Gly Gln Gln His Ser Pro Gln
1               5                   10

(2) INFORMATION FOR SEQ ID NO:13:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:13:

Gln Gln Ser Tyr Gly Gln Glu Pro Ser Ser Pro Ser Gly Pro Thr Pro
1               5                   10                  15
Ala (2) INFORMATION FOR SEQ ID NO:14:

(i) SEQUENCE CHARACTERISTICS:
        (A) LENGTH: 307 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:14:

```
GAATTCCCGG GTGGTCAGCA GCATTCGCCG CAGGNCTACG GGTCGCAGTA CGGCGGTTAC      60

GGCCAGGGCG GCGCTCCGAC CGGCGGTTTC GGTGCCCAGC CGTCGCCGCA GTCCGGCCCG     120

CAACAGTCCG CGCAGCAGCA GGGCCCGTCC ACACCGCCCA CCGGCTTCCC CAGCTTCAGC     180

CCGCNGCCCA ACGTCGGCGG GGGATCGGAC TCCGGTTCGG GGACCGCCAA TTACTCCGAG     240

CAGGCCGGTG GNCCAGCAGT CCTACGGCCA GGAGCCTTCT TCACCGTCTG GGCCGACGCC     300

CGCCTAA                                                               307
```

(2) INFORMATION FOR SEQ ID NO:15:

(i) SEQUENCE CHARACTERISTICS:
        (A) LENGTH: 306 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:15:

```
GAATTCCCGG GTGGTCAGCA GCATTCGCCG CAGGCTACGG GTCGCAGTAC GGCGGTTACG      60
GCCAGGGCGG CGCTCCGACC GGCGGTTTCG GTGCCCAGCC GTCGCCGCAG TCCGGCCCGC     120
AACAGTCCGC GCAGCAGCAG GGCCCGTCCA CACCGCCCAC CGGCTTCCCC AGCTTCAGCC     180
CGCGGCCCAA CGTCGGCGGG GGATCGGACT CCGGTTCGGC GACCGCCAAT TACTCCGAGC     240
AGGCCGGTGG CCCAGCAGTC CTACGGCCAG GAGCCTTCTT CACCGTCTGG GCCGACGCCC     300
GCCTAA                                                                306
```

(2) INFORMATION FOR SEQ ID NO:16:

(i) SEQUENCE CHARACTERISTICS:
        (A) LENGTH: 306 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:16:

```
GAATTCCCGG GTGGTCAGCA GCATTCGCCG CAGGGCTACG GGTCGCAGTA CGGCGGTTAC      60
GGCCAGGGCG GCGCTCCGAC CGGCGGTTTC GGTGCCCAGC CGTCGCCGCA GTCCGGCCCG     120
CAACAGTCCG CGCAGCAGCA GGGCCCGTCC ACACCGCCCA CCGGCTTCCC CAGCTTCAGC     180
CCGCCGCCCA ACGTCGGCGG GGGATCGGAC TCCGGTTCGG CGACCGCCAA TTACTCCGAG     240
CAGGCCGGTG CCAGCAGTC CTACGGCCAG GAGCCTTCTT CACCGTCTGG GCCGACGCCC     300
GCCTAA                                                                306
```

(2) INFORMATION FOR SEQ ID NO:17:

(i) SEQUENCE CHARACTERISTICS:
        (A) LENGTH: 597 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..597

(xi) SEQUENCE DESCRIPTION: SEQ ID NO:17:

```
ATG ACC TAC TCT CCC GGC AGC CCC GGA TAT CCA CCG GCG CAG TCT GGC       48
Met Thr Tyr Ser Pro Gly Ser Pro Gly Tyr Pro Pro Ala Gln Ser Gly
  1               5                  10                  15

GGC ACC TAT GCA GGC GCC ACA CCA TCT TTC GCC AAA GAC GAC GAC GGC       96
Gly Thr Tyr Ala Gly Ala Thr Pro Ser Phe Ala Lys Asp Asp Asp Gly
             20                  25                  30

AAG AGC AAA CTC CCG CTC TAC CTC AAC ATC GCC GTG GTC GCC CTG GGT      144
Lys Ser Lys Leu Pro Leu Tyr Leu Asn Ile Ala Val Val Ala Leu Gly
         35                  40                  45

TTC GCG GCC TAC CTG CTG AAT TTC GGC CCC ACC TTC ACC ATC GGC GCC      192
Phe Ala Ala Tyr Leu Leu Asn Phe Gly Pro Thr Phe Thr Ile Gly Ala
     50                  55                  60

GAC CTC GGC CCG GGT ATC GGC GGC CGC GCG GGT GAC GCC GGC ACC GCC      240
Asp Leu Gly Pro Gly Ile Gly Gly Arg Ala Gly Asp Ala Gly Thr Ala
 65                  70                  75                  80

GTC GTG GTG GCG CTG CTG GCC GCG CTG CTC GCC GGG CTG GGC CTG CTG      288
```

```
Val Val Val Ala Leu Leu Ala Ala Leu Leu Ala Gly Leu Gly Leu Leu
                85                  90                  95

CCC AAG GCC AAG AGT TAT GTG GGC GTG GTC GCG GTC GTC GCG GTC CTC    336
Pro Lys Ala Lys Ser Tyr Val Gly Val Val Ala Val Val Ala Val Leu
            100                 105                 110

GCC GCG CTG CTG GCC ATC ACC GAG ACG ATC AAC CTG CCC GCC GGT TTC    384
Ala Ala Leu Leu Ala Ile Thr Glu Thr Ile Asn Leu Pro Ala Gly Phe
        115                 120                 125

GCG ATC GGC TGG GCG ATG TGG CCG CTG GTG GCG TGC GTG GTG CTG CAG    432
Ala Ile Gly Trp Ala Met Trp Pro Leu Val Ala Cys Val Val Leu Gln
    130                 135                 140

GCG ATC GCC GCG GTG GTC GTG GTC CTG CTG GAC GCC GGG GTG ATC ACG    480
Ala Ile Ala Ala Val Val Val Val Leu Leu Asp Ala Gly Val Ile Thr
145                 150                 155                 160

GCG CCG GCG CCG CGG CCC AAG TAC GAC CCC TAC GCG CAG TAC GGC CAA    528
Ala Pro Ala Pro Arg Pro Lys Tyr Asp Pro Tyr Ala Gln Tyr Gly Gln
                165                 170                 175

TAC GGG CAA TAC GGC CAG TAC GGG CAA CAG CCC TAC TAC GGT CAG CCG    576
Tyr Gly Gln Tyr Gly Gln Tyr Gly Gln Gln Pro Tyr Tyr Gly Gln Pro
            180                 185                 190

GGC GGT CAG CCC GGG GGC CAG                                         597
Gly Gly Gln Pro Gly Gly Gln
        195

(2) INFORMATION FOR SEQ ID NO:18:

(i) SEQUENCE CHARACTERISTICS:
        (A) LENGTH: 199 amino acids
        (B) TYPE: amino acid
        (D) TOPOLOGY: linear (ii) MOLECULE TYPE: protein (xi) SEQUENCE DESCRIPTION: SEQ ID NO:18:

Met Thr Tyr Ser Pro Gly Ser Pro Gly Tyr Pro Pro Ala Gln Ser Gly
  1               5                  10                  15

Gly Thr Tyr Ala Gly Ala Thr Pro Ser Phe Ala Lys Asp Asp Asp Gly
                20                  25                  30

Lys Ser Lys Leu Pro Leu Tyr Leu Asn Ile Ala Val Val Ala Leu Gly
            35                  40                  45

Phe Ala Ala Tyr Leu Leu Asn Phe Gly Pro Thr Phe Thr Ile Gly Ala
        50                  55                  60

Asp Leu Gly Pro Gly Ile Gly Gly Arg Ala Gly Asp Ala Gly Thr Ala
65                  70                  75                  80

Val Val Val Ala Leu Leu Ala Ala Leu Leu Ala Gly Leu Gly Leu Leu
                85                  90                  95

Pro Lys Ala Lys Ser Tyr Val Gly Val Val Ala Val Val Ala Val Leu
            100                 105                 110

Ala Ala Leu Leu Ala Ile Thr Glu Thr Ile Asn Leu Pro Ala Gly Phe
        115                 120                 125

Ala Ile Gly Trp Ala Met Trp Pro Leu Val Ala Cys Val Val Leu Gln
    130                 135                 140

Ala Ile Ala Ala Val Val Val Val Leu Leu Asp Ala Gly Val Ile Thr
145                 150                 155                 160
```

-continued

```
Ala Pro Ala Pro Arg Pro Lys Tyr Asp Pro Tyr Ala Gln Tyr Gly Gln
                165                 170                 175

Tyr Gly Gln Tyr Gly Gln Tyr Gly Gln Gln Pro Tyr Tyr Gly Gln Pro
            180                 185                 190

Gly Gly Gln Pro Gly Gly Gln
        195
```